United States Patent
Stengel

(10) Patent No.: US 12,103,956 B2
(45) Date of Patent: Oct. 1, 2024

(54) SUICIDE MODULE COMPOSITIONS AND METHODS

(71) Applicant: Caribou Biosciences, Inc., Berkeley, CA (US)

(72) Inventor: Katharina F. S. Stengel, Oakland, CA (US)

(*) Notice: Subject to any disclaimer, the term of this patent is extended or adjusted under 35 U.S.C. 154(b) by 820 days.

(21) Appl. No.: 17/270,827

(22) PCT Filed: Sep. 30, 2019

(86) PCT No.: PCT/US2019/053903
§ 371 (c)(1),
(2) Date: Feb. 23, 2021

(87) PCT Pub. No.: WO2020/072390
PCT Pub. Date: Apr. 9, 2020

(65) Prior Publication Data
US 2021/0214416 A1 Jul. 15, 2021

Related U.S. Application Data

(60) Provisional application No. 62/739,483, filed on Oct. 1, 2018.

(51) Int. Cl.
| C07K 14/705 | (2006.01) |
| A61K 35/17 | (2015.01) |
| C07K 14/725 | (2006.01) |
| C07K 14/74 | (2006.01) |
| C12N 15/86 | (2006.01) |

(52) U.S. Cl.
CPC .......... *C07K 14/7051* (2013.01); *A61K 35/17* (2013.01); *C07K 14/70517* (2013.01); *C07K 14/70539* (2013.01); *C07K 14/70578* (2013.01); *C12N 15/86* (2013.01); *C07K 2317/622* (2013.01); *C07K 2319/03* (2013.01); *C12N 2750/14143* (2013.01)

(58) Field of Classification Search
None
See application file for complete search history.

(56) References Cited

FOREIGN PATENT DOCUMENTS

| WO | WO2016090320 | 6/2016 |
| WO | WO2017181119 | 10/2017 |

OTHER PUBLICATIONS

Lederman et al. (Molecular Immunology 28: 1171-1181, 1991).*
Houghten et al. (New Approaches to Immunization, Vaccines 86, Cold Spring Harbor Laboratory, p. 21-25, 1986).*
Li et al. (PNAS 77: 3211-3214, 1980).*
PCT Written Opinion of the International Searching Authority for related International Application No. PCT/US2019/053903.
Valton J. et al. : "A Versatile Safeguard for Chimeric Antigen Receptor T-Cell Immunotherapies", Scientific Reports, (2018) vol. 8, 8972.
Li H. et al. : "Increasing the safety and efficacy of chimeric antigen receptor T cell therapy", Protein & Cell, Springer Asia, Beijing, CN, (2017) vol. 8, No. 8, pp. 573-589.
Gornalusse G. et al. : "HLA-E-expressing pluripotent stem cells escape allogeneic responses and lysis by NK cells", Nature Biotechnology, (2017) vol. 35, pp. 765-772.
Philip et al. : "A highly compact epitope-based marker/suicide gene for easier and safer T-cell therapy" Blood (2014) 124:1277-1287.
Qasim et al. : "Molecular remission of infant B-ALL after infusion of universal TALEN gene-edited CAR T cells" Science Translational Medicine (2017) 9:374.
PCT Search report of the International Searching Authority for related International Application No. PCT/US2019/053903.

* cited by examiner

*Primary Examiner* — Sharon X Wen
(74) *Attorney, Agent, or Firm* — Barbara McClung; Olga Zimmerman

(57) ABSTRACT

Chimeric transmembrane proteins comprising one or more suicide modules and methods of making and using these constructs are disclosed. The chimeric transmembrane proteins comprise one or more suicide module and a transmembrane domain. Engineered cells comprising such chimeric transmembrane proteins and methods of using such engineered cells are also disclosed.

13 Claims, 3 Drawing Sheets

Specification includes a Sequence Listing.

BCMA SUICIDE SWITCH MODULES

A | ECD | TM | ICD |        BCMA FL

B | ECD | TM | ICD |        BCMA ICD TRUNCATED I

C | ECD | TM |              BCMA ICD TRUNCATED II

D | ECD | CD8TM |            BCMA CD8 TM

E | ECD | LINKER | CD8TM |   BCMA LINKER

F | ECD | CD34 | CD8TM |     BCMA CD34 EPITOPE

FIG. 3

SUICIDE MODULE COMPOSITIONS AND METHODS

CROSS-REFERENCE TO RELATED APPLICATIONS

This application is a national stage entry of International Application No. PCT/US2019/053903, filed 30 Sep. 2019, which claims the benefit of U.S. Provisional Patent Application Ser. No. 62/739,483, filed 1 Oct. 2018, the contents of which applications are incorporated herein by reference in their entireties.

STATEMENT REGARDING FEDERALLY SPONSORED RESEARCH OR DEVELOPMENT

Not applicable.

SEQUENCE LISTING

The present application contains a Sequence Listing that has been submitted electronically in ASCII format and is hereby incorporated by reference in its entirety. The ASCII copy, created on 22 Feb. 2021 is named CBI034-10 ST25.txt and is 109 KB in size.

TECHNICAL FIELD

The present invention relates to compositions and methods for ameliorating cell-associated toxicities that can occur with autologous and allogeneic cell therapies. More particularly, the present invention pertains to chimeric transmembrane proteins comprising suicide modules to treat and/or prevent Graft versus Host Disease and other undesirable side effects of cell therapies, such as cytokine release syndrome (CRS) and neurotoxicity.

BACKGROUND

Adoptive cell therapy (ACT) and stem cell transplant (SCT) therapies use potent native or engineered immune cells to treat diseases such as cancer. These treatments utilize cells from either a specific patient returned to that patient (autologous cell therapy) or cells from a third-party donor (allogeneic cell therapy) to treat the patient.

Allogeneic cell therapies, such as bone marrow transplants, stem cell transplants, allogeneic T cell therapies, and allogeneic chimeric antigen receptor (CAR) T cell therapies, are rapidly becoming state of the art treatments. Allogeneic therapies have several advantages over autologous therapies, including the ability to administer higher numbers of cells, as well as administration of healthier, non-exhausted cells. However, donor cells come with serious drawbacks. For example, patients that receive allogeneic cell transplants can experience Graft versus Host Disease (GvHD), which can be life-threatening. GvHD is caused by unique, polymorphous human leukocyte antigen (HLA) class I genes present in each individual. These genes are recognized by T cell receptors (TCRs). Typically, when HLA genes and T cell receptors are perfectly matched, immune self-tolerance exists and no cell killing occurs. Conversely, GvHD can occur when the donor and the recipient are not matched for their HLA class I genes. In this case, donor immune cells attack the recipient's cells.

To prevent GvHD in allogeneic cell transplants, the T cell receptor a constant (TRAC) locus coding for the portion of the T cell receptor that recognizes foreign HLA class I genes can be disrupted using several gene editing methods.

Similarly, the patient's immune cells can attack the MHC mismatched, grafted allogeneic cells and kill them. This is termed "Host versus Graft rejection." Thus, the therapy can fail because the number of grafted cells can be severely depleted below efficacious levels. To prevent Host versus Graft rejection, the B2 microglobulin (B2M, beta-2 microglobulin) locus coding for an essential protein in major histocompatibility complex (MHC) class I molecules on donor cells can be disrupted using gene editing methods in order to prevent presentation of these molecules at the transplant cell surface and thus prevent graft rejection. See, e.g., Gornalusse et al., *Nat. Biotechnol.* (2017) 35:765-772. However, B2M disruption leaves the adoptive cell transplant vulnerable to killing by host natural killer (NK) cells. Usually, cells are protected from NK cell-mediated killing by presenting HLA-E (an MHC class I molecule) complexed with a peptide on the cell surface. However, HLA-E also forms a complex with B2M to be presented at the cell surface. To prevent host NK cell-mediated killing of the allogeneic graft, single-chain B2M/HLA-E fusions can be introduced into allogeneic cells using a vector, or integrated into the endogenous B2M locus, leading to MHC class I-deficient cells that only present HLA-E at the cell surface. However, because these cells are now immune to killing by the recipient's immune system, other problematic side effects of the therapy can occur, such as residual GvHD, cytokine release syndrome (CRS), cytokine storm, neurotoxicity, or oncogenic transformations of the graft.

In order to kill the grafted cells at will, suicide switches, or cell depletion modules, can be engineered into the cells. These switches can be activated by antibodies or small molecules. A number of these switches have been developed, including independent kill switch modules, and kill switch modules coupled to a CAR expression cassette or to the CAR itself. See, e.g., Li et al., *Protein Cell* (2017) 8:573-589; Valton et al., *Scientific Reports* (2018) 8:8972. One such suicide switch is based on a mimotope of CD20, a B cell protein that can be targeted by the drug rituximab (Rituxan®, Genentech, South San Francisco, CA), an antibody that targets CD20. This suicide module can be incorporated into a protein, such as RQR8 (Philip et al., *Blood* (2014) 124:1277-1287; Quasim et al., *Science Translational Medicine* (2017) 9:374, or into a CAR construct (Valton et al., *Scientific Reports* (2018) 8:8972). However, this module makes the CAR-carrying cells vulnerable to killing by rituximab, which is widely used in therapy and hence is unsuitable in patients undergoing rituximab treatment.

Moreover, a significant number of cells can lose suicide switch expression and still retain the CAR in uncoupled systems. Additionally, in coupled systems, some CAR constructs may not be amendable to the addition of suicide switch modules and may not retain CAR activity.

Thus, new suicide module designs for ameliorating side effects associated with adoptive cell therapies are needed.

SUMMARY

The present invention pertains to chimeric transmembrane proteins comprising suicide modules and methods using such proteins to treat and/or prevent Graft versus Host Disease, Host versus Graft rejection, and other undesirable cell toxicities and side effects of allogeneic cell therapies. The compositions and methods described herein can be used to provide more efficacious treatments, such as in cell therapy applications, with less deleterious side effects.

Accordingly, in one embodiment, a construct comprising a suicide module is provided. The suicide module comprises a ligand binding domain operably linked to a heterologous transmembrane domain (TM). The ligand binding domain comprises a B cell maturation antigen (BCMA) extracellular domain (ECD), a portion of the BCMA ECD, or a mimotope thereof.

In certain embodiments, the ligand binding domain comprises amino acids 6 to 41 of SEQ ID NO:3 or a variant thereof that retains ligand binding activity. In additional embodiments, the ligand binding domain comprises the amino acid sequence of SEQ ID NO:3 or a variant thereof that retains ligand binding activity.

In additional embodiments, the construct further comprises a BCMA intracellular membrane domain (ICD) or a fragment thereof. In certain embodiments, the ICD comprises the amino acid sequence of SEQ ID NO:5, SEQ ID NO:6, or SEQ ID NO:4.

In further embodiments, the heterologous TM of the construct comprises a CD8 TM, such as a TM comprising the amino acid sequence of SEQ ID NO:13.

In additional embodiments, the construct comprises a linker sequence linking the ligand binding domain to the TM. In certain embodiments, the linker sequence is selected from the group consisting of SEQ ID NOS: 15-26 and 27. In other embodiments, the linker sequence comprises a sequence from CD34, such as a sequence comprising the amino acid sequence of SEQ ID NO:38.

In yet additional embodiments, the construct comprises an amino acid sequence selected from SEQ ID NOS: 48-50 and 51.

In further embodiments, a chimeric antigen receptor (CAR) construct is provided that comprises a suicide module construct as described herein, wherein the CAR construct comprises a single-chain immunoglobulin variable fragment (scFv) and a CAR signaling domain. In certain embodiments, the suicide module construct is located between the scFv and the CAR signaling domain, upstream of the scFv and the CAR signaling domain, or downstream of the scFv and CAR signaling domain.

In additional embodiments, a self-cleaving peptide, such as a 2A peptide, is located between the suicide module construct and the remainder of the CAR construct.

In further embodiments, the scFv of the CAR construct comprises an anti-CD19 scFv.

In additional embodiments, a CAR construct is provided that comprises a suicide module, wherein the CAR construct comprises an amino acid sequence selected from the group consisting of SEQ ID NOS: 52-55 and 56.

In further embodiments, a construct is provided that comprises at least one suicide module component comprising a ligand binding domain and a TM; a beta-2 microglobulin (B2M) component; a human leukocyte antigen E (HLA-E) component; an HLA-G peptide component; and at least one linker component. In certain embodiments, the components in the construct are located as depicted in FIGS. 2B-2F.

In additional embodiments, the linker component is selected from the group consisting of SEQ ID NOS: 15-26 and 27.

In certain embodiments, the HLA-E component comprises the sequence of SEQ ID NO: 33.

In additional embodiments, the HLA-G peptide component comprises the sequence of SEQ ID NO:36.

In further embodiments, the B2M component comprises the sequence of SEQ ID NO:30.

In yet additional embodiments, the suicide module component comprises a BCMA-based suicide module as described herein.

In further embodiments, a construct is provided that comprises a suicide module component comprising a ligand binding domain and a TM; a beta-2 microglobulin (B2M) component; a human leukocyte antigen E (HLA-E) component; an HLA-G peptide component;
and at least one linker component, wherein the amino acid sequence of the construct is selected from the group consisting of SEQ ID NOS: 59-62 and 63.

In additional embodiments, a polynucleotide comprising a coding sequence encoding any one of the constructs as described above is provided. In further embodiments, a recombinant vector is provided. The recombinant vector comprises the polynucleotide and regulatory elements operably linked to the polynucleotide, whereby the coding sequence is capable of being transcribed and translated in an adoptive host cell. In certain embodiments, the recombinant vector is a viral vector, such as an adeno-associated virus vector.

In further embodiments, an adoptive host cell transformed with the recombinant vector is provided. In certain embodiments, the adoptive host cell is a lymphocyte, such as a T cell or a CAR-T cell. In other embodiments, the adoptive host cell is a stem cell.

In additional embodiments, a method of selectively killing an adoptive cell is provided. The method comprises delivering to the adoptive cell a polynucleotide or recombinant vector, as above, under conditions that provide expression of the ligand binding domain at the adoptive cell surface; and delivering to the cell a ligand capable of binding the ligand binding domain, whereby cell killing occurs. In certain embodiments, the ligand is an antibody that binds the ligand binding domain. In additional embodiments, the antibody is conjugated to a cytotoxic molecule that is capable of killing the adoptive cell.

In additional embodiments, a chimeric transmembrane protein is provided. The chimeric transmembrane protein comprises one or more suicide modules, wherein the suicide module comprises a ligand binding domain, and wherein the ligand binding domain is selected from the group a B cell maturation antigen extracellular domain, a portion of the B cell maturation antigen extracellular domain, a mimotope of a B cell maturation antigen extracellular domain, and combinations thereof; and a transmembrane domain. In certain embodiments the ligand binding domain comprises amino acids 6 to 41 of SEQ ID NO:3 or an amino acid sequence having at least 80 percent sequence identity to SEQ ID NO:3, and wherein the ligand binding domain retains ligand binding activity.

In further embodiments, the chimeric transmembrane protein further comprises a B cell maturation antigen intracellular membrane domain or a fragment thereof. In certain embodiments, the B cell maturation antigen intracellular membrane domain or fragment thereof comprises the amino acid sequence of SEQ ID NO:5, SEQ ID NO:6, SEQ ID NO:4, or an amino acid sequence having at least 80 percent sequence identity to SEQ ID NO:5, SEQ ID NO:6, and SEQ ID NO:4.

In another embodiment, the chimeric transmembrane protein comprises a CD8 transmembrane domain.

In additional embodiments, the chimeric transmembrane protein comprises a linker sequence linking the ligand binding domain to the transmembrane domain.

In additional embodiments, the linker sequence is selected from the group consisting of SEQ ID NO:15, SEQ ID NO:16, SEQ ID NO:17, SEQ ID NO: 18, SEQ ID NO: 19, SEQ ID NO: 20, SEQ ID NO:21, SEQ ID NO:22, SEQ ID NO:23, SEQ ID NO:24 SEQ ID NO:25, SEQ ID NO:26, and SEQ ID NO:27.

In further embodiments, the chimeric transmembrane protein comprises an amino acid sequence selected from the group consisting of SEQ ID NO:48, SEQ ID NO:49, SEQ ID NO:50, and SEQ ID NO:51.

In additional embodiments, the chimeric transmembrane protein further comprises a chimeric antigen receptor, wherein the chimeric antigen receptor comprises a single-chain immunoglobulin variable fragment and a chimeric antigen receptor signaling domain.

In additional embodiments, the suicide module is located between the single-chain immunoglobulin variable fragment and the chimeric antigen receptor signaling domain.

In further embodiments, the suicide module is located N-terminal of the single-chain immunoglobulin variable fragment and the chimeric antigen receptor signaling domain.

In additional embodiments, the single-chain immunoglobulin variable fragment comprises an anti-CD19 single-chain immunoglobulin variable fragment.

In additional embodiments, a self-cleaving peptide is located between the suicide module and the chimeric antigen receptor.

In additional embodiments, a chimeric transmembrane protein comprising one or more suicide modules, a beta-2 microglobulin domain, and a human leukocyte antigen E domain is provided.

In additional embodiments, a self-cleaving peptide is operably linked to the suicide module.

In further embodiments, an engineered cell comprising the chimeric transmembrane protein is provided. In certain embodiments, the engineered cell is a CAR-T cell.

In additional embodiments, a method of selectively killing the engineered cell is provided. The method comprises delivering to the engineered cell a ligand capable of binding the ligand binding domain, thereby resulting in cell death. In an additional embodiment, the ligand is an antibody capable of binding the ligand binding domain.

In additional embodiments, the antibody is conjugated to a cytotoxic molecule, and the conjugated antibody-cytotoxic molecule is selected from the group consisting of GSK2857916, MEDI2228, AMG 224, and HDP-101.

These aspects and other embodiments of the present invention will readily occur to those of ordinary skill in the art in view of the disclosure herein.

INCORPORATION BY REFERENCE

All publications, patents, and patent applications mentioned in the present Specification are herein incorporated by reference to the same extent as if each individual publication, patent, or patent application was specifically and individually indicated to be incorporated by reference.

BRIEF DESCRIPTION OF THE FIGURES

FIGS. 3A-3F illustrate exemplary BCMA-based suicide modules of the present invention.

DETAILED DESCRIPTION OF THE INVENTION

Figure 1:
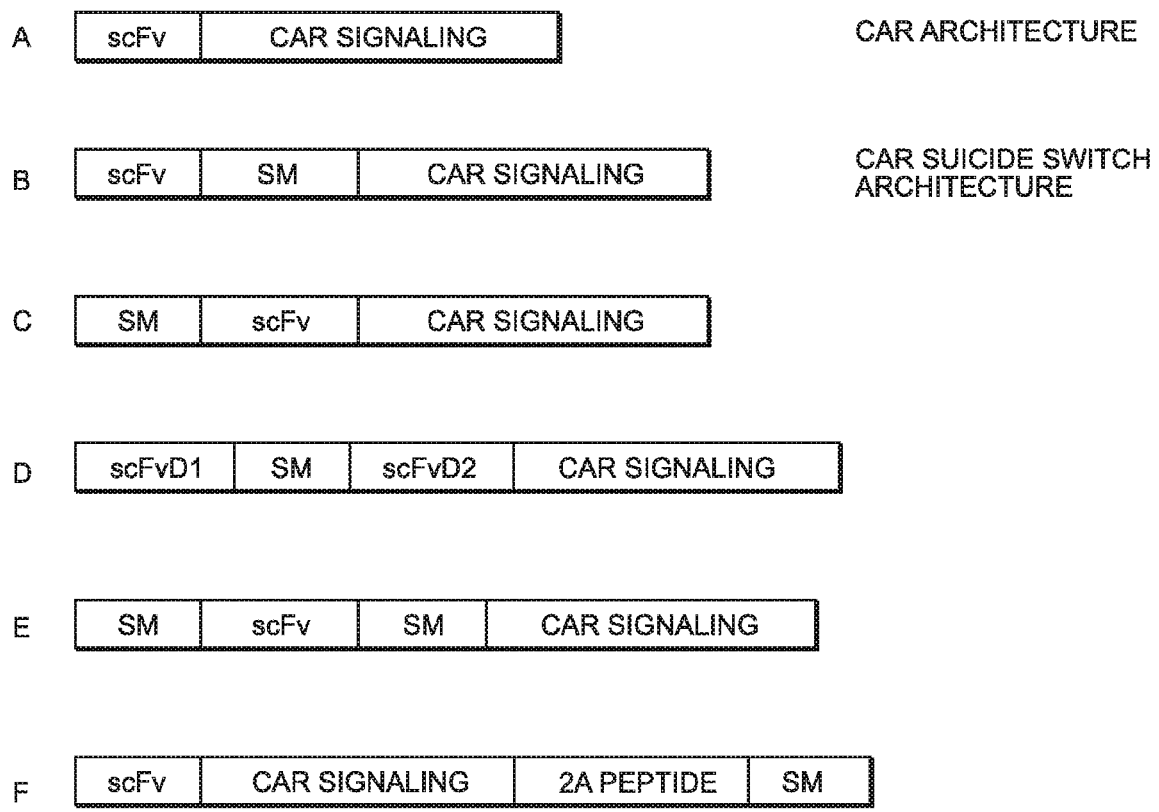
FIG. 1A illustrates an exemplary CAR.
FIGS. 1B-1F illustrate exemplary CAR constructs comprising suicide modules (SM) of the present invention.

It is to be understood that the terminology used herein is for the purpose of describing particular embodiments only, and is not intended to be limiting. As used in the present Specification and the appended claims, the singular forms "a," "an," and "the" include plural referents unless the context clearly dictates otherwise. Thus, for example, reference to "a T cell" includes a population of one or more T cells, and the like.

Unless defined otherwise, all technical and scientific terms used herein have the same meaning as commonly understood by one of ordinary skill in the art to which the present invention pertains. Although other methods and materials similar, or equivalent, to those described herein can be used in the practice of the present invention, preferred materials and methods are described herein.

In view of the teachings of the present Specification, one of ordinary skill in the art can apply conventional techniques of immunology, biochemistry, chemistry, molecular biology, microbiology, cell biology, genomics, and recombinant polynucleotides, as taught, for example, by the following standard texts: Antibodies: A Laboratory Manual, Second edition, E. A. Greenfield, 2014, Cold Spring Harbor Laboratory Press, ISBN 978-1-936113-81-1; Culture of Animal Cells: A Manual of Basic Technique and Specialized Applications, 6th Edition, R. I. Freshney, 2010, Wiley-Blackwell, ISBN 978-O-470-52812-9; Transgenic Animal Technology, Third Edition: A Laboratory Handbook, 2014, C. A. Pinkert, Elsevier, ISBN 978-0124104907; The Laboratory Mouse, Second Edition, 2012, H. Hedrich, Academic Press, ISBN 978-0123820082; Manipulating the Mouse Embryo: A Laboratory Manual, 2013, R. Behringer, et al., Cold Spring Harbor Laboratory Press, ISBN 978-1936113019; PCR 2: A Practical Approach, 1995, M. J. McPherson, et al., IRL Press, ISBN 978-0199634248; Methods in Molecular Biology (Series), J. M. Walker, ISSN 1064-3745, Humana Press; RNA: A Laboratory Manual, 2010, D. C. Rio, et al., Cold Spring Harbor Laboratory Press, ISBN 978-0879698911; Methods in Enzymology (Series), Academic Press; Molecular Cloning: A Laboratory Manual (Fourth Edition), 2012, M. R. Green, et al., Cold Spring Harbor Laboratory Press, ISBN 978-1605500560; Bioconjugate Techniques, Third Edition, 2013, G. T. Hermanson, Academic Press, ISBN 978-0123822390; Methods in Plant Biochemistry and Molecular Biology, 1997, W. V. Dashek, CRC Press, ISBN 978-0849394805.

Definitions

The terms "suicide module," "suicide switch," and "safety switch" are used interchangeably herein and refer to a molecule, such as a polypeptide comprising a ligand binding domain that allows for selective destruction of adoptively transferred cells. For example, an adoptive cell can be genetically engineered to include one or more suicide modules that prompt cell death when exposed to selected conditions. Several types of suicide modules are known and include suicide modules that are triggered by metabolic conditions; modules that are induced by dimerization; and modules that are triggered by selected monoclonal antibodies. In some embodiments, a suicide module comprises at least one ligand binding domain as well as a transmembrane domain that anchors the ligand binding domain to the cell membrane. Such suicide modules are described in detail herein. A "suicide gene" encodes a protein that possesses an inducible capacity to lead to cellular death and can be incorporated into a polynucleotide construct to produce a suicide module.

By "ligand binding domain," in the context of a suicide module, is meant a peptide presented on an adoptive cell surface that is capable of selectively binding a cognate ligand, such as an antibody or an antibody-drug conjugate (ADC), wherein when the antibody or ADC is bound to the ligand binding domain, death of the adoptive cell occurs. An epitope is therefore a type of ligand binding domain and is described further herein.

By "ligand" is meant a molecule that is capable of binding a ligand binding domain. Ligands can comprise small molecules, antibodies, antibody fragments, peptides, proteins, biologically active drugs, and the like. A ligand that can bind a certain ligand binding domain has binding activity for that domain. A ligand typically has an affinity to the ligand binding domain. Affinities of ligands for ligand binding domains can be low, medium, or high affinity. Affinities of ligands for ligand binding domains can be measured such as with isothermal titration calorimetry (ITC), fluorescence assisted cell sorting (FACS), surface plasmon resonance (SPR), nuclear magnetic resonance (NMR), and other known techniques.

By "adoptive cell" is meant a cell that can be genetically modified for use in a cell therapy treatment, such for treating cancer and/or preventing GvHD and other undesirable side effects of cell therapies, such as, but not limited to, cytokine storm, oncogenic transformations of the administered genetically modified material, neurological disorders, and the like. Adoptive cells include, but are not limited to, stem cells, induced pluripotent stem cells (iPSCs), cord blood stem cells, lymphocytes, macrophages, red blood cells, fibroblasts, endothelial cells, epithelial cells, and pancreatic precursor cells.

By "cell therapy" is meant the treatment of a disease or disorder that utilizes genetically modified cells. Genetic modifications can be introduced using methods described herein, such as methods comprising viral vectors, nucleofection, gene gun delivery, sonoporation, cell squeezing, lipofection, or the use of other chemicals, cell penetrating peptides, and the like.

By "adoptive cell therapy" or "ACT" is meant a therapy that uses genetically modified adoptive cells derived from either a specific patient returned to that patient (autologous cell therapy) or from a third-party donor (allogeneic cell therapy), to treat the patient. ACTs, include, but are not limited to, bone marrow transplants, stem cell transplants, T cell therapies, CAR-T cell therapies, and natural killer (NK) cell therapies.

By "lymphocyte" is meant a leukocyte (white blood cell) that is part of the vertebrate immune system. Also encompassed by the term "lymphocyte" is a hematopoietic stem cell that gives rise to lymphoid cells. Lymphocytes include T cells for cell-mediated, cytotoxic adaptive immunity, such as CD4+ and/or CD8+ cytotoxic T cells; alpha/beta T cells and gamma/delta T cells; regulatory T cells, such as Treg cells; NK cells that function in cell-mediated, cytotoxic innate immunity; B cells, for humoral, antibody-driven adaptive immunity; NK/T cells; cytokine induced killer cells (CIK cells); and antigen presenting cells (APCs), such as dendritic cells. A lymphocyte can be a mammalian cell, such as a human cell.

The term "lymphocyte" also encompasses genetically modified T cells and NK cells, modified to produce chimeric antigen receptors (CARs) on the T or NK cell surface (CAR-T cells and CAR-NK cells). These CAR-T cells recognize specific soluble antigens or antigens on a target cell surface, such as a tumor cell surface, or on cells in the tumor microenvironment. A CAR can comprise one or more extracellular ligand binding domains, a hinge region, a transmembrane region, and an intracellular signaling region. The extracellular ligand binding domain typically comprises a single-chain immunoglobulin variable fragment, (scFv) or other ligand binding domain, such as a natural protein ligand. The hinge region generally comprises a polypeptide hinge of variable length such as one or more amino acids, a CD8 alpha or an IgG4 region (or others), and combinations thereof. The transmembrane domain typically contains a transmembrane region derived from CD8 alpha, CD28, or other transmembrane proteins such as DAP10, DAP12, or NKG2D, and combinations thereof. The intracellular signaling domain consists of one or more intracellular signaling domains such as CD28, 4-1BB, CD3 zeta, OX40, 2B4, or other intracellular signaling domains, and combinations thereof. When the extracellular ligand binding domain binds to a cognate ligand, the intracellular signaling domain of the CAR activates the lymphocyte. See, e.g., Brudno et al., *Nature Rev. Clin. Oncol.* (2018) 15:31-46; Maude et al., *N. Engl. J. Med.* (2014) 371:1507-1517; Sadelain et al., *Cancer Disc.* (2013) 3:388-398 (2018); U.S. Pat. Nos. 7,446,190 and 8,399,645 (each of which is incorporated herein by reference in its entireties) for descriptions of CAR-T cells, methods of making the same, and uses thereof. For exemplary cellular targets and the CAR scFvs/binding proteins that target the exemplary cellular targets, see Table 1.

TABLE 1

List of exemplary cellular targets and CAR scFv binding proteins that target the exemplary cellular targets

| Cellular target | CAR scFv/binding protein |
| --- | --- |
| CD19 | anti-CD19 |
| CD20 | anti-CD20 |
| CD22 | anti-CD22 |
| CD30 | anti-CD30 |
| CD33 | anti-CD33 |
| CD138 | anti-CD138 |
| CD171/L1CAM | anti-CD171 |
| CEA | anti-CEA |
| CD123 | anti-CD123 |
| IL13 Receptor Alpha | IL13 |
| Epidermal growth factor receptor | anti-Epidermal growth factor receptor |
| EFGRvIII | anti-EFGRvIII |
| ErbB | anti-ErbB |
| FAP | anti-FAP |
| GD2 | anti-GD2 |
| Glypican 3 | anti-Glypican 3 |
| Her2 | anti-Her2 |
| Mesothelin | anti-Mesothelin |
| ULBP and MICA/B proteins | NKG2D |
| PD1 | anti-PD1 |
| MUC1 | anti-MUC1 |
| VEGF2 | anti-VEGF2 |
| SLAMF7 | anti-SLAMF7 |
| BCMA | anti-BCMA |
| WT1 | anti-WT1 |
| MUC16 | anti-MUC16 |
| Lewis Y/LeY | anti-LeY |
| FLT3 | FLT3 ligand/anti-FLT3 |
| ROR1 | anti-ROR1 |

Also encompassed by the term "lymphocyte," as used herein, are T cell receptor engineered T cells (TCRs), genetically engineered to express one or more specific, naturally occurring or engineered T cell receptors that can recognize protein or (glyco) lipid antigens of target cells presented by the Major Histocompatibility Complex (MHC). Small pieces of these antigens, such as peptides or fatty acids, are shuttled to the target cell surface and presented to the T cell receptors as part of the MHC. T cell receptor binding to antigen-loaded MHCs activates the lymphocyte.

Tumor infiltrating lymphocytes (TILs) are also encompassed by the term "lymphocyte," as used herein. TILs are immune cells that have penetrated the environment in and around a tumor ("the tumor microenvironment"). TILs are typically isolated from tumor cells and the tumor microenvironment and are selected in vitro for high reactivity against tumor antigens. TILs are grown in vitro under conditions that overcome the tolerizing influences that exist in vivo and are then introduced into a subject for treatment.

CARs can also be incorporated into TILs, NK cells, or TCRs resulting in CAR-TILs, CAR-NK cells, or TCR engineered CAR-T cells.

As used herein, "stem cell" refers to a cell that has the capacity for self-renewal, i.e., the ability to go through numerous cycles of cell division while maintaining the undifferentiated state. Stem cells can be totipotent, pluripotent, multipotent, oligopotent, or unipotent. Stem cells are embryonic, fetal, amniotic, adult, or induced pluripotent stem cells.

As used herein, "induced pluripotent stem cells" or iPSCs, refers to a type of pluripotent stem cell that is artificially derived from a non-pluripotent cell, typically an adult somatic cell, by inducing expression of specific genes.

As used herein, "hematopoietic stem cell" refers to an undifferentiated cell that has the ability to differentiate into a hematopoietic cell, such as a lymphocyte.

The terms "subject," "individual," or "patient" are used interchangeably herein and refer to any member of the phylum Chordata, including, without limitation, humans and other primates, including non-human primates such as rhesus macaques, chimpanzees, and other monkey and ape species; farm animals, such as cattle, sheep, pigs, goats, and horses; domestic mammals, such as dogs and cats; laboratory animals, including rabbits, mice, rats, and guinea pigs; birds, including domestic, wild, and game birds, such as chickens, turkeys, and other gallinaceous birds, ducks, and geese; and the like. The term does not denote a particular age or gender. Thus, the term includes adult, young, and newborn individuals as well as males and females. In some embodiments, a host cell is derived from a subject (for example, lymphocytes, stem cells, progenitor cells, or tissue-specific cells). In some embodiments, the subject is a non-human subject.

The terms "effective amount" or "therapeutically effective amount" of a composition or agent, such as a genetically engineered adoptive cell as provided herein, refer to a sufficient amount of the composition or agent to provide the desired response, such as to prevent or eliminate one or more harmful side effects associated with allogeneic adoptive cell therapies. Such responses will depend on the particular disease in question. For example, in a patient being treated for cancer using an adoptive cell therapy, a desired response includes, but is not limited to, treatment or prevention of the effects of GvHD, Host versus Graft rejection, cytokine release syndrome (CRS), cytokine storm, and the reduction of oncogenic transformations of administered genetically modified cells. The exact amount required will vary from subject to subject, depending on the species, age, and general condition of the subject, the severity of the condition being treated, and the particular modified lymphocyte used, mode of administration, and the like. An appropriate "effective" amount in any individual case may be determined by one of ordinary skill in the art using routine experimentation.

"Treatment" or "treating" a particular disease, such as cancerous condition, or Graft versus Host disease, includes: preventing the disease, for example, preventing the development of the disease or causing the disease to occur with less intensity in a subject that may be predisposed to the disease but does not yet experience or display symptoms of the disease; inhibiting the disease, for example, reducing the rate of development, arresting the development or reversing the disease state; and/or relieving symptoms of the disease, for example, decreasing the number of symptoms experienced by the subject.

The terms "engineered," "genetically engineered," "genetically modified," "recombinant," "modified," and "non-naturally occurring" indicate intentional human manipulation of the genome of an organism or cell. The terms encompass methods of genomic modification that include genomic editing, as defined herein, as well as techniques that alter gene expression or inactivation, enzyme engineering, directed evolution, knowledge-based design, random mutagenesis methods, gene shuffling, codon optimization, and the like. Methods for genetic engineering are known in the art.

By "gene editing" or "genome editing," as used herein, is meant a type of genetic engineering that results in a genetic modification, such as an insertion, deletion, or replacement of a nucleotide sequence, or even a single base, at a specific site in a cell genome. The terms include, without limitation, heterologous gene expression, gene or promoter insertion or deletion, nucleic acid mutation, and a disruptive genetic modification, as defined herein.

As used herein, the terms "peptide," "polypeptide," and "protein" are interchangeable and refer to polymers of amino acids. As used herein, the term "amino acid" refers to natural and synthetic (unnatural) amino acids, including amino acid variants, modified amino acids, peptidomimetics, glycine, and D or L optical isomers. A polypeptide may be of any length. It may be branched or linear, it may be interrupted by non-amino acids, and it may comprise modified amino acids. The terms may be used to refer to an amino acid polymer that has been modified through, for example, acetylation, disulfide bond formation, glycosylation, lipidation, phosphorylation, cross-linking, and/or conjugation (e.g., with a labeling component or ligand). Polypeptide sequences are displayed herein in the conventional N-terminal to C-terminal orientation.

The polypeptide need not include the full-length amino acid sequence of the reference molecule but can include only so much of the molecule as necessary in order for the polypeptide to function as intended, such as to bind a cognate antibody. Thus, only one or few epitopes of the reference molecule need be present. Furthermore, the polypeptide may comprise a fusion protein between the full-length reference molecule or a fragment of the reference molecule and another protein that does not disrupt the intended reactivity of, for example, the suicide module. It is readily apparent that the polypeptide may therefore comprise the full-length sequence, fragments, truncated and partial sequences, as well as variants and precursor forms of the reference molecule. The term also intends deletions, additions, and substitutions to the reference sequence, so long as the polypeptide retains immunoreactivity.

Thus, the full-length proteins and fragments thereof, as well as proteins with modifications, such as deletions, additions, and substitutions (either conservative or non-conservative in nature), to the native sequence, are intended for use herein, so long as the protein maintains the desired activity. These modifications may be deliberate, as through site-directed mutagenesis, or may be accidental, such as through mutations of hosts, which produce the proteins or errors due to PCR amplification. Accordingly, active proteins substantially homologous to the parent sequence, e.g., proteins with 70 . . . 80 . . . 85 . . . 90 . . . 95 . . . 98 . . . 99%, etc. identity that retain the desired activity, are contemplated for use herein.

Sequence identity between two polynucleotide sequences or two polypeptide sequences is generally calculated using the standard default parameters of the various methods or computer programs. A high degree of sequence identity, as used herein, between two polynucleotides or two polypeptides is typically between about 90% identity and 100% identity, for example, about 90% identity or greater, preferably about 95% identity or greater, more preferably about 98% identity or greater. A moderate degree of sequence identity, as used herein, between two polynucleotides or two polypeptides is typically between about 80% identity to about 89% identity, for example, about 80% identity or greater, preferably about 85% identity. A low degree of sequence identity, as used herein, between two polynucleotides or two polypeptides is typically between about 50% identity and 79% identity, for example, about 50% identity, preferably about 60% identity, more preferably about 75% identity. For example, a ligand binding domain (e.g., a BCMA domain comprising amino acid substitutions) can have a low degree of sequence identity, a moderate degree of sequence identity, or a high degree of sequence identity, over its length to a reference BCMA protein (e.g., a wild-type BCMA).

The term "variant" refers to derivatives of the reference molecule that retain the desired activity, or fragments of such derivatives that retain activity, as described above. In general, the term "variant" refers to compounds having a native polypeptide sequence and structure with one or more amino acid additions, substitutions and/or deletions, relative to the native molecule. Particularly preferred analogs include substitutions that are conservative in nature, i.e., those substitutions that take place within a family of amino acids that are related in their side chains. Specifically, amino acids are generally divided into four families: (a) acidic—aspartate and glutamate; (b) basic—lysine, arginine, histidine; (c) non-polar—alanine, valine, leucine, isoleucine, proline, phenylalanine, methionine, tryptophan; and (d) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. The polypeptide of interest may include up to about 5-10 conservative or non-conservative amino acid substitutions, or even up to about 15-25 or 50 conservative or non-conservative amino acid substitutions, or any number between 5-50, so long as the desired function of the molecule remains intact.

Polypeptides and polynucleotides as described herein can be made using routine techniques in the field of molecular biology (see, e.g., standard texts discussed above). Furthermore, essentially any polypeptide or polynucleotide can be custom ordered from commercial sources.

By "epitope" is meant a site on a molecule to which specific B cells and T cells respond. An epitope can comprise 3 or more amino acids in a spatial conformation unique to the epitope. Generally, an epitope consists of at least 5 such amino acids and, more usually, consists of at least 8-10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art, such as by the use of hydrophobicity studies and by site-directed serology.

A "mimotope" is a macromolecule, such as a peptide, that mimics the structure of an epitope. Because of this property, it can cause an antibody response similar to the one elicited by the epitope. An antibody for a given epitope antigen will recognize a mimotope that mimics that epitope. Mimotopes are commonly obtained from phage display libraries through biopanning.

An "antibody" intends a molecule that "recognizes," i.e., specifically binds to an epitope of interest present in a polypeptide, such as a ligand binding domain. By "specifically binds" is meant that the antibody interacts with the epitope in a "lock and key" type of interaction to form a complex between the antigen and antibody. The term "antibody" as used herein includes antibodies obtained from monoclonal preparations, as well as, the following: hybrid (chimeric) antibody molecules; F(ab')2 and F(ab) fragments; Fv molecules (non-covalent heterodimers; single-chain Fv molecules (scFv); dimeric and trimeric antibody fragment constructs; minibodies; humanized antibody molecules; single chain antibodies; cameloid nanobodies; and any functional fragments obtained from such molecules, wherein such fragments retain immunological binding properties of the parent antibody molecule. The antibodies can be sourced from different species, such as human, mouse, rat, rabbit, camel, chicken, and the like. Antibodies and antibody parts can then be further obtained by in vitro techniques, such as by phage display and yeast display. Fully humanized antibodies can be obtained from human plasma, human B cell cloning, mouse, rat, rabbit, chicken, etc., that have an engineered humanized B cell repertoire. Antibodies can then be further modified by affinity maturation and other methods, such as afucosylation or IgG Fc engineering.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F (ab') 2, Fv, and other fragments, as well as chimeric and humanized homogeneous antibody populations, that exhibit immunological binding properties of the parent monoclonal antibody molecule.

"Antibody-dependent cell-mediated cytotoxicity (ADCC)" also referred to as "antibody-dependent cellular cytotoxicity," refers to a mechanism whereby an effector cell of the immune system actively lyses a target cell, such as an adoptive cell, when a membrane-surface ligand binding domain has been bound by a specific antibody. Effector cells are typically natural killer (NK) cells. However, macrophages, neutrophils, and eosinophils can also mediate ADCC. ADCC is independent of complement-dependent cytotoxicity (CDC) that also lyses targets by damaging membranes without the involvement of antibodies or cells of the immune system.

By an "antibody-drug conjugate (ADC)" is meant an antibody, such as a monoclonal antibody, conjugated to a molecule or a biologically active drug or molecule, typically by a chemical linker with labile bonds. By combining the unique targeting of a monoclonal antibody with a cytotoxic drug, ADCs can selectively target adoptive cells that include a ligand binding domain that interacts with the antibody portion of the ADC. After ligand binding by the ligand binding domain, the adoptive cell absorbs or internalizes the antibody together with the cytotoxin. After the ADC is internalized, the cytotoxic drug is released and kills the cell.

The terms "fusion protein" and "chimeric protein," as used herein, refer to a single protein created by joining two or more proteins, protein domains, or protein fragments that do not naturally occur together in a single protein. Chimeric proteins can comprise the full-length sequences of the source proteins, one or more partial sequences of the source proteins, one or more duplications of sequences of source proteins, and any combination thereof. Some chimeric proteins can be hybrids of proteins or fragments of wild-type proteins with artificial polypeptide sequences. Some chimeric proteins can comprise artificial linker sequences. Some chimeric proteins can comprise an extracellular domain (ECD) of one protein, a transmembrane domain (TM) of a second protein and an intracellular domain (ICD) of a third protein. Known examples of artificial chimeric proteins are chimeric antigen receptors (CARs), single-chain B2M/HLA-E fusions. Chimeric proteins can have one or more transmembrane domains from one or more source proteins.

The term "transmembrane domain," as used herein, refers to a protein domain that is typically hydrophobic and embedded in a cellular membrane. Transmembrane domains can be predicted using Bioinformatic programs (e.g., Expasy, World Wide Web: Expasy.org). Transmembrane domains can be formed by alpha-helices or beta-barrels. Proteins that contain a single transmembrane domain are termed Type I, II, III, and IV depending on the topology of the N- and C-termini on the two sides of the lipid bilayer. "Chimeric transmembrane proteins," as used herein, are fusion proteins that comprise one or more transmembrane domains and one or more suicide modules.

Some chimeric proteins can comprise a self-cleaving peptide, such as a 2A peptide. After the self-cleaving peptide undergoes cleavage, parts of the chimeric protein can be released from the chimeric protein.

As used herein, "self-cleaving peptides" are short polypeptide sequences that are cleaved after translation by a ribosome. Self-cleaving peptides comprise peptides, such as P2A from porcine teschovirus-1, E2A from equine rhinitis A virus, F2A from foot-and-mouth disease virus 18, and T2A from Thosea asigna virus. One or more self-cleaving peptides can be fused N-terminally, C-terminally, or internally to other proteins or polypeptides.

As used herein, "extracellular domains" are domains in membrane proteins that protrude from the extracellular side of a cellular membrane. Extracellular domains are connected with one or more transmembrane domain. The connection can be N-terminal, C-terminal, or both. Extracellular domains connected N- and C-terminally to two transmembrane domains are called extracellular loops.

As used herein, "intracellular domains" are domains in membrane proteins that protrude from the intracellular side of a cellular membrane. Intracellular domains are connected with one or more transmembrane domain. The connection can be N-terminal, C-terminal or both. Intracellular domains connected N- and C-terminally to two transmembrane domains are called intracellular loops.

Membrane proteins can have none, one or more intracellular domains. Intracellular domains can comprise ligand binding and signaling domains.

As used herein, the terms "nucleic acid," "nucleotide sequence," "oligonucleotide," and "polynucleotide" are interchangeable. All refer to a polymeric form of nucleotides. The nucleotides may be deoxyribonucleotides (DNA) or ribonucleotides (RNA), or analogs thereof, and they may be of any length. Polynucleotides may perform any function and may have any secondary structure and three-dimensional structure. The terms encompass known analogs of natural nucleotides and nucleotides that are modified in the base, sugar, and/or phosphate moieties. Analogs of a particular nucleotide have the same base-pairing specificity (e.g., an analog of A base pairs with T). A polynucleotide may comprise one modified nucleotide or multiple modified nucleotides. Examples of modified nucleotides include methylated nucleotides and nucleotide analogs. Nucleotide structure may be modified before or after a polymer is assembled. Following polymerization, polynucleotides may be additionally modified via, for example, conjugation with a labeling component or target-binding component. A nucleotide sequence may incorporate non-nucleotide components. The terms also encompass nucleic acids comprising modified backbone residues or linkages that are synthetic, naturally occurring, and non-naturally occurring, and have similar binding properties as a reference polynucleotide (e.g., DNA or RNA). Examples of such analogs include, but are not limited to, phosphorothioates, phosphoramidates, methyl phosphonates, chiral-methyl phosphonates, 2-O-methyl ribonucleotides, peptide-nucleic acids (PNAs), and morpholino structures.

Polynucleotide sequences are displayed herein in the conventional 5' to 3' orientation.

By the term "degenerate variant" is intended a polynucleotide containing changes in the nucleic acid sequence thereof that encodes a polypeptide having the same amino acid sequence as the polypeptide encoded by the polynucleotide from which the degenerate variant is derived. An example of a degenerate variant is a polynucleotide sequence that has been optimized for expression in a particular host cell.

As used herein, the term "sequence identity" generally refers to the percent identity of bases or amino acids determined by comparing a first polynucleotide or polypeptide to a second polynucleotide or polypeptide using algorithms having various weighting parameters. Sequence identity between two polypeptides or two polynucleotides can be determined using sequence alignment by various methods and computer programs (e.g., BLAST, CS-BLAST, FASTA, HMMER, L-ALIGN, etc.), available through the worldwide web at sites including GENBANK (ncbi.nlm.nih.gov/genbank/) and EMBL-EBI (ebi.ac.uk.). Sequence identity between two polynucleotides or two polypeptide sequences is generally calculated using the standard default parameters of the various methods or computer programs.

By "vector" is meant any genetic element, such as a plasmid, phage, transposon, cosmid, chromosome, virus, virion, etc., that is capable of replication when associated with the proper control elements and which can transfer gene sequences to cells. Thus, the term includes cloning and expression vehicles, as well as viral vectors. Vectors can be linear or circular. Vectors can integrate into a target genome of a host cell or replicate independently in a host cell. Vectors can comprise, for example, an origin of replication, a multicloning site, and/or a selectable marker. An "expression vector" typically comprises an expression cassette.

By "recombinant vector" is meant a vector that includes a heterologous nucleic acid sequence capable of expression in vitro or in vivo. The term "heterologous" as it relates to nucleic acid sequences such as coding sequences and control sequences denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct can include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct that is not normally present in the cell would be considered heterologous for purposes herein. Allelic variation or naturally occurring mutational events do not give rise to heterologous DNA, as used herein.

By "recombinant virus" is meant a virus that has been genetically altered, e.g., by the addition or insertion of a heterologous nucleic acid construct into the particle.

"Transformation," as used herein, refers to the insertion of an exogenous polynucleotide into a host cell, irrespective of the method used for insertion. For example, transformation can be by direct uptake, transfection, infection, and the like. The exogenous polynucleotide may be maintained as a nonintegrated vector, for example, an episome, or, alternatively, may be integrated into the host genome.

A "host cell" is a cell that has been transformed, or is capable of transformation, by an exogenous DNA sequence. A host cell can originate from any organism having one or more cells. Examples of host cells include, but are not limited to: a prokaryotic cell, eukaryotic cell, a bacterial cell, an archaeal cell, a cell of a single-cell eukaryotic organism, a protozoa cell, a cell from a plant, an algal cell, a fungal cell (e.g., a yeast cell, a cell from a mushroom), an animal cell, a cell from an invertebrate animal, a cell from a vertebrate animal such as a cell from a mammal (e.g., a pig, a cow, a goat, a sheep, a rodent, a rat, a mouse, a non-human primate, a human, etc.). Furthermore, a host cell can be a stem cell or progenitor cell, and an immunological cell, such as any of the immunological cells described herein.

As used herein, the term "expression cassette" or "expression construct" is a polynucleotide construct, generated recombinantly or synthetically, comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in an expression vector.

A "coding sequence" or a sequence that "encodes" a selected polypeptide, is a nucleic acid molecule that is transcribed (in the case of DNA) and translated (in the case of mRNA) into a polypeptide in vitro or in vivo when placed under the control of appropriate regulatory sequences. The boundaries of the coding sequence are determined by a start codon at the 5' terminus and a translation stop codon at the 3' terminus. A transcription termination sequence may be located 3' to the coding sequence.

As used herein, the terms "regulatory sequences," "regulatory elements," and "control elements" are interchangeable and refer to polynucleotide sequences that are upstream (5' non-coding sequences), within, or downstream (3' non-translated sequences) of a polynucleotide to be expressed. Regulatory sequences influence, for example, the timing of transcription, amount or level of transcription, RNA processing or stability, and/or translation of the related structural nucleotide sequence. Regulatory sequences may include activator binding sequences, enhancers, introns, polyadenylation recognition sequences, promoters, IRES elements, repressor binding sequences, stem-loop structures, translational initiation sequences, translation leader sequences, transcription termination sequences, translation termination sequences, primer binding sites, and the like.

The term "promoter" is used herein in its ordinary sense to refer to a nucleotide region comprising a DNA regulatory sequence, wherein the regulatory sequence is derived from a gene that is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters."

As used herein the term "operably linked" refers to polynucleotide sequences or amino acid sequences placed into a functional relationship with one another. For instance, a promoter or enhancer is operably linked to a coding sequence if it regulates, or contributes to the modulation of, the transcription of the coding sequence. Operably linked DNA sequences encoding regulatory sequences are typically contiguous to the coding sequence. However, enhancers can function when separated from a promoter by up to several kilobases or more. Accordingly, some polynucleotide elements may be operably linked but not contiguous.

As used herein, the term "expression" refers to transcription of a polynucleotide from a DNA template, resulting in, for example, an mRNA or other RNA transcript (e.g., non-coding, such as structural or scaffolding RNAs). The term further refers to the process through which transcribed mRNA is translated into peptides, polypeptides, or proteins. Transcripts and encoded polypeptides are sometimes referred to collectively as a "gene product." Expression may include splicing the mRNA in a eukaryotic cell, if the polynucleotide is derived from genomic DNA.

By "isolated" is meant, when referring to a polypeptide, that the indicated molecule is separate and discrete from the whole organism with which the molecule is found in nature or is present in the substantial absence of other biological macromolecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "purified" as used herein preferably means at least 75% by weight, more preferably at least 85% by weight, more preferably still at least 95% by weight, and most preferably at least 98% by weight, of the same molecule is present.

The present invention is directed to chimeric transmembrane proteins comprising suicide modules, as well as engineered cells comprising these chimeric transmembrane proteins and methods of using these constructs and engineered cells in order to prevent undesirable side effects of autologous and allogeneic cell therapies, such as cytokine release syndrome (CRS), neurotoxicity, and Graft versus Host Disease (GvHD). Because engineered cells, such as T cells, can expand and persist for years after administration, it is desirable to include a safety mechanism to allow selective depletion of adoptively infused cells in the face of toxicity. The use of suicide modules allows for selective destruction of adoptively transferred cells and can be used to prevent or halt unacceptable toxicities caused by the therapy in question. In the presence of a molecule that binds to or otherwise reacts with a suicide module expressed on a cell surface, cell killing can occur, which can prevent further unwanted and harmful side effects of treatment. Thus, suicide modules enable selective deletion of the engineered cells in vivo.

Suicide genes encoding suicide proteins for use in suicide module constructs can be broadly classified based upon their mechanism of action. Some suicide genes are classified as genes that code for metabolic, small molecule-based modules, such as those that convert a prodrug into an active toxic agent, known as gene-directed enzyme prodrug therapy (GDEPT). Nonlimiting examples of such modules include herpes simplex virus thymidine kinase (HSV-tk)-derived systems. The tk gene is a cell cycle-dependent suicide gene that catalyzes the generation of triphosphate ganciclovir (GCV), which is toxic to proliferating cells by inhibiting DNA chain elongation. Other such systems are based on cytosine deaminase/5-fluorocytosine (CD/5-FC). Cytosine deaminase converts the prodrug 5-fluorocytosine to the active 5-fluorouracil, which in turn causes cell death.

Other types of suicide genes include genes that code for substances that dimerize and cause cell death in the presence of certain chemical agents. Nonlimiting examples include inducible FAS (iFAS) and inducible Caspase 9 (iCasp9) that dimerize in the presence of the chemical rimiducid or rimiducid analogues.

Another class of suicide genes includes genes coding for ligand receptors comprising ligand binding domains, e.g. epitopes, that can be bound by antibodies, such as, but not limited to, clinically approved antibodies that cause cell death by antibody-dependent cell-mediated cytotoxicity (ADCC) or complement-dependent cytotoxicity (CDC) after binding with the epitope. This class of genes includes, without limitation, genes encoding ligand binding domains from markers expressed on the cell surface, such as, but not limited to, CD20 or mimotopes of CD20 (see, e.g., Valton et al., *Scientific Reports* (2018) 8:8972). CD20 is a B cell membrane marker targeted by rituximab (Rituxan®, Genentech, South San Francisco, CA), a monoclonal antibody used to treat several disorders including chronic lymphocytic leukemia (CLL), non-Hodgkins lymphoma (NHL), rheumatoid arthritis (RA), granulomatosis with polyangititis (GPA), microscopic angitits (MPA), and pemphigus vulgaris (PV). Also useful are epitopes from CD19, a B cell membrane marker targeted by blinatumomab (Blincyto®, Amgen, Thousand Oaks, CA), used for acute lymphoblastic leukemia (ALL) treatment; epitopes from CD34 that can be bound by anti-CD34 antibodies, such as QBEND10 (ThermoFisher Scientific, Waltham, MA); as well as combinations of the above, such as RQR8 that contains target epitopes from both CD34 and CD20 (Philip et al., *Blood* (2014) 124:1277-1287). In the R2R8 construct, CD34 serves as a marker for selection and CD20 epitopes are bound by rituximab to induce ADCC and CDC. Also useful is a human EGFR-derived polypeptide, such as a truncated EGFR (huEGFRt) (Wang et al., *Blood* (2011) 118:1255-1263). EGFR-derived polypeptides can be recognized by cetuximab (Erbitux®, Eli Lilly and Company, Indianapolis, IN).

Genes encoding ligand binding domains derived from B cell maturation antigen (BCMA, also known as tumor necrosis factor (TNF) receptor superfamily member 17 (TNFRSF17)), will also find use in the present constructs. BCMA is a cell surface receptor expressed on the surface of mature B lymphocytes but not on T cells or monocytes. The BCMA protein includes an extracellular domain (ECD), a transmembrane region (TM), and an intracellular membrane domain (ICD). BCMA binds to two different ligands, termed BAFF and APRIL, which can be conjugated to a cytotoxin (an antibody-drug conjugate, ADC) that binds cells expressing a ligand binding domain from BCMA. For example, BCMA can be targeted by GSK2857916 (GlaxoSmithKline, Brentford, United Kingdom), a molecule including a humanized anti-BCMA monoclonal antibody conjugated to the cytotoxic agent monomethyl auristatin-F. Other anti-BCMA ADCs comprise MEDI2228 (MedImmune LLC, Gaithersburg, MD), AMG 224 (Amgen, Thousand Oaks, CA), and HDP-101 (Heidelberg-Pharma, Munich, Germany).

Thus, it is readily apparent that the suicide genes can code for the full-length molecules, fragments thereof comprising epitopes (e.g. ligand binding domains), and mimotopes thereof. The suicide gene products can be used in suicide modules as described herein.

Suicide protein modules for use with chimeric transmembrane proteins typically comprise at least one ligand binding domain, e.g., encoded by one or more of the suicide genes described above including, without limitation, a ligand binding domain from BCMA, CD19, truncated CD19, CD20, truncated CD20, RQR, truncated EGFR, mimotopes thereof, and combinations thereof. Suicide protein modules also include a transmembrane domain that anchors the ligand binding domain to the cell membrane. The ligand binding domain can bind the moiety that will confer ADCC, CDC, and/or ADC killing, such as an antibody or other cognate ligand. The suicide module can be designed as a Type I membrane protein with an N-terminal ECD, a Type II membrane protein with a C-terminal ICD, or a multi-spanning transmembrane protein. The TM can be either a TM associated with the ligand binding domain in nature or a heterologous TM or a chimeric TM. The chosen ligand binding domain can be fused to a CAR construct or a B2M/HLA-E fusion protein, described further herein, with or without linkers. Additionally, in some embodiments, the constructs include linker sequences, such as flexible linkers, to link various components. Linkers are typically short, repetitive amino acid sequences, generally rich in small or polar amino acids such as Gly and Ser, and can provide flexibility and solubility to the constructs. The length of the flexible linkers can be adjusted to allow for proper folding or to achieve optimal biological activity of the fusion proteins. Typical linkers include from approximately 3 to 25 amino acids. See, e.g., Chen et al., *Adv. Drug. Deliv. Rev.* (2013) 65:1357-1369, for a review of linkers for use in fusion proteins and Table 2 for exemplary linkers for use in the present constructs.

TABLE 2

Exemplary linkers

| SEQ ID NO: | Name | Sequence |
|---|---|---|
| SEQ ID NO: 15 | GSG linker | GSG |
| SEQ ID NO: 16 | GGS linker | GGS |
| SEQ ID NO: 17 | (G3S) linker | GGGS |
| SEQ ID NO: 18 | (G4S) linker | GGGGS |
| SEQ ID NO: 19 | (G5S) linker | GGGGGS |
| SEQ ID NO: 20 | (G3S) linker | GGGS |
| SEQ ID NO: 21 | (GGS)7 linker | GGSGGSGGSGGSGGSGGSGGS |
| SEQ ID NO: 22 | triple A linker | AAA |
| SEQ ID NO: 23 | (G3S)3 | GGGSGGGSGGGS |
| SEQ ID NO: 24 | (G4S)3 | GGGGSGGGGSGGGGS |
| SEQ ID NO: 25 | (G4S)4 | GGGGSGGGGSGGGGSGGGGS |
| SEQ ID NO: 26 | (G4S)5 | GGGGSGGGGSGGGGSGGGGSGGGGS |
| SEQ ID NO: 27 | XTEN | SGSETPGTSESATPES |

In one embodiment, the suicide protein modules are based on BCMA-derived molecules. As explained herein, the full-length BCMA protein includes an ECD, a TM, and an ICD. These domains can be used in suicide modules either in their entirety, or portions thereof comprising deletions or truncations, or variants thereof, which retain the desired biological activity, such as the ligand binding domain (in the case of the ECD) and the ability to anchor the ligand binding domain to the cell membrane (in the case of the TM). The module can also include, but need not include, a signal sequence. The BCMA can include the full-length amino acid sequence, such as the sequence of SEQ ID NO:1. Alternatively, the BCMA component can be shorter or longer. For example, the suicide module can include the ECD, such as residues 1-54 of BCMA (SEQ ID NO:3). The BCMA suicide module can include residues 1-77 of SEQ ID NO: 1, thus including the ECD and the TM, in order to anchor the protein in the membrane and allow for depletion. The BCMA suicide module can include the ECD, TM, and a truncated portion of the ICD, such as the ICD of SEQ ID NO:5 that has a deletion of amino acids 2-15 of the BCMA ICD. The BCMA suicide module can include a protein that retains amino acids 1-16 of the ICD, with a C-terminal deletion of the remainder of the ICD, such as the ICD sequence shown SEQ ID NO:6. The BCMA suicide module can include an ECD lacking amino acids 1-5 of the ECD, as shown in SEQ ID NO:7. The BCMA suicide module can include an ECD lacking amino acids 41-54 of the ECD, as shown in SEQ ID NO:8. The BCMA suicide module can include an ECD lacking amino acids 1-5 and 41-54, as shown in SEQ ID NO:9. Several other configurations of the BCMA suicide module can be readily envisioned. Table 3 provides representative components for use in the BCMA-based suicide modules.

TABLE 3

Exemplary sequences of BCMA components for use in BCMA-based suicide modules

| SEQ ID NO: | Structure |
|---|---|
| SEQ ID NO: 1 | Full-length BCMA (BCMA FL), including the ECD, TM, and ICD |
| SEQ ID NO: 5 | BCMA truncated ICD domain (ICD truncation I) |
| SEQ ID NO: 6 | BCMA truncated ICD domain (ICD truncation II) |
| SEQ ID NO: 3 | BCMA ECD domain |
| SEQ ID NO: 7 | BCMA ECD domain with N-terminal truncation |
| SEQ ID NO: 8 | BCMA ECD domain with C-terminal truncation |
| SEQ ID NO: 9 | BCMA ECD domain with N- and C-terminal truncations |

Thus, BCMA suicide modules can comprise at least one ligand binding domain and a transmembrane domain that anchors the ligand binding domain to the cell membrane. The ligand binding domain is found in the cysteine-rich portion of the ECD at approximately amino acids 6-41 of SEQ IN NO: 3 and can bind the moiety that will confer ADCC or ADC killing, such as an antibody or a cognate ligand, or an antibody conjugated to a toxin. The TM present in the BCMA-based suicide modules can be the native BCMA TM or a heterologous TM, for example, but not limited to, a TM from CD8, such as the CD8a TM (SEQ ID NO: 10) or the CD28 TM (SEQ ID NO:64), as well as, without limitation, the HLA-E TM, the IL-15R TM, the IL-15/IL-15R TM, the TACI TM, or the CD19 TM. In some embodiments, the BCMA constructs include linker sequences, e.g., between the ECD and the TM, or between other components of the BCMA constructs. Nonlimiting examples of linker sequences are shown in Table 2. In additional embodiments, the BCMA constructs can include cell surface glycoproteins, such as CD34 and/or CD8. CD34 can be used for cell sorting using an anti-CD34 antibody, such as QBEND10 (ThermoFisher Scientific, Waltham, MA) and CD8 can be used as an extra linker. Table 4 provides the fusion sequences of representative constructs comprising BCMA suicide modules.

TABLE 4

Exemplary suicide modules based on BCMA

| SEQ ID: NO: | Structure |
| --- | --- |
| SEQ ID NO: 1 | Full-length BCMA (BCMA FL), including the BCMA ECD, TM, and ICM |
| SEQ ID NO: 46 | BCMA including ECD, TM, and ICD truncated I |
| SEQ ID NO: 47 | BCMA including ECD, TM, and ICD truncated II |
| SEQ ID NO: 48 | BCMA ECD/CD8TM |
| SEQ ID NO: 49 | BCMA ECD/linker/CD8TM |
| SEQ ID NO: 50 | BCMA ECD/CD34/CD8TM |
| SEQ ID NO: 51 | BCMA ECD/CD34/CD8/CD8TM |

In some embodiments, one or more suicide modules, such as the BCMA-based suicide modules, can be included in a CAR construct, to produce a fusion protein that includes CAR components and the suicide module. The suicide module can be placed internally or can be located at the N- or C-terminus of the CAR cassette. A self-cleaving peptide between the suicide module and the remainder of the construct can be used to allow co-expression of the suicide module and the remainder of the construct within the target cell, followed by cleavage, such that these two components are expressed as separate proteins at the cell surface. For example, the fusion protein may comprise a self-cleaving 2A peptide, such as the foot-and-mouth disease 2A peptide.

FIG. 1A is a depiction of a representative CAR construct without a suicide module. CAR constructs typically include at least one extracellular single-chain variable fragment (scFv) from an antibody. The scFv is derived from the portion of the antibody that specifically recognizes a target protein and is expressed on the surface of a CAR-T cell to confer antigen specificity. The scFv component or ligand binding component can be any of the scFvs or ligand binding components shown in Table 1, as well as other scFvs and ligand binding components known in the art. The scFv can be joined to a hinge/spacer peptide that connects the extracellular targeting element to a transmembrane domain and affects CAR function and scFv flexibility. The transmembrane domain traverses the cell membrane, anchors the CAR to the cell surface, and connects the extracellular domain to the intracellular signaling domain, thus impacting expression of the CAR on the cell surface. The intracellular signaling domain mediates downstream signaling during T cell activation. When the extracellular ligand binding domain binds to a cognate ligand, the intracellular signaling domain of the CAR activates the lymphocyte. CAR-T cells combine the specificity of an antibody with the cytotoxic and memory functions of T cells. In FIGS. 1A to 1F, the "CAR signaling domain" refers to the combination of the hinge/spacer peptide, the transmembrane domain, and the intracellular T cell signaling domain.

Figure 2:
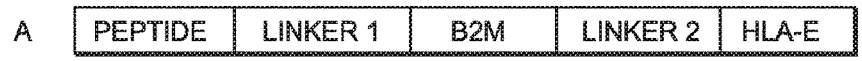
FIG. 2A illustrates a beta-2 microglobulin (B2M) and HLA class I histocompatibility antigen alpha chain E (HLA-E) fusion protein.
FIGS. 2B-2F illustrate exemplary B2M/HLA-E-based constructs comprising suicide modules (SM) of the present invention.
Figure 2:
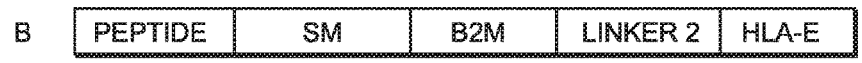
Figure 2:
Figure 2:
Figure 2:
Figure 2:

Exemplary CAR fusion proteins comprising suicide modules of the present invention (designated "SM" in FIGS. 1 and 2) and CAR components are shown in FIGS. 1B-1F and described in Table 5. As shown in FIG. 1D, the CAR constructs can include an scFv domain that is split in two parts (designated scFvD1 and scFvD2) that can be connected by a suicide module. Furthermore, CAR constructs can include CARs with more than one scFv domain or ligand binding domain (dual targeting), in order to target more than one protein. It is to be understood that the suicide modules present in the CAR fusions can be any of those described herein. It is also to be understood that the sequences for the CAR fusions as described herein are merely exemplary and additional CAR fusions comprising suicide modules can be designed and used.

TABLE 5

Exemplary CAR constructs that include suicide modules

| SEQ ID NO: | Structure |
| --- | --- |
| SEQ ID NO: 52 | scFv/SM/CAR signaling |
| SEQ ID NO: 53 | SM/scFv/CAR signaling |
| SEQ ID NO: 54 | scFvD1/SM/scFvD2/CAR signaling |
| SEQ ID NO: 55 | SM/scFv/SM/CAR signaling |
| SEQ ID NO: 56 | scFv/CAR signaling/2A peptide/SM |

In additional embodiments, the suicide module can be incorporated into fusion proteins that include beta-2 microglobulin (B2M) and human leukocyte antigen E (HLA-E) class I products. B2M is a protein subunit required for surface expression of polymorphic HLA class I heavy chains and the B2M/HLA class I complex is recognized by cytotoxic CD8+ T cells. In the case of donor-mismatched HLA class I molecules, the host cytotoxic CD8+ cells recognize the donor cells as foreign and thus kill the donor cells. Pluripotent stem cells (PSCs) have been developed that lack expression of B2M in order to eliminate class I surface expression and prevent the stimulation of host HLA class I mismatched cytotoxic CD8+ T cells. However, a major limitation of this strategy is that HLA class I-negative cells are lysed by natural killer (NK) cells because of the "missing self" response. Hence, B2M/HLA-E fusions have been developed for use in allogeneic cell therapies in order to prevent rejection of PSCs in allogeneic cell therapy recipients. It has been shown that when HLA-E genes are knocked into the B2M locus in stem cells, inducible, regulated, surface expression of HLA-E single-chain dimers (fused to B2M) or trimers (fused to B2M and a peptide antigen), without surface expression of HLA-A, B, or C, can be achieved. These HLA-engineered PSCs and their differentiated derivatives are not recognized as allogeneic by HLA class I mismatched CD8+ T cells, do not bind anti-HLA A, B, or C antibodies, and are resistant to NK-mediated lysis. See, e.g., Gornalusse et al., *Nat. Biotechnol.* (2017) 35:765-772.

Suicide modules, as described herein, can be combined with B2M/HLA-E constructs to be introduced into the B2M locus of T cells, stem cells, and the like, to prevent NK-mediated lysis leading to Host versus Graft rejection, and to simultaneously provide an integrated suicide module. The benefit of these suicide module fusions is twofold. The constructs can provide a kill switch for adoptively transferred cells when needed. Additionally, should the transformed cells lose or silence the cassettes, HLA-E expression at the cell surface will be lost automatically and the host or other donor NK cells will be able to kill these cells due to the loss of B2M/HLA-E and loss of all B2M/HLA class I expression. Furthermore, these constructs provide universal cassettes that can be used in combination with any CAR construct without further re-engineering the CAR.

Exemplary B2M/HLA-E fusions that include suicide modules of the present invention are depicted in FIGS. 2B-2F. FIG. 2A shows a representative B2M/HLA-E fusion that does not include a suicide module. The Example herein also describes the production of a B2M/HLA-E construct that can be used as a basis for incorporating a suicide module as described herein. The construct depicted in FIG. 2A can comprise, in 5' to 3' order, a signal sequence, such as the B2M signal sequence or a heterologous signal, fused to a peptide from the signal sequence of HLA-G (another HLA class I molecule), which is a nonpolymorphic peptide normally presented by HLA-E that inhibits NK cell-dependent lysis. The HLA-G peptide is a natural ligand of B2M/HLA-E that is presented to signal a healthy cell. The HLA-G component is termed "peptide" in FIGS. 2A-2F. This peptide (SEQ ID NO:36) is a shortened form of the full-length signal sequence (SEQ ID NO:35). Once the construct is expressed by the target cell, the signal sequence of B2M is cleaved, resulting in the mature polypeptide product. This peptide is adjacent to a first linker region (termed "linker1"). The linker is substantially linear and can be, but is not limited to, a linker set forth in Table 2. Linker1 links the HLA-G peptide to the B2M mature protein, which in turn is linked to a second linker (termed "linker2"), which can be the same or different than the first linker and links the B2M protein to the HLA-E heavy chain.

FIGS. 2B-2F show different configurations of the B2M/HLA-E protein fusions comprising suicide modules of the present invention. The suicide modules can be placed internally (as in FIGS. 2B-2D), or can be on the N-terminus (FIG. 2E) or the C-terminus (FIG. 2F). More than one suicide module can be present. If the suicide module is located at the N- or C-terminus, a self-cleaving peptide located between the suicide module and the remainder of the construct can be used to allow co-expression of the suicide module and the rest of the construct within the target cell, followed by cleavage, such that these two components are expressed as separate proteins at the cell surface. As explained herein, the self-cleaving peptide can be a 2A peptide. One or more linkers can also be present, such as two linkers, located on either side of the B2M component.

Table 6 provides exemplary B2M/HLA-E fusions that include suicide modules. It is to be understood that the suicide modules present in these fusions can be any of those described herein. It is also to be understood that the sequences for the fusions as described herein are merely exemplary and additional B2M/HLA-E fusions comprising suicide modules can be designed and used in the present constructs and methods.

TABLE 6

Exemplary B2M/HLA-E suicide module fusions

| SEQ ID NO: | Structure |
| --- | --- |
| SEQ ID NO: 59 | HLA-G/SM/B2M/linker2/HLA-E |
| SEQ ID NO: 60 | HLA-G/linker1/B2M/SM/HLA-E |
| SEQ ID NO: 61 | HLA-G/SM/B2M/SM/HLA-E |
| SEQ ID NO: 62 | SM/linker1/B2M/linker2/HLA-E |
| SEQ ID NO: 63 | HLA-G/linker1/B2M/linker2/HLA-E/2A/SM |

Using the constructs described herein, ligand binding domains can be presented on adoptive cell membranes, and antibodies that target these domains can be designed that cause ADCC, CDC or ADC killing. In the case of ADC, an antibody conjugate can be used that includes a biologically active, cytotoxic drug. The antibody portion of the conjugate interacts with the ligand binding domain. The biochemical reaction between the antibody and the ligand binding domain triggers a signal in the adoptive cell, which then internalizes the antibody together with the cytotoxin. After the ADC is internalized, the cytotoxic drug is released and kills the cell.

Examples of cytotoxins for use with antibodies, include, without limitation, monomethyl auristatin-F, auristatin-E, calicheamicin-based drugs, and emtansine (DM-1).

Polynucleotides encoding the suicide module-containing protein constructs described herein can be designed and vectors comprising expression cassettes can be used to transform adoptive cells as described herein.

The polynucleotides can be RNA, such as mRNA, or single- or double-stranded DNA. The polynucleotides encode the fusion proteins described herein, and thus comprise coding sequences for the various components in the suicide module-containing constructs. As explained herein, polynucleotides can also comprise other sequences, such as sequences coding for linkers and signal sequences. The polynucleotides coding for the components of the fusions can be ligated to form a coding sequence for the fusion proteins using standard molecular biology techniques. The polynucleotide sequences can be codon-optimized for expression in mammalian cells. Optimized DNA sequences can be determined using commercially available computer programs and polynucleotides comprising the optimized sequences can be synthesized using well known techniques. Optimized sequences can be procured from commercial manufacturers.

The polynucleotide sequences can then be cloned into an expression vector and used to transform mammalian host cells. A large number of expression vectors suitable for use in transforming mammalian host cells are commercially available. Additionally, general methods for construction of expression vectors are known in the art. Several commercial software products are available that facilitate selection of appropriate vectors and construction thereof, such as vectors for mammalian cell transformation and gene expression in mammalian cells.

Vectors derived from mammalian viruses can be used for expressing the polynucleotides described herein in mammalian cells. These include vectors derived from viruses such as adenovirus, adeno-associated virus (AAV), papovirus, herpesvirus, polyomavirus, cytomegalovirus, lentivirus, retrovirus, vaccinia and Simian Virus 40 (SV40) (see, e.g., Kaufman, R. J., *Molecular Biotechnology* (2000) 16:151-160; and Cooray et al., *Methods Enzymol.* (2012) 507:29-57). Regulatory sequences operably linked to the components can include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like. Viral vectors typically include constitutive or inducible promoters, such as, but not limited to, CMV, EFla, SV40, PGKI (mouse or human), MND, Ubc, CAG, CaMKIIa, and beta-Act. See, e.g., Khan, K. H., *Advanced Pharmaceutical Bulletin* (2013) 3:257-263. Furthermore, mammalian RNA polymerase III promoters, including H1 and U6, can be used. Additionally, a terminator, such as, but not limited to, WPRN, or a PolyA sequence, such as, but not limited to, an SV40 sequence, or a BGH sequence, can be present. Additionally, multicistronic constructs, such as described herein, that include multiple coding sequences may be designed to use only one promoter by including an internal ribosome entry site (IRES) element, or sequences coding for a 2A self-cleaving peptide, and the like Alternatively, mRNA can be produced by a commercial manufacturer from a DNA vector containing a promoter and a terminator module. In another embodiment, the polynucleotide sequences described herein can be cloned into a transposon, such as, the Sleeping Beauty transposon system (Kebriaei et al., *Trends in Genetics* (2017) 33:852-870), or the PiggyBac transposon system (Woodard et al., *Trends in Biotechnology* (2015) 33:525-533).

The virus, the mRNA, or the transposon/transposase construct can then be introduced into mammalian cells using transduction methods, such as, but not limited to, spinoculation for the virus, or lipofection and nucleofection for the DNA. Stem cells or lymphocytes, such as peripheral blood mononuclear cells (PBMCs), can be purchased from commercial vendors. Alternatively, lymphocytes, such as PBMCs, can be isolated as described further herein. The cells can be transduced with virus at different titers (MOI, multiplicity of infection), depending on the cell type. Typical titers can be up to $1\times10^5$ and $1\times10^6$, $1\times10^7$, and higher.

For example, CARs, such as CARs coding for suicide modules and CAR components, can be inserted into lymphocytes, such as T cells, using standard recombinant DNA technology, gene therapy techniques, mRNA transfection, the Sleeping Beauty transposon system (Kebriaei et al., *Trends in Genetics* (2017) 33:852-870), the PiggyBac transposon system (Woodard et al., *Trends in Biotechnology* (2015) 33:525-533), as well as gene editing methods that utilize programmable nucleases that enable targeted genetic modifications in a host cell genome by creating site-specific breaks at desired locations. Such nucleases include, but are not limited to, Clustered Regularly Interspaced Short Palindromic Repeats (CRISPR)-associated nucleases, zinc-finger nucleases (ZFNs), transcription activator-like effector nucleases (TALENs), and meganucleases. For reviews of these programmable nucleases see, e.g., Kim et al., *Nature Reviews Genetics* (2014) 15:321-334 (for reviews of all of the above nucleases); Koonin et al., *Curr Opin Microbiol.* (2017) 37:67-78; Makarova et al., *Cell* (2017) 168:146; Makarova et al., *Cell* (2017) 168:328; Hsu et al., *Cell* (2014) 157:1262-1278; Jore, et al., *Nature Struc. and Molec. Biol.* (2011) 18:529-536 (for reviews of CRISPR-associated nucleases); Urnov et al., *Nature Reviews Genetics* (2010) 11:636-646 (for a review of ZFNs); Stoddard, B., Mobile DNA (2014) 5:7 (for a review of meganucleases); Joung et al., *Nature Reviews Molecular Cell Biology* (2013) 14:49-55 (for a review of TALENs).

Typically lymphocytes, such as T cells, are incubated with a viral vector, such as a recombinant adeno-associated virus (AAV) vector, an adenoviral vector, a lentiviral vector, a retroviral vector, or the like, that encodes the desired expression cassette, such as a B2M/HLA-E cassette, or a CAR expression cassette (see, e.g., Levine et al., *Mol. Therapy—Meth. Clin. Develop.* (2017) 4:92-101; Wang et al., *Mol. Therapy—Oncolytics* (2016) 3:16015; Smith et al., *J. Cell Immunother.* (2016) 2:59-68; Maude et al., *N. Engl. J. Med.* (2014) 371:1507-1517; U.S. Pat. Nos. 7,446,190 and 8,399,645, each of which is incorporated herein in its entirety). The inserted genetic material can be integrated into the genome of the patient cells or donor cells and then expressed in the cell or on the cell surface.

Transduced and transfected cells can be tested for transgene expression using methods well known in the art, such as high-throughput screening techniques including, but not limited to, fluorescence-activated cell sorting (FACS)-based screening platforms, microfluidics-based screening platforms, ELISAs, and the like. These techniques are well known and reviewed in, for example, Wojcik et al., *Int. J. Molec. Sci.* (2015) 16:24918-24945. Western Blot techniques can also be used. For example, BCMA suicide gene-transduced CAR-T cells can be tested for CAR19 expression and BCMA expression using fluorescently labelled anti-CAR19 and anti-BCMA antibodies (such as from Biolegend, San Diego, CA; or Abcam, Cambridge, MA). ADCC-based killing can be tested with an NK cell-based killing assay. Briefly, NK cells can be isolated from PBMCs and cultured in NK cell media. CAR-T cells transduced with a BCMA suicide module can be cultured in T cell media. For the killing assay, effector NK cells and target CAR-T cells can be fluorescently stained and then mixed at different ratios (1:10, 1:5, 1:4, 1:3, 1:2, 1:1, 2:1, 3:1, 4:1, 5:1 and 10:1) and an ADCC-inducing antibody can be added, such as GSK2857916 (GlaxoSmithKline, Brentford, United Kingdom). The cells can be incubated for approximately 1, 2, 3, 4, 5 or more, such as up to 24 hours, and then imaged or counted for dead/live cells and the ratios tallied. ADC-based killing can be assessed in a similar killing assay comprising the target cells and the ADC-inducing antibody drug conjugate as described herein.

Adoptive cells that can be genetically engineered to produce suicide-containing modules include, but are not limited to, lymphocytes, such as, but not limited to, CAR-T cells, T cells, TILS, NK cells, CAR-NK cells, and dendritic cells; stem cells, such as, but not limited to induced pluripotent stem cells (iPSCs), cord blood stem cells, and hematopoietic stem cells; macrophages; red blood cells; fibroblasts; endothelial cells; epithelial cells; and pancreatic precursor cells. Cells for use herein can be isolated from a subject, such as a human subject, using standard techniques.

For example, lymphocytes for use herein can be isolated from a subject, for example, from blood, or from solid tumors in the case of TILs, or from lymphoid organs such as the thymus, bone marrow, lymph nodes, and mucosal-associated lymphoid tissues. Techniques for isolating lymphocytes are well known in the art. For example, peripheral blood mononuclear cells (PBMCs) can be isolated from a patient or donor using leukapheresis, a process where blood is removed from the subject, leukocytes are separated, and the remainder of the blood is returned to the circulation, using methods well known in the art (see, e.g., Smith, J. W. *Ther. Apher.* (1997) 1:203-206).

PBMCs can also be separated from whole blood using, for example, ficoll, a hydrophilic polysaccharide that separates layers of blood, and density gradient centrifugation. Generally, anticoagulant or defibrinated blood specimens are layered on top of a ficoll solution, and centrifuged to form different layers of cells. The bottom layer includes red blood cells (erythrocytes), which are collected or aggregated by the ficoll medium and sink completely through to the bottom. The next layer contains primarily granulocytes, which also migrate down through the ficoll-paque solution. The next layer includes lymphocytes, which are typically at the interface between the plasma and the ficoll solution, along with monocytes and platelets. To isolate the lymphocytes, this layer is recovered, washed with a salt solution to remove platelets, ficoll and plasma, and then centrifuged again.

Other techniques for isolating lymphocytes include biopanning, which isolates cell populations from solution by binding cells of interest to antibody-coated plastic surfaces. Unwanted cells are then removed by treatment with specific antibody and complement. Additionally, fluorescence activated cell sorter (FACS) analysis can be used to detect and count lymphocytes. FACS analysis uses a flow cytometer that separates labelled cells based on differences in light scattering and fluorescence.

For TILs, lymphocytes are isolated from a tumor and grown, for example, in high-dose IL-2 and selected using cytokine release coculture assays against either autologous tumor or HLA-matched tumor cell lines. Cultures with evidence of increased specific reactivity compared to allogeneic nonMHC-matched controls can be selected for rapid expansion and then introduced into a subject in order to treat cancer. See, e.g., Rosenberg et al., *Clin. Cancer Res.* (2011)

17:4550-4557; Dudly et al., *Science* (2002) 298:850-854; Dudly et al., *J. Clin. Oncol.* (2008) 26:5233-5239; Dudley et al., *J. Immnother.* (2003) 26:332-342.

Upon isolation, lymphocytes can be characterized in terms of specificity, frequency, and function. Frequently used assays include an ELISPOT assay, which measures the frequency of T cell response. The product can be enriched with specific subsets of T cells, such as CD4+, CD8+, CD25+, or CD62L+ T cells using techniques known in the art. See, e.g., Wang et al., *Mol. Therapy—Oncolytics* (2016) 3:16015.

After isolation, lymphocytes can be activated using techniques well known in the art in order to promote proliferation and differentiation into specialized lymphocytes. For example, T cells can be activated using several methods, including the use of commercially available soluble CD3/28 activators, or magnetic beads coated with anti-CD3/anti-CD28 monoclonal antibodies. The beads can be easily removed from the culture through magnetic separation using techniques known in the art (see, e.g., Levine, B. L., *BioProcessing J.* (2007) 6:14-19). In certain embodiments herein, surface markers for activated T cells include, for example, CD3, CD4, CD8, PD1, IL2R, and others. Activated cytotoxic lymphocytes can kill target cells after binding cognate receptors on the surface of target cells. Surface markers for NK cells include, for example, CD16, CD56, and others.

Before, after, or during activation, lymphocytes can be genetically engineered to produce one or more constructs that contain suicide modules on the cell surface, such as BCMA-derived constructs and/or the suicide module-containing B2M/HLA-E constructs. Additionally, cells can be transformed with constructs encoding one or more chimeric antigen receptors (CARs) on the cell surface, thereby reprogramming the lymphocytes to target tumor cells. In some embodiments, the suicide modules are incorporated into the CAR constructs. In other embodiments, the suicide module constructs are used to transform lymphocytes independently of the CAR constructs. CAR-modified lymphocytes, such as CAR-T cells, recognize specific soluble antigens or antigens on a target cell surface, such as a tumor cell surface, or on cells in the tumor microenvironment. Representative cell targets, as well as their cognate CARs, are shown in Table 1. CARs can be incorporated into T cells, TILs, NK cells, or TCRs resulting in CAR-T cells, CAR-TILs, CAR-NK cells, or TCR engineered CAR-T cells, respectively, for use in adoptive T cell immunotherapies.

The CARs, or CARs and separate constructs including the suicide modules, can be introduced into lymphocytes, such as T cells, using methods well known in the art and described herein.

Once the editing methods are performed, cells are screened to select for cells with desired genomic modifications, using methods well known in the art, such as high-throughput screening techniques including, but not limited to, fluorescence-activated cell sorting (FACS)-based screening platforms, microfluidics-based screening platforms, and the like. These techniques are well known and reviewed in, for example, Wojcik et al., *Int. J. Molec. Sci.* (2015) 16:24918-24945.

After isolation, activation and optionally editing, the lymphocytes can be expanded in a selected culture medium, such as but not limited to, Immunocult™ medium (Stemcell Technologies, Vancouver, Canada); Complete RPMI 1640™ medium (Gibco, ThermoFisher Scientific, Waltham, MA); TexMACS™ medium (Miltenyi Biotec, Bergisch Gladbach, Germany); X-Vivo-15™ medium (Lonza, Basel, Switzerland); CTS Optimizer™ medium (Gibco, ThermoFisher Scientific, Waltham, MA). The culture medium can be supplemented with human serum albumin, or with a human serum replacement, such as CTS™ Immune Cell SR serum replacement (Gibco, ThermoFisher Scientific, Waltham, MA), or KnockOut™ SR serum replacement (Gibco, ThermoFisher Scientific, Waltham, MA). The serum or serum replacement will typically be present at 0.5% to 15%, such as 2% to 15%, 3% to 12%, for example, 5% to 10%, or any percentage between 2% to 15%.

The medium can also optionally contain cytokines, such as but not limited to, IL-2, IL-7, and/or IL-15. Other cytokines can also be present, such as IL-22 and/or IL-18. The cell culture medium can further be supplemented with glycolysis inhibitors such as 2-deoxyglucose and antibiotics.

Lymphocyte populations produced using the culturing techniques described herein can be used to prevent GvHD, Host versus Graft rejection, and other cell toxicities caused by the treatment of various types of cancers using adoptive cell therapies, such as, but not limited to cytokine release syndrome (CRS), cytokine storm, neurotoxicity, and oncogenic transformations of the graft. Such cancers include, without limitation, prostate cancers; ovarian cancers; cervical cancers; colorectal cancers; intestinal cancers; testicular cancers; skin cancers; lung cancers; thyroid cancers; bone cancers; breast cancers; bladder cancers; uterine cancers; vaginal cancers; pancreatic cancers; liver cancers; kidney cancers; brain cancers; spinal cord cancers; oral cancers; parotid tumors; blood cancers; lymphomas, such as B cell lymphomas; leukemias; solid tumors; liquid tumors; and the like.

In other embodiments, suicide module-containing constructs can be delivered to patients being treat for other cell proliferative disorders, including precancerous conditions; hematologic disorders; and immune disorders, such as autoimmune disorders including, without limitation, Addison's disease, celiac disease, diabetes mellitus type 1, Grave's disease, Hashimoto's disease, inflammatory bowel disease, multiple sclerosis, psoriasis, rheumatoid arthritis, scleroderma, and systemic lupus erythematosus.

Once produced, the lymphocytes, such as T cells, including without limitation, CAR-T cells, produced as described herein, can be formulated into compositions for delivery to the subject to be treated. The compositions include the lymphocytes, and one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition can also include an antimicrobial agent for preventing or deterring microbial growth. Nonlimiting examples of antimicrobial agents suitable for use include benzalkonium chloride, benzethonium chloride, benzyl alcohol, cetylpyridinium chloride, chlorobutanol, phenol, phenylethyl alcohol, phenylmercuric nitrate, thimerosal, and combinations thereof.

An antioxidant can also be present in the composition. Antioxidants are used to prevent oxidation, thereby preventing the deterioration of the lymphocytes or other components of the preparation. Suitable antioxidants for use include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as TWEEN 20 and TWEEN 80, and pluronics such as F68 and F88 (BASF, Mount Olive, NJ); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of cells, such as lymphocytes, in the composition will vary depending on a number of factors, but will optimally be a therapeutically effective dose when the composition is in a unit dosage form or container (for example, a vial). A therapeutically effective dose can be determined experimentally by repeated administration of increasing amounts of the composition in order to determine which amount produces a clinically desired endpoint. Representative therapeutically effective doses are described herein.

The amount of any individual excipient in the composition will vary depending on the nature and function of the excipient and particular needs of the composition. Typically, the optimal amount of any individual excipient is determined through routine experimentation, by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy," Current edition, Williams & Williams, the "Physician's Desk Reference," Current edition, Medical Economics, Montvale, N J, and Kibbe, A. H., Handbook of Pharmaceutical Excipients, Current edition, American Pharmaceutical Association, Washington, D.C.

In one embodiment, the composition will include T cells in a solution that includes media and a freezing agent such as, but not limited to, 3% to 12% dimethylsulfoxide (DMSO), for example, 4% to 10% DMSO, such as, 5% . . . 5.5% . . . 6% . . . 6.5% . . . 7% . . . 7.5% . . . 8% . . . 8.5% . . . 9% . . . 9.5% . . . 10%, or any integer within these ranges; human albumin, such as 1% to 5% albumin, for example, 2% to 3% albumin, or any percentage within these ranges. The composition can also be in the form of a cryopreserved injectable, such as containing PLASMA-LYTE ATM (Multiple Electrolytes Injection, Type 1, USP; Baxter, Deerfield, IL); dextrose in NaCl; Dextran 40 in dextrose; human serum albumin (HSA); CRYOSERV™ DMSO (Merit Pharmaceutical, Los Angeles, CA); and/or or CryoStor™ products, such as CryoStor CS5™ and CrysoStor CS10™ (both from Stemcell Technologies, Vancouver, Canada). T cells will be present in a therapeutically effective amount, such as an amount that delivers $1\times10^4$ to $1\times10^{10}$ cells per kg/bodyweight, such as $0.5\times10^6$ to $6\times10^8$ cells per kg, or any number within these ranges.

The pharmaceutical preparations can be housed in a single infusion bag for intravenous infusion, syringe, an implantation device, or the like, depending upon the intended mode of delivery and use. Preferably, the amount of the composition present is appropriate for a single dose, in a premeasured or pre-packaged form.

The compositions herein may optionally include one or more additional agents, such as other medications used to treat a subject for the disease, such as the cancer in question, or to treat known side effects from the treatment. For example, T cells release cytokines into the bloodstream, which can lead to dangerously high fevers and precipitous drops in blood pressure. This condition is known as cytokine release syndrome (CRS). In many patients, CRS can be managed with standard supportive therapies, including steroids and immunotherapies, such as tocilizumab (Actemra®, Genentech, South San Francisco, CA) that block IL-6 activity.

At least one therapeutically effective cycle of treatment with a lymphocyte composition will be administered to a subject. By "therapeutically effective cycle of treatment" is intended a cycle of treatment that, when administered, brings about a positive therapeutic response with respect to preventing or treating a cell toxicity, such as GvHD, associated with the treatment of an individual for the diseases described herein. By "positive therapeutic response" is intended that the individual undergoing treatment exhibits an improvement in cell toxicities associated with an adoptive cell therapy.

In certain embodiments, multiple therapeutically effective doses of compositions comprising lymphocytes or other medications will be administered. The compositions are typically, although not necessarily, administered via injection, such as subcutaneously, intradermally, intravenously, intraarterially, intramuscularly, intraperitoneally, intramedullary, intratumorally, intranodally); by infusion; or locally. The pharmaceutical preparation can be in the form of a liquid solution or suspension immediately prior to administration. The foregoing is meant to be exemplary, as additional modes of administration are also contemplated. The pharmaceutical compositions may be administered using the same or different routes of administration in accordance with any medically acceptable method known in the art.

The actual dose to be administered will vary depending upon the age, weight, and general condition of the subject as well as the severity of the condition being treated, the judgment of the health care professional, and particular lymphocytes being administered. For example, if CAR-Ts are administered, the dosage will depend on the number of CAR-positive viable T cells. Therapeutically effective amounts can be determined by those skilled in the art, and will be adjusted to the particular requirements of each particular case.

Generally, a therapeutically effective amount of lymphocytes will range from a total of about $1 \times 10^5$ to about $1 \times 10^{10}$ lymphocytes or more per patient, such as $1 \times 10^6$ to about $1 \times 10^{10}$, for example, $1 \times 10^7$ to $1 \times 10^9$, such as $5 \times 10^7$ to $5 \times 10^8$, or any amount within these ranges. For example, if CAR-T cells are delivered, dosage ranges can be $1 \times 10^4$ to $1 \times 10^{10}$ CAR-T positive viable T cells per kg/bodyweight, such as $0.1 \times 10^6$ to $6 \times 10^8$, such as $2 \times 10^6$ to $2 \times 10^8$ Car-T-positive cells per kg, or any number within these ranges. The total number of cells, such as lymphocytes, can be administered in a single bolus dose, or can be administered in two or more doses, such as one or more days apart, such as in a cell suspension for infusion. The amount of compound administered will depend on the potency of the specific composition, the disease being treated, and the route of administration.

Additionally, the doses can comprise a mixture of lymphocytes, such as a mix of CD8+ and CD4+ cells. If a mix of CD8+ and CD4+ cells is provided, the ratio of CD8+ to CD4+ cells can be for example, 1:1, 1:2 or 2:1, 1:3 or 3:1, 1:4 or 4:1, 1:5 or 5:1, and the like.

The cells can be administered prior to, concurrent with, or subsequent to other agents. If provided at the same time as other agents, the cells can be provided in the same or in a different composition. Thus, the cells and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising cells and a dose of a pharmaceutical composition comprising at least one other agent, such as another chemotherapeutic agent, which in combination comprises a therapeutically effective dose, according to a particular dosing regimen. Similarly, lymphocytes and therapeutic agents can be administered in at least one therapeutic dose. Administration of the separate pharmaceutical compositions can be performed simultaneously or at different times (for example, sequentially, in either order, on the same day, or on different days), as long as the therapeutic effect of the combination of these substances is caused in the subject undergoing therapy.

Also provided are kits. In certain embodiments, the kits comprise one or more containers, comprising engineered lymphocytes as described herein, or compositions comprising the lymphocytes. The containers may be unit doses, such as infusion bags containing the lymphocytes, bulk packages (for example, multi-dose packages), or subunit doses.

The kits may comprise the components in any convenient, appropriate packaging. For example, ampules with nonresilient, removable closures (for example, sealed glass) or resilient stoppers are most conveniently used for liquid formulations. If the lymphocytes or compositions are provided as a dry formulation (for example, freeze dried or a dry powder), a vial with a resilient stopper is normally used, so that the compositions may be easily resuspended by injecting fluid through the resilient stopper. Also contemplated are packages for use in combination with a specific device, such as a syringe or an infusion device such as a mini-pump, an inhaler, and a nasal administration device (for example, an atomizer).

The kits may further comprise a suitable set of instructions relating to the use of the lymphocytes and compositions for any of the methods described herein. The instructions generally include information as to dosage, dosing schedule, and route of administration for the intended method of use. Instructions supplied in the kits can be written instructions on a label or package insert (for example, a paper sheet included in the kit), or machine-readable instructions (for example, instructions carried in an electronic form).

While preferred embodiments of the present invention have been shown and described herein, it will be obvious to those skilled in the art that such embodiments are provided by way of example only. From the above description and the following Example, one skilled in the art can ascertain essential characteristics of the present invention and, without departing from the spirit and scope thereof, can make changes, substitutions, variations, and modifications of the present invention to adapt it to various usages and conditions. Such changes, substitutions, variations, and modifications are also intended to fall within the scope of the present disclosure.

EXPERIMENTAL

Aspects of the present invention are further illustrated in the following Example. Efforts have been made to ensure accuracy with respect to numbers used (e.g., amounts, concentrations, percent changes, and the like) but some experimental errors and deviations should be accounted for. Unless indicated otherwise, temperature is in degrees Centigrade and pressure is at or near atmospheric. It should be understood that this Example, while indicating some embodiments of the present invention, is given by way of illustration only and is not intended to limit the scope of the present invention.

Example 1

Design, Cloning, Viral Vector Production, and T Cell Transduction of a B2M/HLA-E Insertion Cassette This Example illustrates in silico design and cloning of a B2M/HLA-E cassette and introduction into the B2M locus of T cells. Not all of the following steps are required nor must the order of the steps be as presented.

In Silico Design and Cloning

The B2M/HLA-E fusion protein was constructed as described in Gornalusse et al., *Nat. Biotechnol.* (2017) 35:765-772. Briefly, the amino acid sequence of the B2M/HLA-E fusion protein construct comprised a B2M signal sequence linked to the HLA-G signal sequence, linked to a linker region, linked to the B2M mature protein, linked to a second linker region, and linked to the HLA-E heavy chain. The amino acid sequence of the B2M/HLA-E fusion protein is shown in SEQ ID NO:57.

The fusion protein amino acid sequence was translated into DNA and the nucleotide sequence was codon-optimized for expression in mammalian cells using the IDT codon optimizer tool (Integrated DNA Technologies, Inc., Coralville, IA). The oligonucleotide sequence coding for the B2M/HLA-E fusion protein (SEQ ID NO:65) was provided to a commercial manufacturer for synthesis.

The nucleotide sequence was cloned into an adeno-associated virus type 6 (AAV6) vector. AAV6 and other AAV viruses (such as AAV2 and AAV9) can be engineered to deliver DNA donor elements to mammalian cells. If the AAV delivery is combined with a genomic cleavage event and the DNA donor element in the AAV is flanked by homology arms, the DNA donor element can be seamlessly inserted into the genomic cut site by homology-directed repair (HDR), as described in Eyquem et al., Nature (2017) 543:113-117.

In order to site-specifically insert the B2M/HLA-E nucleotide sequence into the host cell genome after site specific cleavage with a programmable nuclease such as Cas9, a target site in the B2M gene was chosen (motif location: chr15: 44711542-44711564 in hg38). Target sites and guides to deliver programmable nucleases such as Cas9 are readily determined using techniques such as those described in U.S. Pat. Nos. 9,580,701; 9,650,617; 9,688,972; 9,771,601; and 9,868,962, each of which is incorporated herein by reference in its entirety. 500 base pair (bp) homology arms, 5' and 3' of the cut site, were identified (SEQ ID NOS: 66 and 67). To construct the AAV6 insertion cassette, the mammalian promoter sequence EFlalpha was inserted upstream of the B2M/HLA-E nucleotide sequence (termed "donor element"). The homology arm nucleotide sequences were then added 5' and 3' of the reversed donor element and cloned into the AAV6 vector backbone.

Recombinant AAV Production

Recombinant AAV (rAAV) production has been described in detail elsewhere (see, e.g., Halbert et. al., Methods. Mol. Biol. (2018) 1687:257-266; Naso et. al., BioDrugs (2017) 31:317-334). Briefly, HEK 293T cells for rAAV production were obtained from the American Type Culture Collection (ATCC, CRL-11268™; Manassas, VA). On the first day, HEK 293 T cells were plated at $4 \times 10^5$ cells/ml on tissue culture-coated 15 cm plates in 20 ml complete growth media (DMEM supplemented with 10% fetal bovine serum and 1× penicillin streptomycin) and grown at 37° C. at 5% $CO_2$, in an incubator. Cells from 6×15 cm plates were used per experiment. On the second day, the cells were transfected with the B2M/HLA-E-rAAV vector for rAAV production using calcium phosphate transfection.

Per 15 cm plate, a transfection 856 μl water, 124 μl 2M $CaCl_2$) and 20 μg total vector DNA (for AAV production the 3 plasmids were combined at 1:1:1 ratio, pHelper, pAAV-RC6 and pAAV-B2M/HLA-E, 6.7 μg each) were mixed by vortexing. 1 ml of HBS was then added slowly. 2 ml of transfection mix was added dropwise to the 15 cm plate of HEK 293T cells and the mix was distributed gently across the plate and grown at 37° C., 5% $CO_2$ in an incubator. On the third day, the supernatant was removed from the cells and 20 ml of fresh complete media was added.

60-72 hours post-transfection, cells were washed with gradient buffer (100 mM Tris. pH 7.6; 500 mM NaCl; 100 mM $MgCl_2$). 0.5 ml gradient buffer was then added to each plate and cells were gently harvested and pooled in a 50 mL plastic tube. Cells were then lysed using 4 freeze/thaw cycles. Briefly, the cells were frozen using liquid nitrogen for 10 minutes. Cells were thawed at 55° C. in a water bath and then triturated through a syringe needle to aid cell lysis using a 20 ml syringe and a 23-gauge needle. The lysed cell suspension was then returned to 37° C. Benzonase (Sigma Aldrich, St Louis, MO) was added at 1 μl per 5 ml and the cell suspension was incubated at 37° C. for 45 minutes. The cell suspension was then centrifuged at 3700 rpm for 15 minutes at 4° C. using a Beckman rotor HS4.7™ (Beckman Coulter, Brea, CA). The supernatant containing the viral particles was collected in a 50 ml plastic tube. The supernatant was then layered on top of a 15%/25%/40%/58% gradient (top to bottom) of iodixanol (Optiprep™, NaCl, gradient buffer and phenol red) (Optiprep, Axis-Shield, Dundee, United Kingdom). The virus supernatant was centrifuged in the sealed tube through the iodixanol gradient using a Beckman 70Ti fixed angle Rotor™ (Beckman Coulter, Brea, CA) at 48,000 rpm for 2 hours and 10 minutes. The purified virus was removed from the tube with a syringe and needle.

The virus was further purified from the iodixanol by gravity flow size exclusion chromatography. The viral solution was run through a Sepharose G100 column (Sephadex G-100 Superfine; GE Healthcare, Pittsburgh, PA), pre-equilibrated with gradient buffer, and the virus was collected in 1 ml fractions. Fractions were tested for virus-containing fractions by measuring the absorbance at 260 nm and 280 nm with a UV spectrometer (Nanodrop, Thermofisher, Waltham, MA). Virus-containing fractions with a low absorption at 260 nm were pooled together. Fractions were concentrated using a Vivaspin 15R™ 30 kDa cut off concentrator (Vivaspin, Sartorius, 37079. Gottingen, Germany). Titering of the B2M/HLA-E-rAAV Viral titer was assessed using the Takara qPCR kit (Takara, Mountain View, CA) following the manufacturer's instructions.

Cas9 Preparation

Over-expression and purification of Streptococcus pyogenes CRISPR Cas9 (SpyCas9) protein from bacterial expression vectors, expression in Escherichia coli (BL21 (DE3)), and purification using affinity chromatography, ion exchange, and size exclusion chromatography, has been described elsewhere in detail. See, e.g., Jinek, et al., Science (2012) 337:816-821. SpyCas9 was produced as described in U.S. Pat. Nos. 9,580,701; 9,650,617; 9,688,972; 9,771,601; and 9,868,962, each of which is incorporated herein by reference in its entirety. Oligonucleotides were purchased from a commercial manufacturer. Cas9-ribonucleoprotein complexes (Cas9-RNPs) were formed as described in the references above.

T Cell Transduction with B2M/HLA-E-rAAV

Pan-T cells were prepared from donor PBMCs as follows. Briefly, approximately 350 million donor PBMCs were obtained from AllCells (Alameda, CA). The PBMCs were small aliquots from an AllCells Apheresis Leuko Pak™, collected using the Spectra Optia™ Apheresis System (TERUMO BCT, INC., Lakewood, CO 80215). Approximately 90% of these cells were mononuclear cells (MNCs).

The fresh MNC products were processed to deplete red blood cells (RBCs) using an ammonium chloride solution and were processed to deplete platelets by centrifugation. PBMCs were enumerated using acetic acid with methylene blue and a hemocytometer (Countess II FL Automated Cell Counter™; ThermoFisher Scientific, Waltham, MA). Pan-T cells were then purified using the Robosep™ cell separation robot (Stemcell Technologies, Vancouver, Canada) and the EasySep™ pan human T cell isolation kit (Stemcell Technologies, Vancouver, Canada), following the manufacturers' instructions. T cells were then cultured in Immunocult™ medium (Stemcell Technologies, Vancouver, Canada), supplemented with 5% fetal bovine serum (FBS) and 200 U/ml of recombinant human interleukin-2 (rhIL-2).

Cells were activated using anti-CD3/anti-CD28 Gibco Dynabeads™ (ThermoFisher Scientific, Waltham, MA) at 37° C., 5% $CO_2$ in an incubator. After 48 hours, the beads were removed with a magnet and the cells expanded for 24 hours in complete Immunocult™ medium (Stemcell Technologies, Vancouver, Canada), supplemented with 5% FBS and 200 U/ml of rhIL-2.

Nucleofection and AA V6 Transduction

After expansion, the pan-T cells were nucleofected with Cas9-RNPs and transduced with B2M/HLA-E-rAAV. Briefly, Cas9-RNPs were transfected into activated T cells (CD4+ and CD8+) using the Nucleofector™ 96-well Shuttle System (Lonza, Allendale, NJ). The Cas9-RNPs were dispensed in a 5 μl final volume into individual wells of a 96-well plate. Immunocult™ medium (Stemcell Technologies, Vancouver, Canada), supplemented with 5% FBS and 200 U/ml of rhIL-2, was added at 100 μl/well to a tissue culture 96-well plate for suspension cells. The suspended T cells were pelleted by centrifugation for 7 minutes at 200× g, and cells were washed with calcium- and magnesium-free phosphate buffered saline (PBS). Cells were pelleted by centrifugation for 7 minutes at 200× g, and the cells resuspended to $1 \times 10^7$ cells/ml in electroporation buffer (Lonza, Allendale, NJ). The cells were counted using the Countess II Automated Cell Counter™ (Life Technologies; Grand Island, NY).

20 μl of the cell suspension was then added to each individual well containing 5 μl of ribonucleoprotein complexes, and the entire volume from each well was transferred to a well of a 96-well Nucleocuvette™ Plate (Lonza, Allendale, NJ). The plate was loaded onto the Nucleofector™ 96-well Shuttle™ (Lonza, Allendale, NJ) and cells nucleofected. Post-nucleofection, 80 μl complete Immunocult™ medium (Stemcell Technologies, Vancouver, Canada), supplemented with 5% FBS, 200 U/mL rhIL-2, and 5.5 ml 100× Antibiotic-Antimycotic, was added to each well, and 50 μl of the cell suspension was transferred to a 96-well cell culture plate containing 100 μl pre-warmed complete Immunocult™ medium (Stemcell Technologies, Vancouver, Canada). The plate was transferred to a tissue culture incubator and maintained at 37° C. in 5% $CO_2$ for one day.

After 24 hours, $2 \times 10^5$ nucleofected T cells were transduced with 1 batch of rAAV. T cells were then transferred to a 96-well plate and incubated at 37° C., 5% $CO_2$ in complete Immunocult™ medium (Stemcell Technologies, Vancouver, Canada) until further analysis.

Cell Staining

T cells were assessed for target protein cell surface expression using FACS analysis and target protein-specific antibodies. $1 \times 10^5$ cells per sample of activated T cells were centrifuged at 300×g for 5 minutes to pellet cells. The supernatant was decanted. Cells were resuspended in 100 μl of FACS buffer (1×PBS with 2.5% FBS).

Anti-target protein antibodies were used, such as anti-HLA-E antibody labelled with BV421™ (Biolegend, San Diego, CA); anti-B2M antibody labelled with phycoerythrin (PE) (Biolegend, San Diego, CA); and/or anti-HLA-A/B/C labelled with Alexa467™ (Biolegend, San Diego, CA). Antibodies were added at a dilution of 1:100 and the samples were incubated on ice for 60 minutes. The samples were washed three times by adding 100 μl of FACS buffer, and centrifuged at approximately 300×g for 5 minutes.

Stained cells were then sorted on an Intellicyt iQue™ screener (Intellicyt, Sartorius, Albuquerque, NM), and the respective populations of BV421™, or PE, or equivalent dye-positive fluorescent cells tallied.

5-8 days after transduction, nucleofected and transduced T cells, wild-type (WT) T cells, and nucleofected cells only, were tallied for HLA-A/B/C-negative and B2M/HLA-E-positive cells. WT T cells had 0.023% HLA-A/B/C-negative/HLA-E-positive fractions; nucleofected only cells had 2.58% HLA-A/B/C-negative/HLA-E-positive fractions; and the nucleofected and B2M/HLA-E AAV6 transduced T cells had 15% HLA-A/B/C-negative/HLA-E-positive fractions.

The B2M/HLA-E constructs can be used as the basis for designing chimeric transmembrane proteins containing suicide modules.

Following the guidance of the present Specification, other types of lymphocytes can be isolated from PBMCs, nucleofected, and transduced with virus by one of ordinary skill in the art.

While preferred embodiments of the present invention have been shown and described herein, it will be obvious to those skilled in the art that such embodiments are provided by way of example only. It is understood that obvious variations can be made without departing from the spirit and the scope of the methods as defined herein.

TABLE 7

| SEQ ID NO: | Name | Sequence |
|---|---|---|
| SEQ ID NO: 1 | BCMA FL | MLQMAGQCSQNEYFDSLLHACIPCQLRCSSNTPPLTCQRYC NASVTNSVKGTNAILWTCLGLSLIISLAVFVLMFLLRKINSEP LKDEFKNTGSGLLGMANIDLEKSRTGDEIILPRGLEYTVEECT CEDCIKSKPKVDSDHCFPLPAMEEGATILVTTKTNDYCKSLP AALSATEIEKSISAR |
| SEQ ID NO: 2 | BCMA TM | ILWTCLGLSLIISLAVFVLMFLL |
| SEQ ID NO: 3 | BCMA ECD | MLQMAGQCSQNEYFDSLLHACIPCQLRCSSNTPPLTCQRYC NASVTNSVKGTNA |
| SEQ ID NO: 4 | BCMA ICD | RKINSEPLKDEFKNTGSGLLGMANIDLEKSRTGDEIILPRGLE YTVEECTCEDCIKSKPKVDSDHCFPLPAMEEGATILVTTKTN DYCKSLPAALSATEIEKSISAR |
| SEQ ID NO: 5 | BCMA ICD truncated I | RGSGLLGMANIDLEKSRTGDEIILPRGLEYTVEECTCEDCIKS KPKVDSDHCFPLPAMEEGATILVTTKTNDYCKSLPAALSATE IEKSISAR |
| SEQ ID NO: 6 | BCMA ICD truncated II | RKINSEPLKDEFKNTG |
| SEQ ID NO: 7 | BCMA ECD N-terminal truncation | GQCSQNEYFDSLLHACIPCQLRCSSNTPPLTCQRYCNASVTN SVKGTNA |

TABLE 7-continued

Table of sequences

| SEQ ID NO: | Name | Sequence |
|---|---|---|
| SEQ ID NO: 8 | BCMA ECD C-terminal truncation | MLQMAGQCSQNEYFDSLLHACIPCQLRCSSNTPPLTCQRYC |
| SEQ ID NO: 9 | BCMA ECD N- and C-terminal truncation | GQCSQNEYFDSLLHACIPCQLRCSSNTPPLTCQRYC |
| SEQ ID NO: 10 | CD8 alpha | MALPVTALLLPLALLLHAARPSQFRVSPLDRTWNLGETVEL KCQVLLSNPTSGCSWLFQPRGAAASPTFLLYLSQNKPKAAE GLDTQRFSGKRLGDTFVLTLSDFRRENEGYYFCSALSNSIM YFSHFVPVFLPAKPTTTPAPRPPTPAPTIASQPLSLRPEACRPA AGGAVHTRGLDFACDIYIWAPLAGTCGVLLLSLVITLYCN HRNRRRVCKCPRPVVKSGDKPSLSARYV |
| SEQ ID NO: 11 | CD8 alpha signal sequence | MALPVTALLLPLALLLHAARP |
| SEQ ID NO: 12 | CD8 alpha ECD | SQFRVSPLDRTWNLGETVELKCQVLLSNPTSGCSWLFQPRG AAASPTFLLYLSQNKPKAAEGLDTQRFSGKRLGDTFVL TLSDFRRENEGYYFCSALSNSIMYFSHFVPVFLPAKPTTTP APRPPTPAPTIASQPLSLRPEACRPAAGGAVHTRGLDFACD |
| SEQ ID NO: 13 | CD8 alpha TM | IYIWAPLAGTCGVLLLSLVIT |
| SEQ ID NO: 14 | CD8 alpha stalk | TTTPAPRPPTPAPTIASQPLSLRPEACRPAAGGAVHTRGLDFA CD |
| SEQ ID NO: 15 | GSG linker | GSG |
| SEQ ID NO: 16 | GGS linker | GGS |
| SEQ ID NO: 17 | (G3S) linker | GGGS |
| SEQ ID NO: 18 | (G4S) linker | GGGGS |
| SEQ ID NO: 19 | (G5S) linker | GGGGGS |
| SEQ ID NO: 20 | (G3S) linker | GGGS |
| SEQ ID NO: 21 | (GGS)7 linker | GGSGGSGGSGGSGGSGGSGGS |
| SEQ ID NO: 22 | triple A linker | AAA |
| SEQ ID NO: 23 | (G3S)3 | GGGSGGGSGGGS |
| SEQ ID NO: 24 | (G4S)3 | GGGGSGGGGSGGGGS |
| SEQ ID NO: 25 | (G4S)4 | GGGGSGGGGSGGGGSGGGGS |
| SEQ ID NO: 26 | (G4S)5 | GGGGSGGGGSGGGGSGGGGSGGGGS |
| SEQ ID NO: 27 | XTEN | SGSETPGTSESATPES |
| SEQ ID NO: 28 | B2M | MSRSVALAVLALLSLSGLEAIQRTPKIQVYSRHPAENGKSNF LNCYVSGFHPSDIEVDLLKNGERIEKVEHSDLSFSKDWSFYL LYYTEFTPTEKDEYACRVNHVTLSQPKIVKWDRDM |
| SEQ ID NO: 29 | B2M signal sequence | MSRSVALAVLALLSLSGLEA |
| SEQ ID NO: 30 | B2M mature | IQRTPKIQVYSRHPAENGKSNFLNCYVSGFHPSDIEVDLL KNGERIEKVEHSDLSFSKDWSFYLLYYTEFTPTEKDEYACRV NHVTLSQPKIVKWDRDM |
| SEQ ID NO: 31 | HLA-E | MVDGTLLLLLSEALALTQTWAGSHSLKYFHTSVSRPGRGEP RFISVGYVDDTQFVRFDNDAASPRMVPRAPWMEQEGSEY WDRETRSARDTAQIFRVNLRTLRGYYNQSEAGSHTLQWMH GCELGPDRRFLRGYEQFAYDGKDYLTLNEDLRSWTAVDTA AQISEQKSNDASEAEHQRAYLEDTCVEWLHKYLEKGKETL LHLEPPKTHVTHHPISDHEATLRCWALGFYPAEITLTWQQ DGEGHTQDTELVETRPAGDGTFQKWAAVVVPSGEEQRYTC HVQHEGLPEPVTLRWKPASQPTIPIVGIIAGLVLLGSVVSGAV VAAVIWRKKSSGKGGSYSKAEWSDSAQGSESHSL |
| SEQ ID NO: 32 | HLA-E signal sequence | MVDGTLLLLLSEALALTQTWA |
| SEQ ID NO: 33 | HLA-E mature | GSHSLKYFHTSVSRPGRGEPRFISVGYVDDTQFVRFDND |

TABLE 7-continued

Table of sequences

| SEQ ID NO: | Name | Sequence |
|---|---|---|
| | | AASPRMVPRAPWMEQEGSEYWDRETRSARDTAQIFRVNLR<br>TLRGYYNQSEAGSHTLQWMHGCELGPDRRFLRGYEQFA<br>YDGKDYLTLNEDLRSWTAVDTAAQISEQKSNDASEAEHQR<br>AYLEDTCVEWLHKYLEKGKETLLHLEPPKTHVTHHPISDHE<br>ATLRCWALGFYPAEITLTWQQDGEGHTQDTELVETRPAGDG<br>TFQKWAAVVVPSGEEQRYTCHVQHEGLPEPVTLRWKPAS<br>QPTIPIVGIIAGLVLLGSVVSGAVVAAVIWRKKSSGGKGGSY<br>SKAEWSDSAQGSESHSL |
| SEQ ID NO: 34 | HLA-G | MVVMAPRTLFLLLSGALTLTETWAGSHSMRYFSAAVSRPGR<br>GEPRFIAMGYVDDTQFVRFDSDSACPRMEPRAPWVEQ<br>EGPEYWEEETRNTKAHAQTDRMNLQTLRGYYNQSEASSHT<br>LQWMIGCDLGSDGRLLRGYEQYAYDGKDYLALNEDLRSWT<br>AADTAAQISKRKCEAANVAEQRRAYLEGTCVEWLHRYLEN<br>GKEMLQRADPPKTHVTHHPVFDYEATLRCWALGFYPAEIIL<br>TWQRDGEDQTQDVELVETRPAGDGTFQKWAAVVVPSG<br>EEQRYTCHVQHEGLPEPLMLRWKQSSLPTIPIMGIVAGLVVL<br>AAVVTGAAVAAVLWRKKSSD |
| SEQ ID NO: 35 | HLA-G signal sequence | MVVMAPRTLFLLLSGALTLTETWA |
| SEQ ID NO: 36 | HLA-G signal sequence short | VMAPRTLFL |
| SEQ ID NO: 37 | CD34 | MLVRRGARAGPRMPRGWTALCLLSLLPSGFMSLDNNGTAT<br>PELPTQGTFSNVSTNVSYQETTTPSTLGSTSLHPVSQHGNE<br>ATTNITETTVKFTSTSVITSVYGNTNSSVQSQTSVISTVFTTP<br>ANVSTPETTLKPSLSPGNVSDLSTTSTSLATSPTKPYTSSSPILS<br>DIKAEIKCSGIREVKLTQGICLEQNKTSSCAEFKKDRGEGLAR<br>VLCGEEQADADAGAQVCSLLLAQSEVRPQCLLLVLANR<br>TEISSKLQLMKKHQSDLKKLGILDFTEQDVASHQSYSQKTLI<br>ALVTSGALLAVLGITGYFLMNRRSWSPTGERLGEDPYYTE<br>NGGGQGYSSGPGTSPEAQGKASVNRGAQENGTGQATS<br>RNGHSARQHVVADTEL |
| SEQ ID NO: 38 | CD34 Q10 epitope | ELPTQGTFSNVSTNVS |
| SEQ ID NO: 39 | CD19 CAR | MLLLVTSLLLCELPHPAFLLIPDIQMTQTTSSLSASLGDRVTIS<br>CRASQDISKYLNWYQQKPDGTVKLLIYHTSRLHSGVPSRFSG<br>SGSGTDYSLTISNLEQEDIATYFCQQGNTLPYTFGGGTKLEIT<br>GSTSGSGKPGSGEGSTKGEVKLQESGPGLVAPSQSLSVTCTV<br>SGVSLPDYGVSWIRQPPRKGLEWLGVIWGSETTYYNSALKS<br>RLTIIKDNSKSQVFLKMNSLQTDDTAIYYCAKHYYYGGSYA<br>MDYWGQGTSVTVSSAAAIEVMYPPPYLDNEKSNGTIIHVKG<br>KHLCPSPLFPGPSKPFWVLVVVGGVLACYSLLVTVAFIIFWV<br>RSKRSRLLHSDYMNMTPRRPGPTRKHYQPYAPPRDFAAYRS<br>RVKFSRSADAPAYQQGQNQLYNELNLGRREEYDVLDKRRG<br>RDPEMGGKPRRKNPQEGLYNELQKDKMAEAYSEIGMKGER<br>RRGKGHDGLYQGLSTATKDTYDALHMQALPPR |
| SEQ ID NO: 40 | CAR signal sequence hGCMF | MLLLVTSLLLCELPHPAFLLIP |
| SEQ ID NO: 41 | Anti-CD19 scFv | DIQMTQTTSSLSASLGDRVTISCRASQDISKYLNWYQQKPDG<br>TVKLLIYHTSRLHSGVPSRFSGSGSGTDYSLTISNLEQEDIAT<br>YFCQQGNTLPYTFGGGTKLEITGSTSGSGKPGSGEGSTKGEV<br>KLQESGPGLVAPSQSLSVTCTVSGVSLPDYGVSWIRQPPRKG<br>LEWLGVIWGSETTYYNSALKSRLTIIKDNSKSQVFLKMNSLQ<br>TDDTAIYYCAKHYYYGGSYAMDYWGQGTSVTVS |
| SEQ ID NO: 42 | CAR hinge | AAAIEVMYPPPYLDNEKSNGTIIHVKGKHLCPSPLFPGPSKP |
| SEQ ID NO: 43 | CAR TM | FWVLVVVGGVLACYSLLVTVAFIIFWVR |
| SEQ ID NO: 44 | P2A | ATNFSLLKQAGDVEENPGP |
| SEQ ID NO: 45 | T2A | EGRGSLLTCGDVEENPGP |
| SEQ ID NO: 46 | BCMA ECD TM ICD truncated I | MLQMAGQCSQNEYFDSLLHACIPCQLRCSSNTPPLTCQRYC<br>NASVTNSVKGTNAILWTCLGLSLIISLAVFVLMFLLRGSLL<br>GMANIDLEKSRTGDEIILPRGLEYTVEECTCEDCIKSKPKVDS<br>DHCFPLPAMEEGATILVTTKTNDYCKSLPAALSATEIEKSISA<br>R |

TABLE 7-continued

Table of sequences

| SEQ ID NO: | Name | Sequence |
|---|---|---|
| SEQ ID NO: 47 | BCMA ECD TM ICD truncated II | MLQMAGQCSQNEYFDSLLHACIPCQLRCSSNTPPLTCQRYC NASVTNSVKGTNAILWTCLGLSLIISLAVFVLMFLLRKINSEP LKDEFKNTG |
| SEQ ID NO: 48 | BCMA ECD CD8 TM | MLQMAGQCSQNEYFDSLLHACIPCQLRCSSNTPPLTCQRYC NASVTNSVKGTNATTTPAPRPPTPAPTIASQPLSLRPEACRPA AGGAVHTRGLDFACDIYIWAPLAGTCGVLLLSLVIT |
| SEQ ID NO: 49 | BCMA ECD linker CD8TM | MLQMAGQCSQNEYFDSLLHACIPCQLRCSSNTPPLTCQRYC NASVTNSVKGTNAAAATTTPAPRPPTPAPTIASQPLSLRPEAC RPAAGGAVHTRGLDFACDIYIWAPLAGTCGVLLLSLVIT |
| SEQ ID NO: 50 | BCMA ECD CD34 CD8TM | MLQMAGQCSQNEYFDSLLHACIPCQLRCSSNTPPLTCQRYC NASVTNSVKGTNAELPTQGTFSNVSTNVSIYIWAPLAGTCGV LLLSLVIT |
| SEQ ID NO: 51 | BCMA ECD CD34 CD8 CD8TM | MLQMAGQCSQNEYFDSLLHACIPCQLRCSSNTPPLTCQRYC NASVTNSVKGTNAELPTQGTFSNVSTNVSTTTPAPRPPTPAP TIASQPLSLRPEACRPAAGGAVHTRGLDFACDIYIWAPLAGT CGVLLLSLVIT |
| SEQ ID NO: 52 | scFv SM CAR signaling | MLLLVTSLLLCELPHPAFLLIPDIQMTQTTSSLSASLGDRVTIS CRASQDISKYLNWYQQKPDGTVKLLIYHTSRLHSGVPSRFSG SGSGTDYSLTISNLEQEDIATYFCQQGNTLPYTFGGGTKLEIT GSTSGSGKPGSGEGSTKGEVKLQESGPGLVAPSQSLSVTCTV SGVSLPDYGVSWIRQPPRKGLEWLGVIWGSETTYYNSALKS RLTIIKDNSKSQVFLKMNSLQTDDTAIYYCAKHYYYGGSYA MDYWGQGTSVTVSSMLQMAGQCSQNEYFDSLLHACIPCQL RCSSNTPPLTCQRYCNASVTNSVKGTNAAAAIEVMYPPPYL DNEKSNGTIIHVKGKHLCPSPLFPGPSKPFWVLVVVGGVLAC YSLLVTVAFIIFWVRSKRSRLLHSDYMNMTPRRPGPTRKHY QPYAPPRDFAAYRSRVKFSRSADAPAYQQGQNQLYNELNLG RREEYDVLDKRRGRDPEMGGKPRRKNPQEGLYNELQKDKM AEAYSEIGMKGERRRGKGHDGLYQGLSTATKDTYDALHMQ ALPPR |
| SEQ ID NO: 53 | SM scFv CAR signaling | MLQMAGQCSQNEYFDSLLHACIPCQLRCSSNTPPLTCQRYC NASVTNSVKGTNADIQMTQTTSSLSASLGDRVTISCRASQDI SKYLNWYQQKPDGTVKLLIYHTSRLHSGVPSRFSGSGSGTD YSLTISNLEQEDIATYFCQQGNTLPYTFGGGTKLEITGSTSGS GKPGSGEGSTKGEVKLQESGPGLVAPSQSLSVTCTVSGVSLP DYGVSWIRQPPRKGLEWLGVIWGSETTYYNSALKSRLTIIKD NSKSQVFLKMNSLQTDDTAIYYCAKHYYYGGSYAMDYWG QGTSVTVSSAAAIEVMYPPPYLDNEKSNGTIIHVKGKHLCPS PLFPGPSKPFWVLVVVGGVLACYSLLVTVAFIIFWVRSKRSR LLHSDYMNMTPRRPGPTRKHYQPYAPPRDFAAYRSRVKFSR SADAPAYQQGQNQLYNELNLGRREEYDVLDKRRGRDPEMG GKPRRKNPQEGLYNELQKDKMAEAYSEIGMKGERRRGKGH DGLYQGLSTATKDTYDALHMQALPPR |
| SEQ ID NO: 54 | scFvD1 SMS scFvD2 CAR signaling | MLLLVTSLLLCELPHPAFLLIPDIQMTQTTSSLSASLGDRVTIS CRASQDISKYLNWYQQKPDGTVKLLIYHTSRLHSGVPSRFSG SGSGTDYSLTISNLEQEDIATYFCQQGNTLPYTFGGGTKLEIT MLQMAGQCSQNEYFDSLLHACIPCQLRCSSNTPPLTCQRYC NASVTNSVKGTNAEVKLQESGPGLVAPSQSLSVTCTVSGVS LPDYGVSWIRQPPRKGLEWLGVIWGSETTYYNSALKSRLTII KDNSKSQVFLKMNSLQTDDTAIYYCAKHYYYGGSYAMDY WGQGTSVTVSSAAAIEVMYPPPYLDNEKSNGTIIHVKGKHL CPSPLFPGPSKPFWVLVVVGGVLACYSLLVTVAFIIFWVRSK RSRLLHSDYMNMTPRRPGPTRKHYQPYAPPRDFAAYRSRVK FSRSADAPAYQQGQNQLYNELNLGRREEYDVLDKRRGRDP EMGGKPRRKNPQEGLYNELQKDKMAEAYSEIGMKGERRRG KGHDGLYQGLSTATKDTYDALHMQALPPR |
| SEQ ID NO: 55 | SS scFv SM CAR signaling | MLQMAGQCSQNEYFDSLLHACIPCQLRCSSNTPPLTCQRYC NASVTNSVKGTNADIQMTQTTSSLSASLGDRVTISCRASQDI SKYLNWYQQKPDGTVKLLIYHTSRLHSGVPSRFSGSGSGTD YSLTISNLEQEDIATYFCQQGNTLPYTFGGGTKLEITGSTSGS GKPGSGEGSTKGEVKLQESGPGLVAPSQSLSVTCTVSGVSLP DYGVSWIRQPPRKGLEWLGVIWGSETTYYNSALKSRLTIIKD NSKSQVFLKMNSLQTDDTAIYYCAKHYYYGGSYAMDYWG QGTSVTVSSMLQMAGQCSQNEYFDSLLHACIPCQLRCSSNTP PLTCQRYCNASVTNSVKGTNAAAAIEVMYPPPYLDNEKSNG TIIHVKGKHLCPSPLFPGPSKPFWVLVVVGGVLACYSLLVTV AFIIFWVRSKRSRLLHSDYMNMTPRRPGPTRKHYQPYAPPRD |

TABLE 7-continued

Table of sequences

| SEQ ID NO: | Name | Sequence |
|---|---|---|
| | | FAAYRSRVKFSRSADAPAYQQGQNQLYNELNLGRREEYDV<br>LDKRRGRDPEMGGKPRRKNPQEGLYNELQKDKMAEAYSEI<br>GMKGERRRGKGHDGLYQGLSTATKDTYDALHMQALPPR |
| SEQ ID NO: 56 | CAR-T2A-BCMA suicide switch | MLLLVTSLLLCELPHPAFLLIPDIQMTQTTSSLSASLGDRVTIS<br>CRASQDISKYLNWYQQKPDGTVKLLIYHTSRLHSGVPSRFSG<br>SGSGTDYSLTISNLEQEDIATYFCQQGNTLPYTFGGGTKLEIT<br>GSTSGSGKPGSGEGSTKGEVKLQESGPGLVAPSQSLSVTCTV<br>SGVSLPDYGVSWIRQPPRKGLEWLGVIWGSETTYYNSALKS<br>RLTIIKDNSKSQVFLKMNSLQTDDTAIYYCAKHYYYGGSYA<br>MDYWGQGTSVTVSSAAAIEVMYPPPYLDNEKSNGTIIHVKG<br>KHLCPSPLFPGPSKPFWVLVVVGGVLACYSLLVTVAFIIFWV<br>RSKRSRLLHSDYMNMTPRRPGPTRKHYQPYAPPRDFAAYRS<br>RVKFSRSADAPAYQQGQNQLYNELNLGRREEYDVLDKRRG<br>RDPEMGGKPRRKNPQEGLYNELQKDKMAEAYSEIGMKGER<br>RRGKGHDGLYQGLSTATKDTYDALHMQALPPRGSGEGRGS<br>LLTCGDVEENPGPMLQMAGQCSQNEYFDSLLHACIPCQLRC<br>SSNTPPLTCQRYCNASVTNSVKGTNATTTPAPRPPTPAPTIAS<br>QPLSLRPEACRPAAGGAVHTRGLDFACDIYIWAPLAGTCGV<br>LLLSLVIT |
| SEQ ID NO: 57 | HLA-G/B2M/HLA-E fusion | VMAPRTLFLGGGGSGGGGSGGGGSIQRTPKIQVYSRHPAEN<br>GKSNFLNCYVSGFHPSDIEVDLLKNGERIEKVEHSDLSFSKD<br>WSFYLLYYTEFTPTEKDEYACRVNHVTLSQPKIVKWDRDM<br>GGGGSGGGGSGGGGSGGGGSGGGGSGSHSLKYFHTSVSRPGRGEPR<br>FISVGYVDDTQFVRFDNDAASPRMVPRAPWMEQEGSEYWD<br>RETRSARDTAQIFRVNLRTLRGYYNQSEAGSHTLQWMHGCE<br>LGPDRRFLRGYEQFAYDGKDYLTLNEDLRSWTAVDTAAQIS<br>EQKSNDASEAEHQRAYLEDTCVEWLHKYLEKGKETLLHLEP<br>PKTHVTHHPISDHEATLRCWALGFYPAEITLTWQQDGEGHT<br>QDTELVETRPAGDGTFQKWAAVVVPSGEEQRYTCHVQHEG<br>LPEPVTLRWKPASQPTIPIVGIIAGLVLLGSVVSGAVVAAVIW<br>RKKSSGGKGGSYSKAEWSDSAQGSESHSL |
| SEQ ID NO: 58 | B2M/HLA-E fusion | IQRTPKIQVYSRHPAENGKSNFLNCYVSGFHPSDIEVDLLKN<br>GERIEKVEHSDLSFSKDWSFYLLYYTEFTPTEKDEYACRVNH<br>VTLSQPKIVKWDRDMGGGGSGGGGSGGGGSGGGGSGSHSL<br>KYFHTSVSRPGRGEPRFISVGYVDDTQFVRFDND<br>AASPRMVPRAPWMEQEGSEYWDRETRSARDTAQIFRVNLR<br>TLRGYYNQSEAGSHTLQWMHGCELGPDRRFLRGYEQFAYD<br>GKDYLTLNEDLRSWTAVDTAAQISEQKSNDASEAEHQRAYL<br>EDTCVEWLHKYLEKGKETLLHLEPPKTHVTHHPISDHEATL<br>RCWALGFYPAEITLTWQQDGEGHTQDTELVETRPAGDGTFQ<br>KWAAVVVPSGEEQRYTCHVQHEGLPEPVTLRWKPASQPTIP<br>IVGIIAGLVLLGSVVSGAVVAAVIWRKKSSGGKGGSYSKAE<br>WSDSAQGSESHSL |
| SEQ ID NO: 59 | HLA-G/BCMA/B2M/HLA-E fusion | VMAPRTLFLGSGMLQMAGQCSQNEYFDSLLHACIPCQLRCS<br>SNTPPLTCQRYCNASVTNSVKGTNAGSGIQRTPKIQVYSRHP<br>AENGKSNFLNCYVSGFHPSDIEVDLLKNGERIEKVEHSDL<br>SFSKDWSFYLLYYTEFTPTEKDEYACRVNHVTLSQPKIVK<br>WDRDMGGGGSGGGGSGGGGSGGGGSGSHSLKYFHTSVSRP<br>GRGEPRFISVGYVDDTQFVRFDNDAASPRMVPRAP<br>WMEQEGSEYWDRETRSARDTAQIFRVNLRTLRGYYNQSEA<br>GSHTLQWMHGCELGPDRRFLRGYEQFAYDGKDYLTLNE<br>DLRSWTAVDTAAQISEQKSNDASEAEHQRAYLEDTCVE<br>WLHKYLEKGKETLLHLEPPKTHVTHHPISDHEATLRCWALG<br>FYPAEITLTWQQDGEGHTQDTELVETRPAGDGTFQKWAAV<br>VVPSGEEQRYTCHVQHEGLPEPVTLRWKPASQPTIPIVGI<br>IAGLVLLGSVVSGAVVAAVIWRKKSSGGKGGSYSKAEWSDS<br>AQGSESHSL |
| SEQ ID NO: 60 | HLA-G/B2M/BCMA/HLA-E fusion | VMAPRTLFLGGGGSGGGGSGGGGSIQRTPKIQVYSRHPAEN<br>GKSNFLNCYVSGFHPSDIEVDLLKNGERIEKVEHSDLSFSKD<br>WSFYLLYYTEFTPTEKDEYACRVNHVTLSQPKIVKWDRDM<br>GSGMLQMAGQCSQNEYFDSLLHACIPCQLRCSSNTPPLTCQ<br>RYCNASVTNSVKGTNAGSGGHSLKYFHTSVSRPGRGEPRFI<br>SVGYVDDTQFVRFDNDAASPRMVPRAPWMEQEGSEYWDR<br>ETRSARDTAQIFRVNLRTLRGYYNQSEAGSHTLQWMHGCEL<br>GPDRRFLRGYEQFAYDGKDYLTLNEDLRSWTAVDTAAQISE<br>QKSNDASEAEHQRAYLEDTCVEWLHKYLEKGKETLLHLEPP<br>KTHVTHHPISDHEATLRCWALGFYPAEITLTWQQDGEGHTQ<br>DTELVETRPAGDGTFQKWAAVVVPSGEEQRYTCHVQHEGL<br>PEPVTLRWKPASQPTIPIVGIIAGLVLLGSVVSGAVVAAVIWR<br>KKSSGGKGGSYSKAEWSDSAQGSESHSL |

TABLE 7-continued

Table of sequences

| SEQ ID NO: | Name | Sequence |
|---|---|---|
| SEQ ID NO: 61 | HLA-G/BCMA/B2M/BCMA/HLA-E fusion | VMAPRTLFLMLQMAGQCSQNEYFDSLLHACIPCQLRCSSNT<br>PPLTCQRYCNASVTNSVKGTNAIQRTPKIQVYSRHPAENGKS<br>NFLNCYVSGFHPSDIEVDLLKNGERIEKVEHSDLSFSKDWSF<br>YLLYYTEFTPTEKDEYACRVNHVTLSQPKIVKWDRDMMLQ<br>MAGQCSQNEYFDSLLHACIPCQLRCSSNTPPLTCQRYCNASV<br>TNSVKGTNAGSHSLKYFHTSVSRPGRGEPRFISVGYVDDTQF<br>VRFDNDAASPRMVPRAPWMEQEGSEYWDRET<br>RSARDTAQIFRVNLRTLRGYYNQSEAGSHTLQWMHGCELG<br>PDRRFLRGYEQFAYDGKDYLTLNEDLRSWTAVDTAAQISEQ<br>KSNDASEAEHQRAYLEDTCVEWLHKYLEKGKETLLHLEPPK<br>THVTHHPISDHEATLRCWALGFYPAEITLTWQQDGEGHTQD<br>TELVETRPAGDGTFQKWAAVVVPSGEEQRYTCHVQHEGLP<br>EPVTLRWKPASQPTIPIVGIIAGLVLLGSVVSGAVVAAVIWR<br>KKSSGGKGGSYSKAEWSDSAQGSESHSL |
| SEQ ID NO: 62 | BCMA/B2M/HLA-E fusion | MLQMAGQCSQNEYFDSLLHACIPCQLRCSSNTPPLTCQRYC<br>NASVTNSVKGTNAGSGIQRTPKIQVYSRHPAENGKSNFLNC<br>YVSGFHPSDIEVDLLKNGERIEKVEHSDLSFSKDWSFYLLYY<br>TEFTPTEKDEYACRVNHVTLSQPKIVKWDRDMGGGGSGGG<br>GSGGGGSGGGGSGSHSLKYFHTSVSRPGRGEPRFISVGYVDD<br>TQFVRFDNDAASPRMVPRAPWMEQEGSEYWDRETSARDT<br>AQIFRVNLRTLRGYYNQSEAGSHTLQWMHGCELGPDRRFLR<br>GYEQFAYDGKDYLTLNEDLRSWTAVDTAAQISEQKSNDASE<br>AEHQRAYLEDTCVEWLHKYLEKGKETLLHLEPPKTHVTHHP<br>ISDHEATLRCWALGFYPAEITLTWQQDGEGHTQDTELVETR<br>PAGDGTFQKWAAVVVPSGEEQRYTCHVQHEGLPEPVTLRW<br>KPASQPTIPIVGIIAGLVLLGSVVSGAVVAAVIWRKKSSGGK<br>GGSYSKAEWSDSAQGSESHSL |
| SEQ ID NO: 63 | HLA-G/B2M/HLA-E 2A BCMA SM | VMAPRTLFLGGGGSGGGGGGGGSIQRTPKIQVYSRHPAEN<br>GKSNFLNCYVSGFHPSDIEVDLLKNGERIEKVEHSDLSFSKD<br>WSFYLLYYTEFTPTEKDEYACRVNHVTLSQPKIVKWDRDM<br>GGGGSGGGGSGGGGSGGGGSGSHSLKYFHTSVSRPGRGEPR<br>FISVGYVDDTQFVRFDNDAASPRMVPRAPWMEQEGSEYWD<br>RETRSARDTAQIFRVNLRTLRGYYNQSEAGSHTLQWMHGCE<br>LGPDRRFLRGYEQFAYDGKDYLTLNEDLRSWTAVDTAAQIS<br>EQKSNDASEAEHQRAYLEDTCVEWLHKYLEKGKETLLHLEP<br>PKTHVTHHPISDHEATLRCWALGFYPAEITLTWQQDGEGHT<br>QDTELVETRPAGDGTFQKWAAVVVPSGEEQRYTCHVQHEG<br>LPEPVTLRWKPASQPTIPIVGIIAGLVLLGSVVSGAVVAAVIW<br>RKKSSGGKGGSYSKAEWSDSAQGSESHSLEGRGSLLTCGDV<br>EENPGPMLQMAGQCSQNEYFDSLLHACIPCQLRCSSNTPPLT<br>CQRYCNASVTNSVKGTNAILWTCLGLSLIISLAVFVLMFLLR<br>KINSEPLKDEFKNTGSGLLGMANIDLEKSRTGDEIILPRGLEY<br>TVEECTCEDCIKSKPKVDSDHCFPLPAMEEGATILVTTKIND<br>YCKSLPAALSATEIEKSISAR |
| SEQ ID NO: 64 | CD28 | MLRLLLALNLFPSIQVTGNKILVKQSPMLVAYDNAVNLSCK<br>YSYNLFSREFRASLHKGLDSAVEVCVVYGNYSQQLQVYSKT<br>GFNCDGKLGNESVTFYLQNLYVNQTDIYFCKIEVMYPPPYL<br>DNEKSNGTIIHVKGKHLCPSPLFPGPSKPFWVLVVVGGVLAC<br>YSLLVTVAFIIFWVRSKRSRLLHSDYMNMTPRRPGPTRKHY<br>QPYAPPRDFAAYRS |
| SEQ ID NO: 65 | HLA-G/B2M/HLA-E fusion nucleotide sequence reverse | TACAAGCTGTGAGACTCAGACCCCTGGGCACTGTCGCTCC<br>ACTCAGCCTTAGAGTAGCTCCCTCCTTTTCCACCTGAGCTC<br>TTCTTCCTCCATATCACAGCAGCAACCACAGCTCCAGAGA<br>CCACAGATCCAAGGAGAACCAGGCCAGCAATGATGCCCA<br>CGATGGGGATGGTGGGCTGGGAAGCCGGCTTCCATCTCA<br>GGGTGACGGGCTCGGGTAGCCCCTCATGCTGCACATGGCA<br>CGTGTATCTCTGCTCCTCTCCAGAAGGCACCACCACAGCT<br>GCCCACTTCTGGAAGGTTCCATCCCCTGCAGGCCTGGTCT<br>CCACGAGCTCCGTGTCCTGGGTATGGCCCTCCCCATCCTG<br>CTGCCAGGTCAGTGTGATCTCCGCAGGGTAGAAGCCCAG<br>GGCCCAGCACCTCAGGGTGGCCTCATGGTCAGAGATGGG<br>GTGGTGAGTCACGTGTGTCTTTGGGGGCTCCAGGTGAAGC<br>AGCGTCTCCTTCCCCTTCTCCAGGTATTTGTGGAGCCACTC<br>CACGCATGTGTCTTCCAGGTAGGCTCTCTGGTGCTCCGCC<br>TCAGAAGCATCATTTGACTTTTGCTCGGAGATCTGAGCCG<br>CCGTGTCCACCGCGGTCCAGGAGCGCAGGTCCTCATTCAG<br>GGTGAGATACCTTGCCGTCGTAGGCGAACTGTTCTACAC<br>CCGCGGAGGAAGCGCCCGTCGGGCCCCAGCTCGCAGCCA<br>TGCATCCACTGCAGGGTGTGAGACCCGGCCTCGCTCTGAT<br>TGTAGTAGCCGCGCAGCGTCCGCAGATTCACTCGGAAAAT<br>CTGTGCGGTGTCCCTGGCGCTCCGTGTCTCCCGGTCCCAA<br>TACTCTGACCCCTCCTGCTCCATCCACGGCGCCCGCGGCA |

TABLE 7-continued

Table of sequences

| SEQ ID NO: | Name | Sequence |
|---|---|---|
| | | CCATCCTCGGACTCGCGGCGTCGTTGTCGAAGCGCACGAA
CTGGGTGTCGTCCACGTAGCCCACAGAGATGAAGCGGGG
CTCCCCGCGGCCGGGCCGGGACACGGAAGTGTGGAAATA
CTTCAAGGAGTGGGATCCAGACCCTCCGCCACCAGATCCC
CCTCCTCCAGAACCGCCTCCGCCAGACCCTCCGCCACCcatg
tctcgatcccacttaactatcttgggctgtgacaaagtcacatggttca
cacGgcaggcatactcatcttttcagtgggggtgaattcagtgtagta
caagagatagaaagaccagtccttgctgaaagacaagtctgaatgctcc
acttttcaattctctctccattcttcagtaagtcaacttcaatgtcgg
atggatgaaacccagacacatagcaattcaggaaatttgactttccatt
ctctgctggatgacgtgagtaaacctgaatctttggagtacgctggatG
GAGCCGCCGCCTCCGCTACCGCCTCCTCCGCTCCCACCTCCACCCAGAA
AGAGGGTCCGTGGTGCCATTAcagcctccaggccagaaagagagagtag
cgcgagcacagctaaggccacggagcgagacat |
| SEQ ID NO: 66 | B2M left homology arm | TTCCCAAGCTGTAGTTATAAACAGAAGTTCTCCTTCTGCT
AGGTAGCATTCAAAGATCTTAATCTTCTGGGTTTCCGTTTT
CTCGAATGAAAAATGCAGGTCCGAGCAGTTAACTGGCTG
GGGCACCATTAGCAAGTCACTTAGCATCTCTGGGGCCAGT
CTGCAAAGCGAGGGGGCAGCCTTAATGTGCCTCCAGCCTG
AAGTCCTAGAATGAGCGCCCGGTGTCCCAAGCTGGGGCG
CGCACCCCAGATCGGAGGGCGCCGATGTACAGACAGCAA
ACTCACCCAGTCTAGTGCATGCCTTCTTAAACATCACGAG
ACTCTAAGAAAAGGAAACTGAAAACGGGAAAGTCCCTCT
CTCTAACCTGGCACTGCGTCGCTGGCTTGGAGACAGGTGA
CGGTCCCTGCGGGCCTTGTCCTGATTGGCTGGGCACGCGT
TTAATATAAGTGGAGGCGTCGCGCTGGCGGGCATTCCTGA
AGCTGACAGCATTCGGGCCGAGA |
| SEQ ID NO: 67 | B2M right homology arm | GCTGTGCTCGCGCTACTCTCTCTTTCTGGCCTGGAGGCTAT
CCAGCGTGAGTCTCTCCTACCCTCCCGCTCTGGTCCTTCCT
CTCCCGCTCTGCACCCTCTGTGGCCCTCGCTGTGCTCTCTC
GCTCCGTGACTTCCCTTCTCCAAGTTCTCCTTGGTGGCCCG
CCGTGGGGCTAGTCCAGGGCTGGATCTCGGGGAAGCGGC
GGGGTGGCCTGGGAGTGGGGAAGGGGGTGCGCACCCGGG
ACGCGCGCTACTTGCCCCTTTCGGCGGGGAGCAGGGGAG
ACCTTTGGCCTACGGCGACGGGAGGGTCGGGACAAAGTT
TAGGGCGTCGATAAGCGTCAGAGCGCCGAGGTTGGGGGA
GGGTTTCTCTTCCGCTCTTTCGCGGGGCCTCTGGCTCCCCC
AGCGCAGCTGGAGTGGGGGACGGGTAGGCTCGTCCCAAA
GGCGCGGCGCTGAGGTTTGTGAACGCGTGGAGGGGCGCT
TG |

The invention claimed is:

1. A chimeric transmembrane protein comprising:
a suicide module comprising a ligand binding domain comprising the B cell maturation antigen extracellular domain, and a transmembrane domain, wherein the chimeric transmembrane protein comprises an amino acid sequence selected from the group consisting of SEQ ID NO:48, SEQ ID NO:49, SEQ ID NO:50, and SEQ ID NO:51.

2. The chimeric transmembrane protein of claim 1, further comprising a chimeric antigen receptor comprising a single-chain immunoglobulin variable fragment and a chimeric antigen receptor signaling domain.

3. The chimeric transmembrane protein of claim 2, wherein the suicide module is located between the single-chain immunoglobulin variable fragment and the chimeric antigen receptor signaling domain.

4. The chimeric transmembrane protein of claim 2, further comprising a self-cleaving peptide located between the suicide module and the chimeric antigen receptor.

5. An engineered cell comprising the chimeric transmembrane protein of claim 1.

6. The engineered cell of claim 5, wherein the engineered cell is a CAR-T cell.

7. A method of selectively killing an engineered adoptive cell comprising:
engineering the adoptive cell by introducing a suicide module into the adoptive cell, wherein the suicide module comprises a ligand binding domain comprising the B cell maturation antigen extracellular domain and a transmembrane domain, wherein the chimeric transmembrane protein comprises an amino acid sequence selected from the group consisting of SEQ ID NO:48, SEQ ID NO:49, SEQ ID NO:50, and SEQ ID NO:51;
introducing the engineered adoptive cell into a subject; and
introducing into the subject a ligand capable of binding the ligand binding domain, thereby resulting in killing of the engineered adoptive cell.

8. The method of claim 7, wherein the ligand is an antibody capable of binding the ligand binding domain.

9. The method of claim 8, wherein the antibody is conjugated to a cytotoxic molecule, and the conjugated antibody-cytotoxic molecule is selected from the group consisting of GSK2857916, MEDI2228, AMG 224, and HDP-101.

10. A method of making an engineered cell, the method comprising
introducing into a cell a nucleic acid encoding a chimeric transmembrane protein of claim 1.

11. The method of claim 10, wherein the nucleic acid is introduced into the cell in vitro.

12. The method of claim 10, wherein the nucleic acid is introduced into the cell by a virus.

13. The method of claim 12, wherein the virus is an adeno-associated virus type 6 (AAV6).

* * * * *

SEQUENCE LISTING

<160> NUMBER OF SEQ ID NOS: 67

<210> SEQ ID NO 1
<211> LENGTH: 184
<212> TYPE: PRT
<213> ORGANISM: Homo sapiens
<220> FEATURE:
<221> NAME/KEY: misc_feature
<222> LOCATION: (1)..(184)
<223> OTHER INFORMATION: BCMA FL

<400> SEQUENCE: 1

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile

```
                65                  70                  75                  80
Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Cys Thr Cys
            115                 120                 125

Glu Asp Cys Ile Lys Ser Lys Pro Lys Val Asp Ser Asp His Cys Phe
        130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 2
<211> LENGTH: 23
<212> TYPE: PRT
<213> ORGANISM: Artificial Sequence
<220> FEATURE:
<223> OTHER INFORMATION: Synthetic: H. sapiens partial, BCMA TM

<400> SEQUENCE: 2

Ile Leu Trp Thr Cys Leu Gly Leu Ser Leu Ile Ile Ser Leu Ala Val
1               5                   10                  15

Phe Val Leu Met Phe Leu Leu
            20

<210> SEQ ID NO 3
<211> LENGTH: 54
<212> TYPE: PRT
<213> ORGANISM: Artificial Sequence
<220> FEATURE:
<223> OTHER INFORMATION: Synthetic: H. sapiens partial, BCMA ECD

<400> SEQUENCE: 3

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala
    50

<210> SEQ ID NO 4
<211> LENGTH: 107
<212> TYPE: PRT
<213> ORGANISM: Artificial Sequence
<220> FEATURE:
<223> OTHER INFORMATION: Synthetic: H. sapiens partial, BCMA ICD

<400> SEQUENCE: 4

Arg Lys Ile Asn Ser Glu Pro Leu Lys Asp Glu Phe Lys Asn Thr Gly
1               5                   10                  15

Ser Gly Leu Leu Gly Met Ala Asn Ile Asp Leu Glu Lys Ser Arg Thr
            20                  25                  30

Gly Asp Glu Ile Ile Leu Pro Arg Gly Leu Glu Tyr Thr Val Glu Glu
        35                  40                  45
```

```
Cys Thr Cys Glu Asp Cys Ile Lys Ser Lys Pro Lys Val Asp Ser Asp
        50                  55                  60
His Cys Phe Pro Leu Pro Ala Met Glu Gly Ala Thr Ile Leu Val
 65                  70                  75                  80
Thr Thr Lys Thr Asn Asp Tyr Cys Lys Ser Leu Pro Ala Ala Leu Ser
                85                  90                  95
Ala Thr Glu Ile Glu Lys Ser Ile Ser Ala Arg
            100                 105
```

<210> SEQ ID NO 5
<211> LENGTH: 93
<212> TYPE: PRT
<213> ORGANISM: Artificial Sequence
<220> FEATURE:
<223> OTHER INFORMATION: Synthetic: H. sapiens partial, BCMA ICD
      truncated I

<400> SEQUENCE: 5

```
Arg Gly Ser Gly Leu Leu Gly Met Ala Asn Ile Asp Leu Glu Lys Ser
 1               5                  10                  15
Arg Thr Gly Asp Glu Ile Ile Leu Pro Arg Gly Leu Glu Tyr Thr Val
                20                  25                  30
Glu Glu Cys Thr Cys Glu Asp Cys Ile Lys Ser Lys Pro Lys Val Asp
            35                  40                  45
Ser Asp His Cys Phe Pro Leu Pro Ala Met Glu Gly Ala Thr Ile
         50                  55                  60
Leu Val Thr Thr Lys Thr Asn Asp Tyr Cys Lys Ser Leu Pro Ala Ala
 65                  70                  75                  80
Leu Ser Ala Thr Glu Ile Glu Lys Ser Ile Ser Ala Arg
                85                  90
```

<210> SEQ ID NO 6
<211> LENGTH: 16
<212> TYPE: PRT
<213> ORGANISM: Artificial Sequence
<220> FEATURE:
<223> OTHER INFORMATION: Synthetic: H. sapiens partial, BCMA ICD
      truncated II

<400> SEQUENCE: 6

```
Arg Lys Ile Asn Ser Glu Pro Leu Lys Asp Glu Phe Lys Asn Thr Gly
 1               5                  10                  15
```

<210> SEQ ID NO 7
<211> LENGTH: 49
<212> TYPE: PRT
<213> ORGANISM: Artificial Sequence
<220> FEATURE:
<223> OTHER INFORMATION: Synthetic: H. sapiens partial, BCMA ECD
      N-terminal truncation

<400> SEQUENCE: 7

```
Gly Gln Cys Ser Gln Asn Glu Tyr Phe Asp Ser Leu Leu His Ala Cys
 1               5                  10                  15
Ile Pro Cys Gln Leu Arg Cys Ser Ser Asn Thr Pro Pro Leu Thr Cys
                20                  25                  30
Gln Arg Tyr Cys Asn Ala Ser Val Thr Asn Ser Val Lys Gly Thr Asn
            35                  40                  45
Ala
```

```
<210> SEQ ID NO 8
<211> LENGTH: 41
<212> TYPE: PRT
<213> ORGANISM: Artificial Sequence
<220> FEATURE:
<223> OTHER INFORMATION: Synthetic: H. sapiens partial, BCMA ECD
      C-terminal truncation

<400> SEQUENCE: 8

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys
        35                  40

<210> SEQ ID NO 9
<211> LENGTH: 36
<212> TYPE: PRT
<213> ORGANISM: Artificial Sequence
<220> FEATURE:
<223> OTHER INFORMATION: Synthetic: H. sapiens partial, BCMA ECD N- and
      C- terminal truncation

<400> SEQUENCE: 9

Gly Gln Cys Ser Gln Asn Glu Tyr Phe Asp Ser Leu Leu His Ala Cys
1               5                   10                  15

Ile Pro Cys Gln Leu Arg Cys Ser Ser Asn Thr Pro Pro Leu Thr Cys
            20                  25                  30

Gln Arg Tyr Cys
        35

<210> SEQ ID NO 10
<211> LENGTH: 235
<212> TYPE: PRT
<213> ORGANISM: Homo sapiens
<220> FEATURE:
<221> NAME/KEY: misc_feature
<222> LOCATION: (1)..(235)
<223> OTHER INFORMATION: CD8 alpha

<400> SEQUENCE: 10

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
```

```
145                 150                 155                 160
Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
                195                 200                 205

Arg Asn Arg Arg Arg Val Cys Lys Cys Pro Arg Pro Val Val Lys Ser
            210                 215                 220

Gly Asp Lys Pro Ser Leu Ser Ala Arg Tyr Val
225                 230                 235

<210> SEQ ID NO 11
<211> LENGTH: 21
<212> TYPE: PRT
<213> ORGANISM: Artificial Sequence
<220> FEATURE:
<223> OTHER INFORMATION: Synthetic: H. sapiens partial, CD8 alpha signal
      sequence

<400> SEQUENCE: 11

Met Ala Leu Pro Val Thr Ala Leu Leu Leu Pro Leu Ala Leu Leu Leu
1               5                   10                  15

His Ala Ala Arg Pro
            20

<210> SEQ ID NO 12
<211> LENGTH: 161
<212> TYPE: PRT
<213> ORGANISM: Artificial Sequence
<220> FEATURE:
<223> OTHER INFORMATION: Synthetic: H. sapiens partial, CD8 alpha ECD

<400> SEQUENCE: 12

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
    50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala Lys Pro Thr Thr Thr Pro Ala Pro Arg Pro Pro Thr Pro Ala
        115                 120                 125

Pro Thr Ile Ala Ser Gln Pro Leu Ser Leu Arg Pro Glu Ala Cys Arg
    130                 135                 140

Pro Ala Ala Gly Gly Ala Val His Thr Arg Gly Leu Asp Phe Ala Cys
145                 150                 155                 160

Asp

<210> SEQ ID NO 13
<211> LENGTH: 21
```

```
<212> TYPE: PRT
<213> ORGANISM: Artificial Sequence
<220> FEATURE:
<223> OTHER INFORMATION: Synthetic: H. sapiens partial, CD8 alpha TM

<400> SEQUENCE: 13

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 14
<211> LENGTH: 45
<212> TYPE: PRT
<213> ORGANISM: Artificial Sequence
<220> FEATURE:
<223> OTHER INFORMATION: Synthetic: H. sapiens partial, CD8 alpha stalk

<400> SEQUENCE: 14

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 15
<211> LENGTH: 3
<212> TYPE: PRT
<213> ORGANISM: Artificial Sequence
<220> FEATURE:
<223> OTHER INFORMATION: Synthetic: GSG linker

<400> SEQUENCE: 15

Gly Ser Gly
1

<210> SEQ ID NO 16
<211> LENGTH: 3
<212> TYPE: PRT
<213> ORGANISM: Artificial Sequence
<220> FEATURE:
<223> OTHER INFORMATION: Synthetic: GGS linker

<400> SEQUENCE: 16

Gly Gly Ser
1

<210> SEQ ID NO 17
<211> LENGTH: 4
<212> TYPE: PRT
<213> ORGANISM: Artificial Sequence
<220> FEATURE:
<223> OTHER INFORMATION: Synthetic: (G3S) linker

<400> SEQUENCE: 17

Gly Gly Gly Ser
1

<210> SEQ ID NO 18
<211> LENGTH: 5
<212> TYPE: PRT
<213> ORGANISM: Artificial Sequence
<220> FEATURE:
<223> OTHER INFORMATION: Synthetic: (G4S) linker
```

<400> SEQUENCE: 18

Gly Gly Gly Gly Ser
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic: (G5S) linker

<400> SEQUENCE: 19

Gly Gly Gly Gly Gly Ser
1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic: (G3S) linker

<400> SEQUENCE: 20

Gly Gly Gly Ser
1

<210> SEQ ID NO 21
<211> LENGTH: 21
<212> TYPE: PRT
<213> ORGANISM: Artificial Sequence
<220> FEATURE:
<223> OTHER INFORMATION: Synthetic: (GGS)7 linker

<400> SEQUENCE: 21

Gly Gly Ser Gly Gly Ser Gly Gly Ser Gly Gly Ser Gly Gly Ser Gly
1               5                   10                  15

Gly Ser Gly Gly Ser
            20

<210> SEQ ID NO 22
<211> LENGTH: 3
<212> TYPE: PRT
<213> ORGANISM: Artificial Sequence
<220> FEATURE:
<223> OTHER INFORMATION: Synthetic: triple A linker

<400> SEQUENCE: 22

Ala Ala Ala
1

<210> SEQ ID NO 23
<211> LENGTH: 12
<212> TYPE: PRT
<213> ORGANISM: Artificial Sequence
<220> FEATURE:
<223> OTHER INFORMATION: Synthetic: (G3S)3

<400> SEQUENCE: 23

Gly Gly Gly Ser Gly Gly Gly Ser Gly Gly Gly Ser
1               5                   10

<210> SEQ ID NO 24
<211> LENGTH: 15
<212> TYPE: PRT
<213> ORGANISM: Artificial Sequence
<220> FEATURE:

-continued

```
<223> OTHER INFORMATION: Synthetic: (G4S)3

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 20
<212> TYPE: PRT
<213> ORGANISM: Artificial Sequence
<220> FEATURE:
<223> OTHER INFORMATION: Synthetic: (G4S)4

<400> SEQUENCE: 25

Gly Gly Gly Gly Ser Gly Gly Gly Gly Ser Gly Gly Gly Gly Ser Gly
1               5                   10                  15

Gly Gly Gly Ser
            20

<210> SEQ ID NO 26
<211> LENGTH: 25
<212> TYPE: PRT
<213> ORGANISM: Artificial Sequence
<220> FEATURE:
<223> OTHER INFORMATION: Synthetic: (G4S)5

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 27
<211> LENGTH: 16
<212> TYPE: PRT
<213> ORGANISM: Artificial Sequence
<220> FEATURE:
<223> OTHER INFORMATION: Synthetic: XTEN

<400> SEQUENCE: 27

Ser Gly Ser Glu Thr Pro Gly Thr Ser Glu Ser Ala Thr Pro Glu Ser
1               5                   10                  15

<210> SEQ ID NO 28
<211> LENGTH: 119
<212> TYPE: PRT
<213> ORGANISM: Homo sapiens
<220> FEATURE:
<221> NAME/KEY: misc_feature
<222> LOCATION: (1)..(119)
<223> OTHER INFORMATION: B2M

<400> SEQUENCE: 28

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
                20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
        50                  55                  60

Arg Ile Glu Lys Val Glu His Ser Asp Leu Ser Phe Ser Lys Asp Trp
65                  70                  75                  80
```

```
Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 29
<211> LENGTH: 20
<212> TYPE: PRT
<213> ORGANISM: Artificial Sequence
<220> FEATURE:
<223> OTHER INFORMATION: Synthetic: H. sapiens partial, B2M signal
      sequence

<400> SEQUENCE: 29

Met Ser Arg Ser Val Ala Leu Ala Val Leu Ala Leu Leu Ser Leu Ser
1               5                   10                  15

Gly Leu Glu Ala
            20

<210> SEQ ID NO 30
<211> LENGTH: 99
<212> TYPE: PRT
<213> ORGANISM: Artificial Sequence
<220> FEATURE:
<223> OTHER INFORMATION: Synthetic: H. sapiens partial, B2M mature

<400> SEQUENCE: 30

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 31
<211> LENGTH: 358
<212> TYPE: PRT
<213> ORGANISM: Homo sapiens
<220> FEATURE:
<221> NAME/KEY: misc_feature
<222> LOCATION: (1)..(358)
<223> OTHER INFORMATION: HLA-E

<400> SEQUENCE: 31

Met Val Asp Gly Thr Leu Leu Leu Leu Ser Glu Ala Leu Ala Leu
1               5                   10                  15

Thr Gln Thr Trp Ala Gly Ser His Ser Leu Lys Tyr Phe His Thr Ser
            20                  25                  30

Val Ser Arg Pro Gly Arg Gly Glu Pro Arg Phe Ile Ser Val Gly Tyr
        35                  40                  45

Val Asp Asp Thr Gln Phe Val Arg Phe Asp Asn Asp Ala Ala Ser Pro
    50                  55                  60
```

```
Arg Met Val Pro Arg Ala Pro Trp Met Glu Gln Glu Gly Ser Glu Tyr
 65                  70                  75                  80

Trp Asp Arg Glu Thr Arg Ser Ala Arg Asp Thr Ala Gln Ile Phe Arg
                 85                  90                  95

Val Asn Leu Arg Thr Leu Arg Gly Tyr Tyr Asn Gln Ser Glu Ala Gly
            100                 105                 110

Ser His Thr Leu Gln Trp Met His Gly Cys Glu Leu Gly Pro Asp Arg
            115                 120                 125

Arg Phe Leu Arg Gly Tyr Glu Gln Phe Ala Tyr Asp Gly Lys Asp Tyr
130                 135                 140

Leu Thr Leu Asn Glu Asp Leu Arg Ser Trp Thr Ala Val Asp Thr Ala
145                 150                 155                 160

Ala Gln Ile Ser Glu Gln Lys Ser Asn Asp Ala Ser Glu Ala Glu His
                165                 170                 175

Gln Arg Ala Tyr Leu Glu Asp Thr Cys Val Glu Trp Leu His Lys Tyr
            180                 185                 190

Leu Glu Lys Gly Lys Glu Thr Leu Leu His Leu Glu Pro Pro Lys Thr
            195                 200                 205

His Val Thr His His Pro Ile Ser Asp His Glu Ala Thr Leu Arg Cys
210                 215                 220

Trp Ala Leu Gly Phe Tyr Pro Ala Glu Ile Thr Leu Thr Trp Gln Gln
225                 230                 235                 240

Asp Gly Glu Gly His Thr Gln Asp Thr Glu Leu Val Glu Thr Arg Pro
                245                 250                 255

Ala Gly Asp Gly Thr Phe Gln Lys Trp Ala Ala Val Val Val Pro Ser
            260                 265                 270

Gly Glu Glu Gln Arg Tyr Thr Cys His Val Gln His Glu Gly Leu Pro
            275                 280                 285

Glu Pro Val Thr Leu Arg Trp Lys Pro Ala Ser Gln Pro Thr Ile Pro
290                 295                 300

Ile Val Gly Ile Ile Ala Gly Leu Val Leu Leu Gly Ser Val Val Ser
305                 310                 315                 320

Gly Ala Val Val Ala Ala Val Ile Trp Arg Lys Lys Ser Ser Gly Gly
                325                 330                 335

Lys Gly Gly Ser Tyr Ser Lys Ala Glu Trp Ser Asp Ser Ala Gln Gly
            340                 345                 350

Ser Glu Ser His Ser Leu
            355

<210> SEQ ID NO 32
<211> LENGTH: 21
<212> TYPE: PRT
<213> ORGANISM: Artificial Sequence
<220> FEATURE:
<223> OTHER INFORMATION: Synthetic: H. sapiens partial, HLA-E signal
      sequence

<400> SEQUENCE: 32

Met Val Asp Gly Thr Leu Leu Leu Leu Ser Glu Ala Leu Ala Leu
 1               5                  10                  15

Thr Gln Thr Trp Ala
            20

<210> SEQ ID NO 33
<211> LENGTH: 337
<212> TYPE: PRT
```

<213> ORGANISM: Artificial Sequence
<220> FEATURE:
<223> OTHER INFORMATION: Synthetic: H. sapiens partial, HLA-E mature

<400> SEQUENCE: 33

Gly Ser His Ser Leu Lys Tyr Phe His Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Asn Asp Ala Ala Ser Pro Arg Met Val Pro Arg
        35                  40                  45

Ala Pro Trp Met Glu Gln Glu Gly Ser Glu Tyr Trp Asp Arg Glu Thr
    50                  55                  60

Arg Ser Ala Arg Asp Thr Ala Gln Ile Phe Arg Val Asn Leu Arg Thr
65                  70                  75                  80

Leu Arg Gly Tyr Tyr Asn Gln Ser Glu Ala Gly Ser His Thr Leu Gln
                85                  90                  95

Trp Met His Gly Cys Glu Leu Gly Pro Asp Arg Arg Phe Leu Arg Gly
            100                 105                 110

Tyr Glu Gln Phe Ala Tyr Asp Gly Lys Asp Tyr Leu Thr Leu Asn Glu
        115                 120                 125

Asp Leu Arg Ser Trp Thr Ala Val Asp Thr Ala Ala Gln Ile Ser Glu
    130                 135                 140

Gln Lys Ser Asn Asp Ala Ser Glu Ala Glu His Gln Arg Ala Tyr Leu
145                 150                 155                 160

Glu Asp Thr Cys Val Glu Trp Leu His Lys Tyr Leu Glu Lys Gly Lys
                165                 170                 175

Glu Thr Leu Leu His Leu Glu Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Gln Asp Gly Glu Gly His
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Glu Pro Val Thr Leu
            260                 265                 270

Arg Trp Lys Pro Ala Ser Gln Pro Thr Ile Pro Ile Val Gly Ile Ile
        275                 280                 285

Ala Gly Leu Val Leu Leu Gly Ser Val Val Ser Gly Ala Val Val Ala
    290                 295                 300

Ala Val Ile Trp Arg Lys Lys Ser Ser Gly Gly Lys Gly Gly Ser Tyr
305                 310                 315                 320

Ser Lys Ala Glu Trp Ser Asp Ser Ala Gln Gly Ser Glu Ser His Ser
                325                 330                 335

Leu

<210> SEQ ID NO 34
<211> LENGTH: 338
<212> TYPE: PRT
<213> ORGANISM: Homo sapiens
<220> FEATURE:
<221> NAME/KEY: misc_feature
<222> LOCATION: (1)..(338)

<223> OTHER INFORMATION: HLA-G

<400> SEQUENCE: 34

```
Met Val Val Met Ala Pro Arg Thr Leu Phe Leu Leu Leu Ser Gly Ala
1               5                   10                  15
Leu Thr Leu Thr Glu Thr Trp Ala Gly Ser His Ser Met Arg Tyr Phe
            20                  25                  30
Ser Ala Ala Val Ser Arg Pro Gly Arg Gly Glu Pro Arg Phe Ile Ala
        35                  40                  45
Met Gly Tyr Val Asp Asp Thr Gln Phe Val Arg Phe Asp Ser Asp Ser
    50                  55                  60
Ala Cys Pro Arg Met Glu Pro Arg Ala Pro Trp Val Glu Gln Glu Gly
65                  70                  75                  80
Pro Glu Tyr Trp Glu Glu Glu Thr Arg Asn Thr Lys Ala His Ala Gln
                85                  90                  95
Thr Asp Arg Met Asn Leu Gln Thr Leu Arg Gly Tyr Tyr Asn Gln Ser
            100                 105                 110
Glu Ala Ser Ser His Thr Leu Gln Trp Met Ile Gly Cys Asp Leu Gly
        115                 120                 125
Ser Asp Gly Arg Leu Leu Arg Gly Tyr Glu Gln Tyr Ala Tyr Asp Gly
    130                 135                 140
Lys Asp Tyr Leu Ala Leu Asn Glu Asp Leu Arg Ser Trp Thr Ala Ala
145                 150                 155                 160
Asp Thr Ala Ala Gln Ile Ser Lys Arg Lys Cys Glu Ala Ala Asn Val
                165                 170                 175
Ala Glu Gln Arg Arg Ala Tyr Leu Glu Gly Thr Cys Val Glu Trp Leu
            180                 185                 190
His Arg Tyr Leu Glu Asn Gly Lys Glu Met Leu Gln Arg Ala Asp Pro
        195                 200                 205
Pro Lys Thr His Val Thr His His Pro Val Phe Asp Tyr Glu Ala Thr
    210                 215                 220
Leu Arg Cys Trp Ala Leu Gly Phe Tyr Pro Ala Glu Ile Ile Leu Thr
225                 230                 235                 240
Trp Gln Arg Asp Gly Glu Asp Gln Thr Gln Asp Val Glu Leu Val Glu
                245                 250                 255
Thr Arg Pro Ala Gly Asp Gly Thr Phe Gln Lys Trp Ala Ala Val Val
            260                 265                 270
Val Pro Ser Gly Glu Glu Gln Arg Tyr Thr Cys His Val Gln His Glu
        275                 280                 285
Gly Leu Pro Glu Pro Leu Met Leu Arg Trp Lys Gln Ser Ser Leu Pro
    290                 295                 300
Thr Ile Pro Ile Met Gly Ile Val Ala Gly Leu Val Val Leu Ala Ala
305                 310                 315                 320
Val Val Thr Gly Ala Ala Val Ala Ala Val Leu Trp Arg Lys Lys Ser
                325                 330                 335
Ser Asp
```

<210> SEQ ID NO 35
<211> LENGTH: 24
<212> TYPE: PRT
<213> ORGANISM: Artificial Sequence
<220> FEATURE:
<223> OTHER INFORMATION: Synthetic: H. sapiens partial, HLA-G signal
      sequence
<220> FEATURE:
<221> NAME/KEY: misc_feature

```
<222> LOCATION: (1)..(24)
<223> OTHER INFORMATION: CD34

<400> SEQUENCE: 35

Met Val Val Met Ala Pro Arg Thr Leu Phe Leu Leu Ser Gly Ala
1               5                   10                  15

Leu Thr Leu Thr Glu Thr Trp Ala
            20

<210> SEQ ID NO 36
<211> LENGTH: 9
<212> TYPE: PRT
<213> ORGANISM: Artificial Sequence
<220> FEATURE:
<223> OTHER INFORMATION: Synthetic: H. sapiens partial, HLA-G signal
      sequence short

<400> SEQUENCE: 36

Val Met Ala Pro Arg Thr Leu Phe Leu
1               5

<210> SEQ ID NO 37
<211> LENGTH: 385
<212> TYPE: PRT
<213> ORGANISM: Homo sapiens

<400> SEQUENCE: 37

Met Leu Val Arg Arg Gly Ala Arg Ala Gly Pro Arg Met Pro Arg Gly
1               5                   10                  15

Trp Thr Ala Leu Cys Leu Leu Ser Leu Leu Pro Ser Gly Phe Met Ser
            20                  25                  30

Leu Asp Asn Asn Gly Thr Ala Thr Pro Glu Leu Pro Thr Gln Gly Thr
                35                  40                  45

Phe Ser Asn Val Ser Thr Asn Val Ser Tyr Gln Glu Thr Thr Thr Pro
    50                  55                  60

Ser Thr Leu Gly Ser Thr Ser Leu His Pro Val Ser Gln His Gly Asn
65                  70                  75                  80

Glu Ala Thr Thr Asn Ile Thr Glu Thr Thr Val Lys Phe Thr Ser Thr
                85                  90                  95

Ser Val Ile Thr Ser Val Tyr Gly Asn Thr Asn Ser Ser Val Gln Ser
                100                 105                 110

Gln Thr Ser Val Ile Ser Thr Val Phe Thr Thr Pro Ala Asn Val Ser
            115                 120                 125

Thr Pro Glu Thr Thr Leu Lys Pro Ser Leu Ser Pro Gly Asn Val Ser
        130                 135                 140

Asp Leu Ser Thr Thr Ser Thr Ser Leu Ala Thr Ser Pro Thr Lys Pro
145                 150                 155                 160

Tyr Thr Ser Ser Ser Pro Ile Leu Ser Asp Ile Lys Ala Glu Ile Lys
                165                 170                 175

Cys Ser Gly Ile Arg Glu Val Lys Leu Thr Gln Gly Ile Cys Leu Glu
                180                 185                 190

Gln Asn Lys Thr Ser Ser Cys Ala Glu Phe Lys Lys Asp Arg Gly Glu
            195                 200                 205

Gly Leu Ala Arg Val Leu Cys Gly Glu Glu Gln Ala Asp Ala Asp Ala
        210                 215                 220

Gly Ala Gln Val Cys Ser Leu Leu Leu Ala Gln Ser Glu Val Arg Pro
225                 230                 235                 240

Gln Cys Leu Leu Leu Val Leu Ala Asn Arg Thr Glu Ile Ser Ser Lys
```

```
                245                 250                 255
Leu Gln Leu Met Lys His Gln Ser Asp Leu Lys Lys Leu Gly Ile
            260                 265                 270

Leu Asp Phe Thr Glu Gln Asp Val Ala Ser His Gln Ser Tyr Ser Gln
                275                 280                 285

Lys Thr Leu Ile Ala Leu Val Thr Ser Gly Ala Leu Leu Ala Val Leu
            290                 295                 300

Gly Ile Thr Gly Tyr Phe Leu Met Asn Arg Arg Ser Trp Ser Pro Thr
305                 310                 315                 320

Gly Glu Arg Leu Gly Glu Asp Pro Tyr Tyr Thr Glu Asn Gly Gly Gly
                325                 330                 335

Gln Gly Tyr Ser Ser Gly Pro Gly Thr Ser Pro Glu Ala Gln Gly Lys
                340                 345                 350

Ala Ser Val Asn Arg Gly Ala Gln Glu Asn Gly Thr Gly Gln Ala Thr
                355                 360                 365

Ser Arg Asn Gly His Ser Ala Arg Gln His Val Val Ala Asp Thr Glu
            370                 375                 380

Leu
385

<210> SEQ ID NO 38
<211> LENGTH: 16
<212> TYPE: PRT
<213> ORGANISM: Artificial Sequence
<220> FEATURE:
<223> OTHER INFORMATION: Synthetic: H. sapiens partial, CD34 Q10 epitope

<400> SEQUENCE: 38

Glu Leu Pro Thr Gln Gly Thr Phe Ser Asn Val Ser Thr Asn Val Ser
1               5                   10                  15

<210> SEQ ID NO 39
<211> LENGTH: 489
<212> TYPE: PRT
<213> ORGANISM: Artificial Sequence
<220> FEATURE:
<223> OTHER INFORMATION: Synthetic: CD19 CAR

<400> SEQUENCE: 39

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
                20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
        50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
                100                 105                 110

Gly Asn Thr Leu Pro Tyr Thr Phe Gly Gly Gly Thr Lys Leu Glu Ile
            115                 120                 125

Thr Gly Ser Thr Ser Gly Ser Gly Lys Pro Gly Ser Gly Glu Gly Ser
        130                 135                 140
```

```
Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
            165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
            245                 250                 255

Trp Gly Gln Gly Thr Ser Val Thr Val Ser Ser Ala Ala Ile Glu
            260                 265                 270

Val Met Tyr Pro Pro Pro Tyr Leu Asp Asn Glu Lys Ser Asn Gly Thr
        275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
            325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
            355                 360                 365

Pro Arg Asp Phe Ala Ala Tyr Arg Ser Arg Val Lys Phe Ser Arg Ser
            370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 40
<211> LENGTH: 22
<212> TYPE: PRT
<213> ORGANISM: Artificial Sequence
<220> FEATURE:
<223> OTHER INFORMATION: Synthetic: H. sapiens partial, CAR signal
      sequence hGCMF

<400> SEQUENCE: 40

Met Leu Leu Leu Val Thr Ser Leu Leu Leu Cys Glu Leu Pro His Pro
1               5                   10                  15
```

Ala Phe Leu Leu Ile Pro
            20

<210> SEQ ID NO 41
<211> LENGTH: 244
<212> TYPE: PRT
<213> ORGANISM: Artificial Sequence
<220> FEATURE:
<223> OTHER INFORMATION: Synthetic: Anti-CD19 scFv

<400> SEQUENCE: 41

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser

<210> SEQ ID NO 42
<211> LENGTH: 42
<212> TYPE: PRT
<213> ORGANISM: Artificial Sequence
<220> FEATURE:
<223> OTHER INFORMATION: Synthetic: CAR hinge

<400> SEQUENCE: 42

Ala Ala Ala Ile Glu Val Met Tyr Pro Pro Pro Tyr Leu Asp Asn Glu
1               5                   10                  15

Lys Ser Asn Gly Thr Ile Ile His Val Lys Gly Lys His Leu Cys Pro
            20                  25                  30

Ser Pro Leu Phe Pro Gly Pro Ser Lys Pro
        35                  40

<210> SEQ ID NO 43
<211> LENGTH: 28
<212> TYPE: PRT
<213> ORGANISM: Artificial Sequence
<220> FEATURE:
<223> OTHER INFORMATION: Synthetic: H. sapiens partial, CAR TM

<400> SEQUENCE: 43

Phe Trp Val Leu Val Val Val Gly Gly Val Leu Ala Cys Tyr Ser Leu
1               5                   10                  15

Leu Val Thr Val Ala Phe Ile Ile Phe Trp Val Arg
            20                  25

<210> SEQ ID NO 44
<211> LENGTH: 19
<212> TYPE: PRT
<213> ORGANISM: Porcine teschovirus-1
<220> FEATURE:
<221> NAME/KEY: misc_feature
<222> LOCATION: (1)..(19)
<223> OTHER INFORMATION: P2A

<400> SEQUENCE: 44

Ala Thr Asn Phe Ser Leu Leu Lys Gln Ala Gly Asp Val Glu Glu Asn
1               5                   10                  15

Pro Gly Pro

<210> SEQ ID NO 45
<211> LENGTH: 18
<212> TYPE: PRT
<213> ORGANISM: Thosea asigna virus
<220> FEATURE:
<221> NAME/KEY: misc_feature
<222> LOCATION: (1)..(18)
<223> OTHER INFORMATION: T2A

<400> SEQUENCE: 45

Glu Gly Arg Gly Ser Leu Leu Thr Cys Gly Asp Val Glu Glu Asn Pro
1               5                   10                  15

Gly Pro

<210> SEQ ID NO 46
<211> LENGTH: 170
<212> TYPE: PRT
<213> ORGANISM: Artificial Sequence
<220> FEATURE:
<223> OTHER INFORMATION: Synthetic: H. sapiens partial, BCMA ECD TM ICD
      truncated I

<400> SEQUENCE: 46

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Gly Ser
65                  70                  75                  80

Gly Leu Leu Gly Met Ala Asn Ile Asp Leu Glu Lys Ser Arg Thr Gly
                85                  90                  95

-continued

```
Asp Glu Ile Ile Leu Pro Arg Gly Leu Glu Tyr Thr Val Glu Glu Cys
                100                 105                 110

Thr Cys Glu Asp Cys Ile Lys Ser Lys Pro Lys Val Asp Ser Asp His
            115                 120                 125

Cys Phe Pro Leu Pro Ala Met Glu Gly Ala Thr Ile Leu Val Thr
130                 135                 140

Thr Lys Thr Asn Asp Tyr Cys Lys Ser Leu Pro Ala Ala Leu Ser Ala
145                 150                 155                 160

Thr Glu Ile Glu Lys Ser Ile Ser Ala Arg
                165                 170

<210> SEQ ID NO 47
<211> LENGTH: 93
<212> TYPE: PRT
<213> ORGANISM: Artificial Sequence
<220> FEATURE:
<223> OTHER INFORMATION: Synthetic: H. sapiens partial, BCMA ECD TM ICD
      truncated II

<400> SEQUENCE: 47

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly
                85                  90

<210> SEQ ID NO 48
<211> LENGTH: 120
<212> TYPE: PRT
<213> ORGANISM: Artificial Sequence
<220> FEATURE:
<223> OTHER INFORMATION: Synthetic: BCMA ECD CD8 TM

<400> SEQUENCE: 48

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Thr Thr Thr Pro Ala Pro Arg Pro Pro Thr
50                  55                  60

Pro Ala Pro Thr Ile Ala Ser Gln Pro Leu Ser Leu Arg Pro Glu Ala
65                  70                  75                  80

Cys Arg Pro Ala Ala Gly Gly Ala Val His Thr Arg Gly Leu Asp Phe
                85                  90                  95

Ala Cys Asp Ile Tyr Ile Trp Ala Pro Leu Ala Gly Thr Cys Gly Val
                100                 105                 110

Leu Leu Leu Ser Leu Val Ile Thr
            115                 120
```

```
<210> SEQ ID NO 49
<211> LENGTH: 123
<212> TYPE: PRT
<213> ORGANISM: Artificial Sequence
<220> FEATURE:
<223> OTHER INFORMATION: Synthetic: BCMA ECD linker CD8TM

<400> SEQUENCE: 49

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ala Ala Thr Thr Pro Ala Pro Arg
    50                  55                  60

Pro Pro Thr Pro Ala Pro Thr Ile Ala Ser Gln Pro Leu Ser Leu Arg
65                  70                  75                  80

Pro Glu Ala Cys Arg Pro Ala Ala Gly Gly Ala Val His Thr Arg Gly
                85                  90                  95

Leu Asp Phe Ala Cys Asp Ile Tyr Ile Trp Ala Pro Leu Ala Gly Thr
            100                 105                 110

Cys Gly Val Leu Leu Leu Ser Leu Val Ile Thr
        115                 120

<210> SEQ ID NO 50
<211> LENGTH: 91
<212> TYPE: PRT
<213> ORGANISM: Artificial Sequence
<220> FEATURE:
<223> OTHER INFORMATION: Synthetic: BCMA ECD CD34 CD8TM

<400> SEQUENCE: 50

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Glu Leu Pro Thr Gln Gly Thr Phe Ser Asn
    50                  55                  60

Val Ser Thr Asn Val Ser Ile Tyr Ile Trp Ala Pro Leu Ala Gly Thr
65                  70                  75                  80

Cys Gly Val Leu Leu Leu Ser Leu Val Ile Thr
                85                  90

<210> SEQ ID NO 51
<211> LENGTH: 136
<212> TYPE: PRT
<213> ORGANISM: Artificial Sequence
<220> FEATURE:
<223> OTHER INFORMATION: Synthetic: BCMA ECD CD34 CD8 CD8TM

<400> SEQUENCE: 51

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
```

```
                    35                  40                  45
Val Lys Gly Thr Asn Ala Glu Leu Pro Thr Gln Gly Thr Phe Ser Asn
 50                  55                  60

Val Ser Thr Asn Val Ser Thr Thr Thr Pro Ala Pro Arg Pro Pro Thr
 65                  70                  75                  80

Pro Ala Pro Thr Ile Ala Ser Gln Pro Leu Ser Leu Arg Pro Glu Ala
                 85                  90                  95

Cys Arg Pro Ala Ala Gly Gly Ala Val His Thr Arg Gly Leu Asp Phe
                100                 105                 110

Ala Cys Asp Ile Tyr Ile Trp Ala Pro Leu Ala Gly Thr Cys Gly Val
                115                 120                 125

Leu Leu Leu Ser Leu Val Ile Thr
                130                 135

<210> SEQ ID NO 52
<211> LENGTH: 543
<212> TYPE: PRT
<213> ORGANISM: Artificial Sequence
<220> FEATURE:
<223> OTHER INFORMATION: Synthetic: scFv SM CAR signaling

<400> SEQUENCE: 52

Met Leu Leu Leu Val Thr Ser Leu Leu Leu Cys Glu Leu Pro His Pro
  1               5                  10                  15

Ala Phe Leu Leu Ile Pro Asp Ile Gln Met Thr Gln Thr Thr Ser Ser
                 20                  25                  30

Leu Ser Ala Ser Leu Gly Asp Arg Val Thr Ile Ser Cys Arg Ala Ser
                 35                  40                  45

Gln Asp Ile Ser Lys Tyr Leu Asn Trp Tyr Gln Gln Lys Pro Asp Gly
 50                  55                  60

Thr Val Lys Leu Leu Ile Tyr His Thr Ser Arg Leu His Ser Gly Val
 65                  70                  75                  80

Pro Ser Arg Phe Ser Gly Ser Gly Ser Gly Thr Asp Tyr Ser Leu Thr
                 85                  90                  95

Ile Ser Asn Leu Glu Gln Glu Asp Ile Ala Thr Tyr Phe Cys Gln Gln
                100                 105                 110

Gly Asn Thr Leu Pro Tyr Thr Phe Gly Gly Gly Thr Lys Leu Glu Ile
                115                 120                 125

Thr Gly Ser Thr Ser Gly Ser Gly Lys Pro Gly Ser Gly Glu Gly Ser
                130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
                180                 185                 190

Glu Trp Leu Gly Val Ile Trp Gly Ser Glu Thr Thr Tyr Tyr Asn Ser
                195                 200                 205

Ala Leu Lys Ser Arg Leu Thr Ile Ile Lys Asp Asn Ser Lys Ser Gln
                210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Met Leu Gln Met Ala
```

```
                260                 265                 270
Gly Gln Cys Ser Gln Asn Glu Tyr Phe Asp Ser Leu Leu His Ala Cys
            275                 280                 285

Ile Pro Cys Gln Leu Arg Cys Ser Ser Asn Thr Pro Pro Leu Thr Cys
            290                 295                 300

Gln Arg Tyr Cys Asn Ala Ser Val Thr Asn Ser Val Lys Gly Thr Asn
305                 310                 315                 320

Ala Ala Ala Ile Glu Val Met Tyr Pro Pro Tyr Leu Asp Asn
                325                 330                 335

Glu Lys Ser Asn Gly Thr Ile Ile His Val Lys Gly Lys His Leu Cys
            340                 345                 350

Pro Ser Pro Leu Phe Pro Gly Pro Ser Lys Pro Phe Trp Val Leu Val
            355                 360                 365

Val Val Gly Gly Val Leu Ala Cys Tyr Ser Leu Leu Val Thr Val Ala
            370                 375                 380

Phe Ile Ile Phe Trp Val Arg Ser Lys Arg Ser Arg Leu Leu His Ser
385                 390                 395                 400

Asp Tyr Met Asn Met Thr Pro Arg Arg Pro Gly Pro Thr Arg Lys His
                405                 410                 415

Tyr Gln Pro Tyr Ala Pro Pro Arg Asp Phe Ala Ala Tyr Arg Ser Arg
                420                 425                 430

Val Lys Phe Ser Arg Ser Ala Asp Ala Pro Ala Tyr Gln Gln Gly Gln
            435                 440                 445

Asn Gln Leu Tyr Asn Glu Leu Asn Leu Gly Arg Arg Glu Glu Tyr Asp
            450                 455                 460

Val Leu Asp Lys Arg Arg Gly Arg Asp Pro Glu Met Gly Gly Lys Pro
465                 470                 475                 480

Arg Arg Lys Asn Pro Gln Glu Gly Leu Tyr Asn Glu Leu Gln Lys Asp
                485                 490                 495

Lys Met Ala Glu Ala Tyr Ser Glu Ile Gly Met Lys Gly Glu Arg Arg
                500                 505                 510

Arg Gly Lys Gly His Asp Gly Leu Tyr Gln Gly Leu Ser Thr Ala Thr
            515                 520                 525

Lys Asp Thr Tyr Asp Ala Leu His Met Gln Ala Leu Pro Pro Arg
            530                 535                 540

<210> SEQ ID NO 53
<211> LENGTH: 521
<212> TYPE: PRT
<213> ORGANISM: Artificial Sequence
<220> FEATURE:
<223> OTHER INFORMATION: Synthetic: SM scFv CAR signaling

<400> SEQUENCE: 53

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Asp Ile Gln Met Thr Gln Thr Thr Ser Ser
        50                  55                  60

Leu Ser Ala Ser Leu Gly Asp Arg Val Thr Ile Ser Cys Arg Ala Ser
65                  70                  75                  80

Gln Asp Ile Ser Lys Tyr Leu Asn Trp Tyr Gln Gln Lys Pro Asp Gly
```

```
                    85                  90                  95
Thr Val Lys Leu Leu Ile Tyr His Thr Ser Arg Leu His Ser Gly Val
            100                 105                 110

Pro Ser Arg Phe Ser Gly Ser Gly Ser Gly Thr Asp Tyr Ser Leu Thr
            115                 120                 125

Ile Ser Asn Leu Glu Gln Glu Asp Ile Ala Thr Tyr Phe Cys Gln Gln
            130                 135                 140

Gly Asn Thr Leu Pro Tyr Thr Phe Gly Gly Thr Lys Leu Glu Ile
145                 150                 155                 160

Thr Gly Ser Thr Ser Gly Ser Gly Lys Pro Gly Ser Gly Glu Gly Ser
                165                 170                 175

Thr Lys Gly Glu Val Lys Leu Gln Glu Ser Gly Pro Gly Leu Val Ala
            180                 185                 190

Pro Ser Gln Ser Leu Ser Val Thr Cys Thr Val Ser Gly Val Ser Leu
            195                 200                 205

Pro Asp Tyr Gly Val Ser Trp Ile Arg Gln Pro Pro Arg Lys Gly Leu
            210                 215                 220

Glu Trp Leu Gly Val Ile Trp Gly Ser Glu Thr Thr Tyr Tyr Asn Ser
225                 230                 235                 240

Ala Leu Lys Ser Arg Leu Thr Ile Ile Lys Asp Asn Ser Lys Ser Gln
                245                 250                 255

Val Phe Leu Lys Met Asn Ser Leu Gln Thr Asp Asp Thr Ala Ile Tyr
            260                 265                 270

Tyr Cys Ala Lys His Tyr Tyr Gly Gly Ser Tyr Ala Met Asp Tyr
            275                 280                 285

Trp Gly Gln Gly Thr Ser Val Thr Val Ser Ser Ala Ala Ile Glu
            290                 295                 300

Val Met Tyr Pro Pro Pro Tyr Leu Asp Asn Glu Lys Ser Asn Gly Thr
305                 310                 315                 320

Ile Ile His Val Lys Gly Lys His Leu Cys Pro Ser Pro Leu Phe Pro
                325                 330                 335

Gly Pro Ser Lys Pro Phe Trp Val Leu Val Val Val Gly Gly Val Leu
            340                 345                 350

Ala Cys Tyr Ser Leu Leu Val Thr Val Ala Phe Ile Ile Phe Trp Val
            355                 360                 365

Arg Ser Lys Arg Ser Arg Leu Leu His Ser Asp Tyr Met Asn Met Thr
            370                 375                 380

Pro Arg Arg Pro Gly Pro Thr Arg Lys His Tyr Gln Pro Tyr Ala Pro
385                 390                 395                 400

Pro Arg Asp Phe Ala Ala Tyr Arg Ser Arg Val Lys Phe Ser Arg Ser
                405                 410                 415

Ala Asp Ala Pro Ala Tyr Gln Gln Gly Gln Asn Gln Leu Tyr Asn Glu
            420                 425                 430

Leu Asn Leu Gly Arg Arg Glu Glu Tyr Asp Val Leu Asp Lys Arg Arg
            435                 440                 445

Gly Arg Asp Pro Glu Met Gly Gly Lys Pro Arg Arg Lys Asn Pro Gln
450                 455                 460

Glu Gly Leu Tyr Asn Glu Leu Gln Lys Asp Lys Met Ala Glu Ala Tyr
465                 470                 475                 480

Ser Glu Ile Gly Met Lys Gly Glu Arg Arg Arg Gly Lys Gly His Asp
                485                 490                 495

Gly Leu Tyr Gln Gly Leu Ser Thr Ala Thr Lys Asp Thr Tyr Asp Ala
            500                 505                 510
```

Leu His Met Gln Ala Leu Pro Pro Arg
        515                 520

<210> SEQ ID NO 54
<211> LENGTH: 525
<212> TYPE: PRT
<213> ORGANISM: Artificial Sequence
<220> FEATURE:
<223> OTHER INFORMATION: Synthetic: scFvD1 SMS scFvD2 CAR signaling

<400> SEQUENCE: 54

Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Met Leu Gln Met Ala Gly Gln Cys Ser Gln Asn Glu Tyr Phe Asp
130                 135                 140

Ser Leu Leu His Ala Cys Ile Pro Cys Gln Leu Arg Cys Ser Ser Asn
145                 150                 155                 160

Thr Pro Pro Leu Thr Cys Gln Arg Tyr Cys Asn Ala Ser Val Thr Asn
                165                 170                 175

Ser Val Lys Gly Thr Asn Ala Glu Val Lys Leu Gln Glu Ser Gly Pro
            180                 185                 190

Gly Leu Val Ala Pro Ser Gln Ser Leu Ser Val Thr Cys Thr Val Ser
        195                 200                 205

Gly Val Ser Leu Pro Asp Tyr Gly Val Ser Trp Ile Arg Gln Pro Pro
    210                 215                 220

Arg Lys Gly Leu Glu Trp Leu Gly Val Ile Trp Gly Ser Glu Thr Thr
225                 230                 235                 240

Tyr Tyr Asn Ser Ala Leu Lys Ser Arg Leu Thr Ile Ile Lys Asp Asn
                245                 250                 255

Ser Lys Ser Gln Val Phe Leu Lys Met Asn Ser Leu Gln Thr Asp Asp
            260                 265                 270

Thr Ala Ile Tyr Tyr Cys Ala Lys His Tyr Tyr Gly Gly Ser Tyr
        275                 280                 285

Ala Met Asp Tyr Trp Gly Gln Gly Thr Ser Val Thr Val Ser Ser Ala
    290                 295                 300

Ala Ala Ile Glu Val Met Tyr Pro Pro Tyr Leu Asp Asn Glu Lys
305                 310                 315                 320

Ser Asn Gly Thr Ile Ile His Val Lys Gly Lys His Leu Cys Pro Ser
                325                 330                 335

Pro Leu Phe Pro Gly Pro Ser Lys Pro Phe Trp Val Leu Val Val Val
            340                 345                 350

Gly Gly Val Leu Ala Cys Tyr Ser Leu Leu Val Thr Val Ala Phe Ile
        355                 360                 365

Ile Phe Trp Val Arg Ser Lys Arg Ser Arg Leu Leu His Ser Asp Tyr
    370                 375                 380

Met Asn Met Thr Pro Arg Arg Pro Gly Pro Thr Arg Lys His Tyr Gln
385                 390                 395                 400

Pro Tyr Ala Pro Pro Arg Asp Phe Ala Ala Tyr Arg Ser Arg Val Lys
                405                 410                 415

Phe Ser Arg Ser Ala Asp Ala Pro Ala Tyr Gln Gln Gly Gln Asn Gln
                420                 425                 430

Leu Tyr Asn Glu Leu Asn Leu Gly Arg Arg Glu Glu Tyr Asp Val Leu
            435                 440                 445

Asp Lys Arg Arg Gly Arg Asp Pro Glu Met Gly Gly Lys Pro Arg Arg
450                 455                 460

Lys Asn Pro Gln Glu Gly Leu Tyr Asn Glu Leu Gln Lys Asp Lys Met
465                 470                 475                 480

Ala Glu Ala Tyr Ser Glu Ile Gly Met Lys Gly Glu Arg Arg Arg Gly
                485                 490                 495

Lys Gly His Asp Gly Leu Tyr Gln Gly Leu Ser Thr Ala Thr Lys Asp
                500                 505                 510

Thr Tyr Asp Ala Leu His Met Gln Ala Leu Pro Pro Arg
        515                 520                 525

<210> SEQ ID NO 55
<211> LENGTH: 575
<212> TYPE: PRT
<213> ORGANISM: Artificial Sequence
<220> FEATURE:
<223> OTHER INFORMATION: Synthetic: SS scFv SM CAR signaling

<400> SEQUENCE: 55

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Asp Ile Gln Met Thr Gln Thr Thr Ser Ser
    50                  55                  60

Leu Ser Ala Ser Leu Gly Asp Arg Val Thr Ile Ser Cys Arg Ala Ser
65                  70                  75                  80

Gln Asp Ile Ser Lys Tyr Leu Asn Trp Tyr Gln Gln Lys Pro Asp Gly
                85                  90                  95

Thr Val Lys Leu Leu Ile Tyr His Thr Ser Arg Leu His Ser Gly Val
            100                 105                 110

Pro Ser Arg Phe Ser Gly Ser Gly Ser Gly Thr Asp Tyr Ser Leu Thr
        115                 120                 125

Ile Ser Asn Leu Glu Gln Glu Asp Ile Ala Thr Tyr Phe Cys Gln Gln
    130                 135                 140

Gly Asn Thr Leu Pro Tyr Thr Phe Gly Gly Thr Lys Leu Glu Ile
145                 150                 155                 160

Thr Gly Ser Thr Ser Gly Ser Gly Lys Pro Gly Ser Gly Glu Gly Ser
                165                 170                 175

Thr Lys Gly Glu Val Lys Leu Gln Glu Ser Gly Pro Gly Leu Val Ala
            180                 185                 190

```
Pro Ser Gln Ser Leu Ser Val Thr Cys Thr Val Ser Gly Val Ser Leu
            195                 200                 205

Pro Asp Tyr Gly Val Ser Trp Ile Arg Gln Pro Pro Arg Lys Gly Leu
210                 215                 220

Glu Trp Leu Gly Val Ile Trp Gly Ser Glu Thr Thr Tyr Tyr Asn Ser
225                 230                 235                 240

Ala Leu Lys Ser Arg Leu Thr Ile Ile Lys Asp Asn Ser Lys Ser Gln
            245                 250                 255

Val Phe Leu Lys Met Asn Ser Leu Gln Thr Asp Asp Thr Ala Ile Tyr
            260                 265                 270

Tyr Cys Ala Lys His Tyr Tyr Gly Gly Ser Tyr Ala Met Asp Tyr
            275                 280                 285

Trp Gly Gln Gly Thr Ser Val Thr Val Ser Ser Met Leu Gln Met Ala
            290                 295                 300

Gly Gln Cys Ser Gln Asn Glu Tyr Phe Asp Ser Leu Leu His Ala Cys
305                 310                 315                 320

Ile Pro Cys Gln Leu Arg Cys Ser Ser Asn Thr Pro Pro Leu Thr Cys
            325                 330                 335

Gln Arg Tyr Cys Asn Ala Ser Val Thr Asn Ser Val Lys Gly Thr Asn
            340                 345                 350

Ala Ala Ala Ile Glu Val Met Tyr Pro Pro Tyr Leu Asp Asn
            355                 360                 365

Glu Lys Ser Asn Gly Thr Ile Ile His Val Lys Gly Lys His Leu Cys
            370                 375                 380

Pro Ser Pro Leu Phe Pro Gly Pro Ser Lys Pro Phe Trp Val Leu Val
385                 390                 395                 400

Val Val Gly Gly Val Leu Ala Cys Tyr Ser Leu Leu Val Thr Val Ala
            405                 410                 415

Phe Ile Ile Phe Trp Val Arg Ser Lys Arg Ser Arg Leu Leu His Ser
            420                 425                 430

Asp Tyr Met Asn Met Thr Pro Arg Arg Pro Gly Pro Thr Arg Lys His
            435                 440                 445

Tyr Gln Pro Tyr Ala Pro Pro Arg Asp Phe Ala Ala Tyr Arg Ser Arg
450                 455                 460

Val Lys Phe Ser Arg Ser Ala Asp Ala Pro Ala Tyr Gln Gln Gly Gln
465                 470                 475                 480

Asn Gln Leu Tyr Asn Glu Leu Asn Leu Gly Arg Arg Glu Glu Tyr Asp
            485                 490                 495

Val Leu Asp Lys Arg Arg Gly Arg Asp Pro Glu Met Gly Gly Lys Pro
            500                 505                 510

Arg Arg Lys Asn Pro Gln Glu Gly Leu Tyr Asn Glu Leu Gln Lys Asp
            515                 520                 525

Lys Met Ala Glu Ala Tyr Ser Glu Ile Gly Met Lys Gly Glu Arg Arg
530                 535                 540

Arg Gly Lys Gly His Asp Gly Leu Tyr Gln Gly Leu Ser Thr Ala Thr
545                 550                 555                 560

Lys Asp Thr Tyr Asp Ala Leu His Met Gln Ala Leu Pro Pro Arg
            565                 570                 575

<210> SEQ ID NO 56
<211> LENGTH: 630
<212> TYPE: PRT
<213> ORGANISM: Artificial Sequence
<220> FEATURE:
```

<223> OTHER INFORMATION: Synthetic: CAR-T2A-BCMA suicide switch

<400> SEQUENCE: 56

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Ile Glu
            260                 265                 270

Val Met Tyr Pro Pro Pro Tyr Leu Asp Asn Glu Lys Ser Asn Gly Thr
        275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365

Pro Arg Asp Phe Ala Ala Tyr Arg Ser Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400
```

```
Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg Gly Ser Gly Glu Gly Arg Gly
                485                 490                 495

Ser Leu Leu Thr Cys Gly Asp Val Glu Glu Asn Pro Gly Pro Met Leu
            500                 505                 510

Gln Met Ala Gly Gln Cys Ser Gln Asn Glu Tyr Phe Asp Ser Leu Leu
        515                 520                 525

His Ala Cys Ile Pro Cys Gln Leu Arg Cys Ser Ser Asn Thr Pro Pro
    530                 535                 540

Leu Thr Cys Gln Arg Tyr Cys Asn Ala Ser Val Thr Asn Ser Val Lys
545                 550                 555                 560

Gly Thr Asn Ala Thr Thr Thr Pro Ala Pro Arg Pro Pro Thr Pro Ala
                565                 570                 575

Pro Thr Ile Ala Ser Gln Pro Leu Ser Leu Arg Pro Glu Ala Cys Arg
            580                 585                 590

Pro Ala Ala Gly Gly Ala Val His Thr Arg Gly Leu Asp Phe Ala Cys
        595                 600                 605

Asp Ile Tyr Ile Trp Ala Pro Leu Ala Gly Thr Cys Gly Val Leu Leu
    610                 615                 620

Leu Ser Leu Val Ile Thr
625                 630

<210> SEQ ID NO 57
<211> LENGTH: 480
<212> TYPE: PRT
<213> ORGANISM: Artificial Sequence
<220> FEATURE:
<223> OTHER INFORMATION: Synthetic: HLA-G/B2M/HLA-E fusion

<400> SEQUENCE: 57

Val Met Ala Pro Arg Thr Leu Phe Leu Gly Gly Gly Ser Gly Gly
1               5                   10                  15

Gly Gly Ser Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Gly Ser
        115                 120                 125
```

Gly Gly Gly Ser Gly Gly Gly Ser Gly Gly Gly Ser Gly
    130             135             140

Ser His Ser Leu Lys Tyr Phe His Thr Ser Val Ser Arg Pro Gly Arg
145             150                 155                 160

Gly Glu Pro Arg Phe Ile Ser Val Gly Tyr Val Asp Asp Thr Gln Phe
                165                 170                 175

Val Arg Phe Asp Asn Asp Ala Ala Ser Pro Arg Met Val Pro Arg Ala
            180                 185                 190

Pro Trp Met Glu Gln Glu Gly Ser Glu Tyr Trp Asp Arg Glu Thr Arg
        195                 200                 205

Ser Ala Arg Asp Thr Ala Gln Ile Phe Arg Val Asn Leu Arg Thr Leu
210                 215                 220

Arg Gly Tyr Tyr Asn Gln Ser Glu Ala Gly Ser His Thr Leu Gln Trp
225                 230                 235                 240

Met His Gly Cys Glu Leu Gly Pro Asp Arg Arg Phe Leu Arg Gly Tyr
                245                 250                 255

Glu Gln Phe Ala Tyr Asp Gly Lys Asp Tyr Leu Thr Leu Asn Glu Asp
                260                 265                 270

Leu Arg Ser Trp Thr Ala Val Asp Thr Ala Ala Gln Ile Ser Glu Gln
            275                 280                 285

Lys Ser Asn Asp Ala Ser Glu Ala Glu His Gln Arg Ala Tyr Leu Glu
        290                 295                 300

Asp Thr Cys Val Glu Trp Leu His Lys Tyr Leu Glu Lys Gly Lys Glu
305                 310                 315                 320

Thr Leu Leu His Leu Glu Pro Pro Lys Thr His Val Thr His His Pro
                325                 330                 335

Ile Ser Asp His Glu Ala Thr Leu Arg Cys Trp Ala Leu Gly Phe Tyr
                340                 345                 350

Pro Ala Glu Ile Thr Leu Thr Trp Gln Gln Asp Gly Glu Gly His Thr
            355                 360                 365

Gln Asp Thr Glu Leu Val Glu Thr Arg Pro Ala Gly Asp Gly Thr Phe
        370                 375                 380

Gln Lys Trp Ala Ala Val Val Val Pro Ser Gly Glu Glu Gln Arg Tyr
385                 390                 395                 400

Thr Cys His Val Gln His Glu Gly Leu Pro Glu Pro Val Thr Leu Arg
                405                 410                 415

Trp Lys Pro Ala Ser Gln Pro Thr Ile Pro Ile Val Gly Ile Ile Ala
                420                 425                 430

Gly Leu Val Leu Leu Gly Ser Val Val Ser Gly Ala Val Val Ala Ala
            435                 440                 445

Val Ile Trp Arg Lys Lys Ser Ser Gly Gly Lys Gly Gly Ser Tyr Ser
450                 455                 460

Lys Ala Glu Trp Ser Asp Ser Ala Gln Gly Ser Glu Ser His Ser Leu
465                 470                 475                 480

<210> SEQ ID NO 58
<211> LENGTH: 456
<212> TYPE: PRT
<213> ORGANISM: Artificial Sequence
<220> FEATURE:
<223> OTHER INFORMATION: Synthetic: B2M/HLA-E fusion

<400> SEQUENCE: 58

Ile Gln Arg Thr Pro Lys Ile Gln Val Tyr Ser Arg His Pro Ala Glu
1               5                   10                  15

-continued

```
Asn Gly Lys Ser Asn Phe Leu Asn Cys Tyr Val Ser Gly Phe His Pro
             20                  25                  30
Ser Asp Ile Glu Val Asp Leu Leu Lys Asn Gly Glu Arg Ile Glu Lys
         35                  40                  45
Val Glu His Ser Asp Leu Ser Phe Ser Lys Asp Trp Ser Phe Tyr Leu
 50                  55                  60
Leu Tyr Tyr Thr Glu Phe Thr Pro Thr Glu Lys Asp Glu Tyr Ala Cys
 65                  70                  75                  80
Arg Val Asn His Val Thr Leu Ser Gln Pro Lys Ile Val Lys Trp Asp
                 85                  90                  95
Arg Asp Met Gly Gly Gly Ser Gly Gly Gly Ser Gly Gly Gly
             100                 105                 110
Gly Ser Gly Gly Gly Ser Gly Ser His Ser Leu Lys Tyr Phe His
         115                 120                 125
Thr Ser Val Ser Arg Pro Gly Arg Gly Glu Pro Arg Phe Ile Ser Val
 130                 135                 140
Gly Tyr Val Asp Asp Thr Gln Phe Val Arg Phe Asp Asn Asp Ala Ala
 145                 150                 155                 160
Ser Pro Arg Met Val Pro Arg Ala Pro Trp Met Glu Gln Glu Gly Ser
             165                 170                 175
Glu Tyr Trp Asp Arg Glu Thr Arg Ser Ala Arg Asp Thr Ala Gln Ile
             180                 185                 190
Phe Arg Val Asn Leu Arg Thr Leu Arg Gly Tyr Tyr Asn Gln Ser Glu
                 195                 200                 205
Ala Gly Ser His Thr Leu Gln Trp Met His Gly Cys Glu Leu Gly Pro
 210                 215                 220
Asp Arg Arg Phe Leu Arg Gly Tyr Glu Gln Phe Ala Tyr Asp Gly Lys
 225                 230                 235                 240
Asp Tyr Leu Thr Leu Asn Glu Asp Leu Arg Ser Trp Thr Ala Val Asp
             245                 250                 255
Thr Ala Ala Gln Ile Ser Glu Gln Lys Ser Asn Asp Ala Ser Glu Ala
             260                 265                 270
Glu His Gln Arg Ala Tyr Leu Glu Asp Thr Cys Val Glu Trp Leu His
             275                 280                 285
Lys Tyr Leu Glu Lys Gly Lys Glu Thr Leu Leu His Leu Glu Pro Pro
 290                 295                 300
Lys Thr His Val Thr His His Pro Ile Ser Asp His Glu Ala Thr Leu
 305                 310                 315                 320
Arg Cys Trp Ala Leu Gly Phe Tyr Pro Ala Glu Ile Thr Leu Thr Trp
             325                 330                 335
Gln Gln Asp Gly Glu Gly His Thr Gln Asp Thr Glu Leu Val Glu Thr
             340                 345                 350
Arg Pro Ala Gly Asp Gly Thr Phe Gln Lys Trp Ala Ala Val Val Val
             355                 360                 365
Pro Ser Gly Glu Glu Gln Arg Tyr Thr Cys His Val Gln His Glu Gly
 370                 375                 380
Leu Pro Glu Pro Val Thr Leu Arg Trp Lys Pro Ala Ser Gln Pro Thr
 385                 390                 395                 400
Ile Pro Ile Val Gly Ile Ile Ala Gly Leu Val Leu Leu Gly Ser Val
             405                 410                 415
Val Ser Gly Ala Val Val Ala Val Ile Trp Arg Lys Lys Ser Ser
             420                 425                 430
Gly Gly Lys Gly Gly Ser Tyr Ser Lys Ala Glu Trp Ser Asp Ser Ala
```

-continued

```
                435                 440                 445
Gln Gly Ser Glu Ser His Ser Leu
    450                 455

<210> SEQ ID NO 59
<211> LENGTH: 525
<212> TYPE: PRT
<213> ORGANISM: Artificial Sequence
<220> FEATURE:
<223> OTHER INFORMATION: Synthetic: HLA-G/BCMA/B2M/HLA-E fusion

<400> SEQUENCE: 59

Val Met Ala Pro Arg Thr Leu Phe Leu Gly Ser Gly Met Leu Gln Met
1               5                   10                  15

Ala Gly Gln Cys Ser Gln Asn Glu Tyr Phe Asp Ser Leu Leu His Ala
            20                  25                  30

Cys Ile Pro Cys Gln Leu Arg Cys Ser Ser Asn Thr Pro Pro Leu Thr
        35                  40                  45

Cys Gln Arg Tyr Cys Asn Ala Ser Val Thr Asn Ser Val Lys Gly Thr
    50                  55                  60

Asn Ala Gly Ser Gly Ile Gln Arg Thr Pro Lys Ile Gln Val Tyr Ser
65                  70                  75                  80

Arg His Pro Ala Glu Asn Gly Lys Ser Asn Phe Leu Asn Cys Tyr Val
                85                  90                  95

Ser Gly Phe His Pro Ser Asp Ile Glu Val Asp Leu Leu Lys Asn Gly
            100                 105                 110

Glu Arg Ile Glu Lys Val Glu His Ser Asp Leu Ser Phe Ser Lys Asp
        115                 120                 125

Trp Ser Phe Tyr Leu Leu Tyr Tyr Thr Glu Phe Thr Pro Thr Glu Lys
    130                 135                 140

Asp Glu Tyr Ala Cys Arg Val Asn His Val Thr Leu Ser Gln Pro Lys
145                 150                 155                 160

Ile Val Lys Trp Asp Arg Asp Met Gly Gly Gly Gly Ser Gly Gly Gly
                165                 170                 175

Gly Ser Gly Gly Gly Gly Ser Gly Gly Gly Gly Ser Gly Ser His Ser
            180                 185                 190

Leu Lys Tyr Phe His Thr Ser Val Ser Arg Pro Gly Arg Gly Glu Pro
        195                 200                 205

Arg Phe Ile Ser Val Gly Tyr Val Asp Asp Thr Gln Phe Val Arg Phe
    210                 215                 220

Asp Asn Asp Ala Ala Ser Pro Arg Met Val Pro Arg Ala Pro Trp Met
225                 230                 235                 240

Glu Gln Glu Gly Ser Glu Tyr Trp Asp Arg Glu Thr Arg Ser Ala Arg
                245                 250                 255

Asp Thr Ala Gln Ile Phe Arg Val Asn Leu Arg Thr Leu Arg Gly Tyr
            260                 265                 270

Tyr Asn Gln Ser Glu Ala Gly Ser His Thr Leu Gln Trp Met His Gly
        275                 280                 285

Cys Glu Leu Gly Pro Asp Arg Arg Phe Leu Arg Gly Tyr Glu Gln Phe
    290                 295                 300

Ala Tyr Asp Gly Lys Asp Tyr Leu Thr Leu Asn Glu Asp Leu Arg Ser
305                 310                 315                 320

Trp Thr Ala Val Asp Thr Ala Ala Gln Ile Ser Glu Gln Lys Ser Asn
                325                 330                 335

Asp Ala Ser Glu Ala Glu His Gln Arg Ala Tyr Leu Glu Asp Thr Cys
```

```
                   340                 345                 350
Val Glu Trp Leu His Lys Tyr Leu Glu Lys Gly Lys Glu Thr Leu Leu
            355                 360                 365

His Leu Glu Pro Pro Lys Thr His Val Thr His His Pro Ile Ser Asp
        370                 375                 380

His Glu Ala Thr Leu Arg Cys Trp Ala Leu Gly Phe Tyr Pro Ala Glu
385                 390                 395                 400

Ile Thr Leu Thr Trp Gln Gln Asp Gly Glu Gly His Thr Gln Asp Thr
                405                 410                 415

Glu Leu Val Glu Thr Arg Pro Ala Gly Asp Gly Thr Phe Gln Lys Trp
            420                 425                 430

Ala Ala Val Val Val Pro Ser Gly Glu Glu Gln Arg Tyr Thr Cys His
        435                 440                 445

Val Gln His Glu Gly Leu Pro Glu Pro Val Thr Leu Arg Trp Lys Pro
    450                 455                 460

Ala Ser Gln Pro Thr Ile Pro Ile Val Gly Ile Ile Ala Gly Leu Val
465                 470                 475                 480

Leu Leu Gly Ser Val Val Ser Gly Ala Val Ala Ala Val Ile Trp
                485                 490                 495

Arg Lys Lys Ser Ser Gly Gly Lys Gly Gly Ser Tyr Ser Lys Ala Glu
            500                 505                 510

Trp Ser Asp Ser Ala Gln Gly Ser Glu Ser His Ser Leu
        515                 520                 525

<210> SEQ ID NO 60
<211> LENGTH: 520
<212> TYPE: PRT
<213> ORGANISM: Artificial Sequence
<220> FEATURE:
<223> OTHER INFORMATION: Synthetic: HLA-G/B2M/BCMA/HLA-E fusion

<400> SEQUENCE: 60

Val Met Ala Pro Arg Thr Leu Phe Leu Gly Gly Gly Gly Ser Gly Gly
1               5                   10                  15

Gly Gly Ser Gly Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Ser Gly Met Leu
        115                 120                 125

Gln Met Ala Gly Gln Cys Ser Gln Asn Glu Tyr Phe Asp Ser Leu Leu
    130                 135                 140

His Ala Cys Ile Pro Cys Gln Leu Arg Cys Ser Ser Asn Thr Pro Pro
145                 150                 155                 160

Leu Thr Cys Gln Arg Tyr Cys Asn Ala Ser Val Thr Asn Ser Val Lys
                165                 170                 175

Gly Thr Asn Ala Gly Ser Gly Gly Ser His Ser Leu Lys Tyr Phe His
```

```
                180             185             190
Thr Ser Val Ser Arg Pro Gly Arg Gly Glu Pro Arg Phe Ile Ser Val
            195             200             205
Gly Tyr Val Asp Asp Thr Gln Phe Val Arg Phe Asp Asn Asp Ala Ala
            210             215             220
Ser Pro Arg Met Val Pro Arg Ala Pro Trp Met Glu Gln Glu Gly Ser
225             230             235             240
Glu Tyr Trp Asp Arg Glu Thr Arg Ser Ala Arg Asp Thr Ala Gln Ile
            245             250             255
Phe Arg Val Asn Leu Arg Thr Leu Arg Gly Tyr Tyr Asn Gln Ser Glu
            260             265             270
Ala Gly Ser His Thr Leu Gln Trp Met His Gly Cys Glu Leu Gly Pro
            275             280             285
Asp Arg Arg Phe Leu Arg Gly Tyr Glu Gln Phe Ala Tyr Asp Gly Lys
            290             295             300
Asp Tyr Leu Thr Leu Asn Glu Asp Leu Arg Ser Trp Thr Ala Val Asp
305             310             315             320
Thr Ala Ala Gln Ile Ser Glu Gln Lys Ser Asn Asp Ala Ser Glu Ala
            325             330             335
Glu His Gln Arg Ala Tyr Leu Glu Asp Thr Cys Val Glu Trp Leu His
            340             345             350
Lys Tyr Leu Glu Lys Gly Lys Glu Thr Leu Leu His Leu Glu Pro Pro
            355             360             365
Lys Thr His Val Thr His His Pro Ile Ser Asp His Glu Ala Thr Leu
            370             375             380
Arg Cys Trp Ala Leu Gly Phe Tyr Pro Ala Glu Ile Thr Leu Thr Trp
385             390             395             400
Gln Gln Asp Gly Glu Gly His Thr Gln Asp Thr Glu Leu Val Glu Thr
            405             410             415
Arg Pro Ala Gly Asp Gly Thr Phe Gln Lys Trp Ala Ala Val Val Val
            420             425             430
Pro Ser Gly Glu Glu Gln Arg Tyr Thr Cys His Val Gln His Glu Gly
            435             440             445
Leu Pro Glu Pro Val Thr Leu Arg Trp Lys Pro Ala Ser Gln Pro Thr
            450             455             460
Ile Pro Ile Val Gly Ile Ile Ala Gly Leu Val Leu Leu Gly Ser Val
465             470             475             480
Val Ser Gly Ala Val Val Ala Ala Val Ile Trp Arg Lys Lys Ser Ser
            485             490             495
Gly Gly Lys Gly Gly Ser Tyr Ser Lys Ala Glu Trp Ser Asp Ser Ala
            500             505             510
Gln Gly Ser Glu Ser His Ser Leu
            515             520

<210> SEQ ID NO 61
<211> LENGTH: 553
<212> TYPE: PRT
<213> ORGANISM: Artificial Sequence
<220> FEATURE:
<223> OTHER INFORMATION: Synthetic: HLA-G/BCMA/B2M/BCMA/HLA-E fusion

<400> SEQUENCE: 61

Val Met Ala Pro Arg Thr Leu Phe Leu Met Leu Gln Met Ala Gly Gln
1               5               10              15

Cys Ser Gln Asn Glu Tyr Phe Asp Ser Leu Leu His Ala Cys Ile Pro
```

```
            20                  25                  30
Cys Gln Leu Arg Cys Ser Ser Asn Thr Pro Leu Thr Cys Gln Arg
            35                  40                  45
Tyr Cys Asn Ala Ser Val Thr Asn Ser Val Lys Gly Thr Asn Ala Ile
50                  55                  60
Gln Arg Thr Pro Lys Ile Gln Val Tyr Ser Arg His Pro Ala Glu Asn
65                  70                  75                  80
Gly Lys Ser Asn Phe Leu Asn Cys Tyr Val Ser Gly Phe His Pro Ser
                85                  90                  95
Asp Ile Glu Val Asp Leu Leu Lys Asn Gly Glu Arg Ile Glu Lys Val
            100                 105                 110
Glu His Ser Asp Leu Ser Phe Ser Lys Asp Trp Ser Phe Tyr Leu Leu
            115                 120                 125
Tyr Tyr Thr Glu Phe Thr Pro Thr Glu Lys Asp Glu Tyr Ala Cys Arg
            130                 135                 140
Val Asn His Val Thr Leu Ser Gln Pro Lys Ile Val Lys Trp Asp Arg
145                 150                 155                 160
Asp Met Met Leu Gln Met Ala Gly Gln Cys Ser Gln Asn Glu Tyr Phe
                165                 170                 175
Asp Ser Leu Leu His Ala Cys Ile Pro Cys Gln Leu Arg Cys Ser Ser
            180                 185                 190
Asn Thr Pro Pro Leu Thr Cys Gln Arg Tyr Cys Asn Ala Ser Val Thr
            195                 200                 205
Asn Ser Val Lys Gly Thr Asn Ala Gly Ser His Ser Leu Lys Tyr Phe
210                 215                 220
His Thr Ser Val Ser Arg Pro Gly Arg Gly Glu Pro Arg Phe Ile Ser
225                 230                 235                 240
Val Gly Tyr Val Asp Asp Thr Gln Phe Val Arg Phe Asp Asn Asp Ala
                245                 250                 255
Ala Ser Pro Arg Met Val Pro Arg Ala Pro Trp Met Glu Gln Glu Gly
            260                 265                 270
Ser Glu Tyr Trp Asp Arg Glu Thr Arg Ser Ala Arg Asp Thr Ala Gln
            275                 280                 285
Ile Phe Arg Val Asn Leu Arg Thr Leu Arg Gly Tyr Tyr Asn Gln Ser
            290                 295                 300
Glu Ala Gly Ser His Thr Leu Gln Trp Met His Gly Cys Glu Leu Gly
305                 310                 315                 320
Pro Asp Arg Arg Phe Leu Arg Gly Tyr Glu Gln Phe Ala Tyr Asp Gly
                325                 330                 335
Lys Asp Tyr Leu Thr Leu Asn Glu Asp Leu Arg Ser Trp Thr Ala Val
            340                 345                 350
Asp Thr Ala Ala Gln Ile Ser Glu Gln Lys Ser Asn Asp Ala Ser Glu
            355                 360                 365
Ala Glu His Gln Arg Ala Tyr Leu Glu Asp Thr Cys Val Glu Trp Leu
            370                 375                 380
His Lys Tyr Leu Glu Lys Gly Lys Glu Thr Leu Leu His Leu Glu Pro
385                 390                 395                 400
Pro Lys Thr His Val Thr His His Pro Ile Ser Asp His Glu Ala Thr
            405                 410                 415
Leu Arg Cys Trp Ala Leu Gly Phe Tyr Pro Ala Glu Ile Thr Leu Thr
            420                 425                 430
Trp Gln Gln Asp Gly Glu Gly His Thr Gln Asp Thr Glu Leu Val Glu
            435                 440                 445
```

-continued

```
Thr Arg Pro Ala Gly Asp Gly Thr Phe Gln Lys Trp Ala Ala Val Val
    450                 455                 460

Val Pro Ser Gly Glu Glu Gln Arg Tyr Thr Cys His Val Gln His Glu
465                 470                 475                 480

Gly Leu Pro Glu Pro Val Thr Leu Arg Trp Lys Pro Ala Ser Gln Pro
                485                 490                 495

Thr Ile Pro Ile Val Gly Ile Ile Ala Gly Leu Val Leu Leu Gly Ser
                500                 505                 510

Val Val Ser Gly Ala Val Val Ala Ala Val Ile Trp Arg Lys Lys Ser
        515                 520                 525

Ser Gly Gly Lys Gly Gly Ser Tyr Ser Lys Ala Glu Trp Ser Asp Ser
530                 535                 540

Ala Gln Gly Ser Glu Ser His Ser Leu
545                 550
```

<210> SEQ ID NO 62
<211> LENGTH: 513
<212> TYPE: PRT
<213> ORGANISM: Artificial Sequence
<220> FEATURE:
<223> OTHER INFORMATION: Synthetic: BCMA/B2M/HLA-E fusion

<400> SEQUENCE: 62

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Gly Ser Gly Ile Gln Arg Thr Pro Lys Ile
50                  55                  60

Gln Val Tyr Ser Arg His Pro Ala Glu Asn Gly Lys Ser Asn Phe Leu
65                  70                  75                  80

Asn Cys Tyr Val Ser Gly Phe His Pro Ser Asp Ile Glu Val Asp Leu
                85                  90                  95

Leu Lys Asn Gly Glu Arg Ile Glu Lys Val Glu His Ser Asp Leu Ser
            100                 105                 110

Phe Ser Lys Asp Trp Ser Phe Tyr Leu Leu Tyr Tyr Thr Glu Phe Thr
        115                 120                 125

Pro Thr Glu Lys Asp Glu Tyr Ala Cys Arg Val Asn His Val Thr Leu
    130                 135                 140

Ser Gln Pro Lys Ile Val Lys Trp Asp Arg Asp Met Gly Gly Gly Gly
145                 150                 155                 160

Ser Gly Gly Gly Gly Ser Gly Gly Gly Ser Gly Gly Gly Gly Ser
                165                 170                 175

Gly Ser His Ser Leu Lys Tyr Phe His Thr Ser Val Ser Arg Pro Gly
            180                 185                 190

Arg Gly Glu Pro Arg Phe Ile Ser Val Gly Tyr Val Asp Asp Thr Gln
        195                 200                 205

Phe Val Arg Phe Asp Asn Asp Ala Ala Ser Pro Arg Met Val Pro Arg
    210                 215                 220

Ala Pro Trp Met Glu Gln Glu Gly Ser Glu Tyr Trp Asp Arg Glu Thr
225                 230                 235                 240

Arg Ser Ala Arg Asp Thr Ala Gln Ile Phe Arg Val Asn Leu Arg Thr
                245                 250                 255
```

-continued

```
Leu Arg Gly Tyr Tyr Asn Gln Ser Glu Ala Gly Ser His Thr Leu Gln
            260                 265                 270

Trp Met His Gly Cys Glu Leu Gly Pro Asp Arg Arg Phe Leu Arg Gly
        275                 280                 285

Tyr Glu Gln Phe Ala Tyr Asp Gly Lys Asp Tyr Leu Thr Leu Asn Glu
    290                 295                 300

Asp Leu Arg Ser Trp Thr Ala Val Asp Thr Ala Ala Gln Ile Ser Glu
305                 310                 315                 320

Gln Lys Ser Asn Asp Ala Ser Glu Ala Glu His Gln Arg Ala Tyr Leu
                325                 330                 335

Glu Asp Thr Cys Val Glu Trp Leu His Lys Tyr Leu Glu Lys Gly Lys
            340                 345                 350

Glu Thr Leu Leu His Leu Glu Pro Pro Lys Thr His Val Thr His His
        355                 360                 365

Pro Ile Ser Asp His Glu Ala Thr Leu Arg Cys Trp Ala Leu Gly Phe
    370                 375                 380

Tyr Pro Ala Glu Ile Thr Leu Thr Trp Gln Gln Asp Gly Glu Gly His
385                 390                 395                 400

Thr Gln Asp Thr Glu Leu Val Glu Thr Arg Pro Ala Gly Asp Gly Thr
                405                 410                 415

Phe Gln Lys Trp Ala Ala Val Val Val Pro Ser Gly Glu Glu Gln Arg
            420                 425                 430

Tyr Thr Cys His Val Gln His Glu Gly Leu Pro Glu Pro Val Thr Leu
        435                 440                 445

Arg Trp Lys Pro Ala Ser Gln Pro Thr Ile Pro Ile Val Gly Ile Ile
    450                 455                 460

Ala Gly Leu Val Leu Leu Gly Ser Val Val Ser Gly Ala Val Val Ala
465                 470                 475                 480

Ala Val Ile Trp Arg Lys Lys Ser Ser Gly Gly Lys Gly Gly Ser Tyr
                485                 490                 495

Ser Lys Ala Glu Trp Ser Asp Ser Ala Gln Gly Ser Glu Ser His Ser
            500                 505                 510

Leu
```

<210> SEQ ID NO 63
<211> LENGTH: 682
<212> TYPE: PRT
<213> ORGANISM: Artificial Sequence
<220> FEATURE:
<223> OTHER INFORMATION: Synthetic: HLA-G/B2M/HLA-E 2A BCMA SM

<400> SEQUENCE: 63

```
Val Met Ala Pro Arg Thr Leu Phe Leu Gly Gly Gly Ser Gly Gly
1               5                   10                  15

Gly Gly Ser Gly Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95
```

-continued

```
Thr Glu Lys Asp Glu Tyr Ala Cys Arg Val Asn His Val Thr Leu Ser
            100                 105                 110
Gln Pro Lys Ile Val Lys Trp Asp Arg Asp Met Gly Gly Gly Gly Ser
        115                 120                 125
Gly Gly Gly Gly Ser Gly Gly Gly Ser Gly Gly Gly Gly Ser Gly
    130                 135                 140
Ser His Ser Leu Lys Tyr Phe His Thr Ser Val Ser Arg Pro Gly Arg
145                 150                 155                 160
Gly Glu Pro Arg Phe Ile Ser Val Gly Tyr Val Asp Asp Thr Gln Phe
                165                 170                 175
Val Arg Phe Asp Asn Asp Ala Ala Ser Pro Arg Met Val Pro Arg Ala
            180                 185                 190
Pro Trp Met Glu Gln Glu Gly Ser Glu Tyr Trp Asp Arg Glu Thr Arg
        195                 200                 205
Ser Ala Arg Asp Thr Ala Gln Ile Phe Arg Val Asn Leu Arg Thr Leu
    210                 215                 220
Arg Gly Tyr Tyr Asn Gln Ser Glu Ala Gly Ser His Thr Leu Gln Trp
225                 230                 235                 240
Met His Gly Cys Glu Leu Gly Pro Asp Arg Arg Phe Leu Arg Gly Tyr
                245                 250                 255
Glu Gln Phe Ala Tyr Asp Gly Lys Asp Tyr Leu Thr Leu Asn Glu Asp
            260                 265                 270
Leu Arg Ser Trp Thr Ala Val Asp Thr Ala Ala Gln Ile Ser Glu Gln
        275                 280                 285
Lys Ser Asn Asp Ala Ser Glu Ala Glu His Gln Arg Ala Tyr Leu Glu
    290                 295                 300
Asp Thr Cys Val Glu Trp Leu His Lys Tyr Leu Glu Lys Gly Lys Glu
305                 310                 315                 320
Thr Leu Leu His Leu Glu Pro Pro Lys Thr His Val Thr His His Pro
                325                 330                 335
Ile Ser Asp His Glu Ala Thr Leu Arg Cys Trp Ala Leu Gly Phe Tyr
            340                 345                 350
Pro Ala Glu Ile Thr Leu Thr Trp Gln Gln Asp Gly Glu Gly His Thr
        355                 360                 365
Gln Asp Thr Glu Leu Val Glu Thr Arg Pro Ala Gly Asp Gly Thr Phe
    370                 375                 380
Gln Lys Trp Ala Ala Val Val Val Pro Ser Gly Glu Glu Gln Arg Tyr
385                 390                 395                 400
Thr Cys His Val Gln His Glu Gly Leu Pro Glu Pro Val Thr Leu Arg
                405                 410                 415
Trp Lys Pro Ala Ser Gln Pro Thr Ile Pro Ile Val Gly Ile Ile Ala
            420                 425                 430
Gly Leu Val Leu Leu Gly Ser Val Val Ser Gly Ala Val Val Ala Ala
        435                 440                 445
Val Ile Trp Arg Lys Lys Ser Ser Gly Gly Lys Gly Gly Ser Tyr Ser
    450                 455                 460
Lys Ala Glu Trp Ser Asp Ser Ala Gln Gly Ser Glu Ser His Ser Leu
465                 470                 475                 480
Glu Gly Arg Gly Ser Leu Leu Thr Cys Gly Asp Val Glu Glu Asn Pro
                485                 490                 495
Gly Pro Met Leu Gln Met Ala Gly Gln Cys Ser Gln Asn Glu Tyr Phe
            500                 505                 510
Asp Ser Leu Leu His Ala Cys Ile Pro Cys Gln Leu Arg Cys Ser Ser
```

```
                  515                 520                 525
Asn Thr Pro Leu Thr Cys Gln Arg Tyr Cys Asn Ala Ser Val Thr
530                 535                 540

Asn Ser Val Lys Gly Thr Asn Ala Ile Leu Trp Thr Cys Leu Gly Leu
545                 550                 555                 560

Ser Leu Ile Ile Ser Leu Ala Val Phe Val Leu Met Phe Leu Leu Arg
                565                 570                 575

Lys Ile Asn Ser Glu Pro Leu Lys Asp Glu Phe Lys Asn Thr Gly Ser
                580                 585                 590

Gly Leu Leu Gly Met Ala Asn Ile Asp Leu Glu Lys Ser Arg Thr Gly
                595                 600                 605

Asp Glu Ile Ile Leu Pro Arg Gly Leu Glu Tyr Thr Val Glu Glu Cys
610                 615                 620

Thr Cys Glu Asp Cys Ile Lys Ser Lys Pro Lys Val Asp Ser Asp His
625                 630                 635                 640

Cys Phe Pro Leu Pro Ala Met Glu Glu Gly Ala Thr Ile Leu Val Thr
                645                 650                 655

Thr Lys Thr Asn Asp Tyr Cys Lys Ser Leu Pro Ala Ala Leu Ser Ala
                660                 665                 670

Thr Glu Ile Glu Lys Ser Ile Ser Ala Arg
                675                 680

<210> SEQ ID NO 64
<211> LENGTH: 220
<212> TYPE: PRT
<213> ORGANISM: Homo sapiens
<220> FEATURE:
<221> NAME/KEY: misc_feature
<222> LOCATION: (1)..(220)
<223> OTHER INFORMATION: CD28

<400> SEQUENCE: 64

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
                35                  40                  45

Arg Glu Phe Arg Ala Ser Leu His Lys Gly Leu Asp Ser Ala Val Glu
            50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Pro Tyr Leu Asp Asn Glu Lys Ser
                115                 120                 125

Asn Gly Thr Ile Ile His Val Lys Gly Lys His Leu Cys Pro Ser Pro
130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190
```

```
Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

<210> SEQ ID NO 65
<211> LENGTH: 1502
<212> TYPE: DNA
<213> ORGANISM: Artificial Sequence
<220> FEATURE:
<223> OTHER INFORMATION: Synthetic: HLA-G/B2M/HLA-E fusion nucleotide sequence reverse

<400> SEQUENCE: 65

```
tacaagctgt gagactcaga ccctgggca ctgtcgctcc actcagcctt agagtagctc    60
cctccttttc cacctgagct cttcttcctc catatcacag cagcaaccac agctccagag   120
accacagatc caaggagaac caggccagca atgatgccca cgatggggat ggtgggctgg   180
gaagccggct tccatctcag ggtgacgggc tcgggtagcc cctcatgctg cacatggcac   240
gtgtatctct gctcctctcc agaaggcacc accacagctg cccacttctg aaggttcca    300
tccctgcag gcctggtctc cacgagctcc gtgtcctggg tatggccctc ccatcctgc    360
tgccaggtca gtgtgatctc cgcagggtag aagcccaggg cccagcacct cagggtggcc   420
tcatggtcag agatggggtg gtgagtcacg tgtgtctttg ggggctccag gtgaagcagc   480
gtctccttcc ccttctccag gtatttgtgg agccactcca cgcatgtgtc ttccaggtag   540
gctctctggt gctccgcctc agaagcatca tttgactttt gctcggagat ctgagccgcc   600
gtgtccaccg cggtccagga gcgcaggtcc tcattcaggg tgagataatc cttgccgtcg   660
taggcgaact gttcataccc gcggaggaag cgcccgtcgg gccccagctc gcagccatgc   720
atccactgca gggtgtgaga cccggcctcg ctctgattgt agtagccgcg cagcgtccgc   780
agattcactc ggaaaatctg tgcggtgtcc ctggcgctcc gtgtctcccg gtcccaatac   840
tctgacccct cctgctccat ccacggcgcc cgcggcacca tcctcggact cgcggcgtcg   900
ttgtcgaagc gcacgaactg ggtgtcgtcc acgtagccca cagagatgaa gcggggctcc   960
ccgcggccgg gccgggacac ggaagtgtgg aaatacttca aggagtggga tccagaccct  1020
ccgccaccag atcccctcc tccagaaccg cctccgccag accctccgcc acccatgtct  1080
cgatcccact aactatctt gggctgtgac aaagtcacat ggttcacacg gcaggcatac  1140
tcatcttttt cagtgggggt gaattcagtg tagtacaaga gatagaaaga ccagtccttg  1200
ctgaaagaca agtctgaatg ctccactttt tcaattctct ctccattctt cagtaagtca  1260
acttcaatgt cggatggatg aaacccagac acatagcaat tcaggaaatt tgactttcca  1320
ttctctgctg gatgacgtga gtaaacctga atctttggag tacgctggat ggagccgccg  1380
cctccgctac cgcctcctcc gctcccacct ccacccagaa agagggtccg tggtgccatt  1440
acagcctcca ggccagaaag agagagtagc gcgagcacag ctaaggccac ggagcgagac  1500
at                                                                1502
```

<210> SEQ ID NO 66
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: B2M left homology arm

```
<400> SEQUENCE: 66
ttcccaagct gtagttataa acagaagttc tccttctgct aggtagcatt caaagatctt      60
aatcttctgg gtttccgttt tctcgaatga aaaatgcagg tccgagcagt taactggctg     120
gggcaccatt agcaagtcac ttagcatctc tggggccagt ctgcaaagcg aggggcagc      180 cttaatgtgc ctccagcctg aagtcctaga atgagcgccc ggtgtcccaa gctggggcgc     240 gcacccccaga tcggagggcg ccgatgtaca gacagcaaac tcacccagtc tagtgcatgc    300
cttcttaaac atcacgagac tctaagaaaa ggaaactgaa aacgggaaag tccctctctc     360
taacctggca ctgcgtcgct ggcttggaga caggtgacgg tccctgcggg ccttgtcctg     420
attggctggg cacgcgttta atataagtgg aggcgtcgcg ctggcgggca ttcctgaagc     480
tgacagcatt cgggccgaga                                                 500

<210> SEQ ID NO 67
<211> LENGTH: 480
<212> TYPE: DNA
<213> ORGANISM: Homo sapiens
<220> FEATURE:
<221> NAME/KEY: misc_feature
<222> LOCATION: (1)..(480)
<223> OTHER INFORMATION: B2M right homology arm

<400> SEQUENCE: 67
gctgtgctcg cgctactctc tctttctggc ctggaggcta tccagcgtga gtctctccta     60
ccctcccgct ctggtccttc ctctcccgct ctgcaccctc tgtggccctc gctgtgctct    120
ctcgctccgt gacttccctt ctccaagttc tccttggtgg cccgccgtgg ggctagtcca    180
gggctggatc tcggggaagc ggcgggggtgg cctgggagtg gggaaggggg tgcgcacccg   240
ggacgcgcgc tacttgcccc tttcggcggg gagcagggga gacctttggc ctacggcgac   300
gggagggtcg ggacaaagtt tagggcgtcg ataagcgtca gagcgccgag gttggggggag  360 ggtttctctt ccgctctttc gcggggcctc tggctccccc agcgcagctg gagtggggga   420
cgggtaggct cgtcccaaag gcgcggcgct gaggtttgtg aacgcgtgga ggggcgcttg   480
```